United States Patent
Wong et al.

(10) Patent No.: US 10,814,130 B2
(45) Date of Patent: Oct. 27, 2020

(54) DRY ELECTRODES FOR TRANSCUTANEOUS NERVE STIMULATION

(71) Applicant: Cala Health, Inc., Burlingame, CA (US)

(72) Inventors: Serena HanYing Wong, Palo Alto, CA (US); Gregory T. Schulte, Oakland, CA (US); Samuel Richard Hamner, San Francisco, CA (US); Kathryn H. Rosenbluth, San Francisco, CA (US); John Vincent Colombo, Burlingame, CA (US)

(73) Assignee: Cala Health, Inc., Burlingame, CA (US)

( * ) Notice: Subject to any disclaimer, the term of this patent is extended or adjusted under 35 U.S.C. 154(b) by 0 days.

(21) Appl. No.: 16/241,846

(22) Filed: Jan. 7, 2019

(65) Prior Publication Data

US 2019/0134393 A1 May 9, 2019

Related U.S. Application Data

(63) Continuation of application No. PCT/US2017/040920, filed on Jul. 6, 2017.
(Continued)

(51) Int. Cl.
*A61N 1/36* (2006.01)
*A61N 1/04* (2006.01)
(Continued)

(52) U.S. Cl.
CPC .......... *A61N 1/36021* (2013.01); *A61N 1/04* (2013.01); *A61N 1/0456* (2013.01);
(Continued)

(58) Field of Classification Search
CPC .............. H01L 51/0048; H01L 51/444; B29K 2995/0005; B29K 2507/04;
(Continued)

(56) References Cited

U.S. PATENT DOCUMENTS 3,204,637 A   9/1965 Frank et al.
3,870,051 A   3/1975 Brindley
(Continued)

FOREIGN PATENT DOCUMENTS

DE   102008042373   4/2010
DE   102009004011   7/2010
(Continued)

OTHER PUBLICATIONS

U.S. Appl. No. 15/748,616, filed Jan. 29, 2018, Hamner et al.
(Continued)

*Primary Examiner* — Deborah L Malamud
(74) *Attorney, Agent, or Firm* — Knobbe, Martens, Olson & Bear LLP

(57) ABSTRACT

Disclosed herein are systems, devices, and methods for peripheral nerve stimulation, particularly for treating tremor. The nerve stimulation may be accomplished by a wearable nerve stimulation device, such as a band configured to be worn on the wrist or other body part. The device can accomplish targeted nerve stimulation using circumferentially spaced electrodes. In some embodiments, the device may use only the same number of electrodes as the number of nerves that are to be stimulated. A biphasic charge-balanced waveform may be used to selectively stimulate a nerve near one of the activated electrodes but not to stimulate the nerve near the other activated electrode. The device may use dry electrodes for long-term, repeated use. The dry electrodes may include a conductive base layer and a polymeric, plastic or rubber skin contact layer comprising a
(Continued)

conductive filler. The filler may be a powder, fiber, conductive coating, etc.

20 Claims, 25 Drawing Sheets

Related U.S. Application Data

(60) Provisional application No. 62/432,519, filed on Dec. 9, 2016, provisional application No. 62/360,265, filed on Jul. 8, 2016.

(51) Int. Cl.
*A61N 1/32* (2006.01)
*A61N 1/18* (2006.01)
*A61N 1/378* (2006.01)
*A61B 5/00* (2006.01)

(52) U.S. Cl.
CPC ......... *A61N 1/0484* (2013.01); *A61N 1/0492* (2013.01); *A61N 1/18* (2013.01); *A61N 1/32* (2013.01); *A61N 1/36* (2013.01); *A61N 1/36025* (2013.01); *A61N 1/36067* (2013.01); *A61N 1/3787* (2013.01); *A61B 5/681* (2013.01); *A61N 1/0476* (2013.01); *A61N 1/36007* (2013.01); *A61N 1/36031* (2017.08)

(58) Field of Classification Search
CPC ........ B29K 2105/162; B29K 2105/167; B29K 2105/16; B29K 2307/04; B29K 2995/0006; H01B 1/04; H01B 5/14; Y10S 977/742; B32B 2313/04; A61N 1/0456; A61N 1/0492; A61N 1/3968; A61N 1/0452; A61N 1/0476; Y10T 428/30

See application file for complete search history.

(56) References Cited

U.S. PATENT DOCUMENTS

| | | | |
|---|---|---|---|
| 4,300,575 A | 11/1981 | Wilson | |
| 4,458,696 A | 7/1984 | Larimore | |
| 4,461,075 A | 7/1984 | Bailey | |
| 4,569,351 A | 2/1986 | Tang | |
| 4,582,049 A | 4/1986 | Ylvisaker | |
| 4,739,764 A | 4/1988 | Lue et al. | |
| 4,763,659 A | 8/1988 | Dunseath, Jr. | |
| 4,771,779 A | 9/1988 | Tanagho et al. | |
| 4,981,146 A | 1/1991 | Bertolucci | |
| 5,003,978 A | 4/1991 | Dunseath, Jr. | |
| 5,052,391 A | 10/1991 | Silverstone et al. | |
| 5,070,862 A | 12/1991 | Berlant | |
| 5,137,507 A | 8/1992 | Park | |
| 5,330,516 A | 7/1994 | Nathan | |
| 5,397,338 A | 3/1995 | Grey et al. | |
| 5,540,235 A | 7/1996 | Wilson | |
| 5,562,707 A | 10/1996 | Prochazka et al. | |
| 5,562,717 A | 10/1996 | Tippey et al. | |
| 5,573,011 A | 11/1996 | Felsing | |
| 5,575,294 A | 11/1996 | Perry et al. | |
| 5,643,173 A | 7/1997 | Welles | |
| 5,775,331 A | 7/1998 | Raymond et al. | |
| 5,833,709 A | 11/1998 | Rise et al. | |
| 5,833,716 A | 11/1998 | Bar-Or et al. | |
| 5,899,922 A | 5/1999 | Loos | |
| 6,016,449 A | 1/2000 | Fischell et al. | |
| 6,081,744 A | 6/2000 | Loos | |
| 6,161,044 A | 12/2000 | Silverstone | |
| 6,178,352 B1 | 1/2001 | Gruzdowich et al. | |
| 6,351,674 B2 | 2/2002 | Silverstone | |
| 6,366,813 B1 | 4/2002 | DiLorenzo | |
| 6,445,955 B1 | 9/2002 | Michelson et al. | |
| 6,449,512 B1 | 9/2002 | Boveja | |
| 6,505,074 B2 | 1/2003 | Boveja et al. | |
| 6,546,290 B1 | 4/2003 | Shloznikov | |
| 6,564,103 B2 | 5/2003 | Fischer et al. | |
| 6,652,449 B1 | 11/2003 | Gross et al. | |
| 6,704,603 B1 | 3/2004 | Gesotti | |
| 6,731,987 B1 | 5/2004 | McAdams et al. | |
| 6,735,474 B1 | 5/2004 | Loeb et al. | |
| 6,735,480 B2 | 5/2004 | Giuntoli et al. | |
| 6,788,976 B2 | 9/2004 | Gesotti | |
| 6,819,956 B2 | 11/2004 | DiLorenzo | |
| 6,829,510 B2 | 12/2004 | Nathan et al. | |
| 6,836,684 B1 | 12/2004 | Rijkhoff et al. | |
| 6,862,480 B2 | 3/2005 | Cohen et al. | |
| 6,892,098 B2 | 5/2005 | Ayal et al. | |
| 6,937,905 B2 | 8/2005 | Carroll et al. | |
| 6,959,215 B2 | 10/2005 | Gliner et al. | |
| 6,959,216 B2 | 10/2005 | Faghri | |
| 6,988,005 B2 | 1/2006 | McGraw et al. | |
| 7,010,352 B2 | 3/2006 | Hogan | |
| 7,089,061 B2 | 8/2006 | Grey | |
| 7,146,220 B2 | 12/2006 | Dar et al. | |
| 7,162,305 B2 | 1/2007 | Tong et al. | |
| 7,171,266 B2 | 1/2007 | Gruzdowich et al. | |
| 7,177,694 B2 | 2/2007 | Elbaum | |
| 7,177,703 B2 | 2/2007 | Boveja et al. | |
| 7,209,787 B2 | 4/2007 | DiLorenzo | |
| 7,228,178 B2 | 6/2007 | Carroll et al. | |
| 7,231,254 B2 | 6/2007 | DiLorenzo | |
| 7,236,830 B2 | 6/2007 | Gliner | |
| 7,254,444 B2 | 8/2007 | Moore et al. | |
| 7,277,758 B2 | 10/2007 | DiLorenzo | |
| 7,324,851 B1 | 1/2008 | DiLorenzo | |
| 7,326,235 B2 | 2/2008 | Edwards | |
| 7,328,068 B2 | 2/2008 | Spinelli et al. | |
| 7,349,739 B2 | 3/2008 | Harry et al. | |
| 7,353,064 B2 | 4/2008 | Gliner et al. | |
| 7,369,896 B2 | 5/2008 | Gesotti | |
| 7,499,747 B2 | 3/2009 | Kieval et al. | |
| 7,529,582 B1 | 5/2009 | DiLorenzo | |
| 7,558,610 B1 | 7/2009 | Odderson | |
| 7,636,602 B2 | 12/2009 | Baru Fassio et al. | |
| 7,643,880 B2 | 1/2010 | Tanagho et al. | |
| 7,643,882 B2 | 1/2010 | Boston | |
| 7,650,190 B2 | 1/2010 | Zhou et al. | |
| 7,742,820 B2 | 6/2010 | Wyler et al. | |
| 7,769,464 B2 | 8/2010 | Gerber et al. | |
| 7,857,771 B2 | 12/2010 | Alwan et al. | |
| 7,899,556 B2 | 3/2011 | Nathan et al. | |
| 7,917,201 B2 | 3/2011 | Gozani et al. | |
| 7,930,034 B2 | 4/2011 | Gerber | |
| 7,949,403 B2 | 5/2011 | Palermo et al. | |
| 7,957,814 B2 | 6/2011 | Goetz et al. | |
| 7,974,696 B1 | 7/2011 | DiLorenzo | |
| 7,974,698 B2 | 7/2011 | Tass et al. | |
| 7,996,088 B2 | 8/2011 | Marrosu et al. | |
| 7,998,092 B2 | 8/2011 | Avni et al. | |
| 8,000,796 B2 | 8/2011 | Tass et al. | |
| 8,025,632 B2 | 9/2011 | Einarsson | |
| 8,046,083 B2 | 10/2011 | Teganthoff et al. | |
| 8,075,499 B2 | 12/2011 | Nathan et al. | |
| 8,086,318 B2 | 12/2011 | Strother et al. | |
| 8,121,694 B2 | 2/2012 | Molnar et al. | |
| 8,145,316 B2 | 3/2012 | Deem et al. | |
| 8,165,668 B2 | 4/2012 | Dacey, Jr. et al. | |
| 8,187,209 B1 | 5/2012 | Guiffrida et al. | |
| 8,219,188 B2 | 7/2012 | Craig | |
| 8,233,988 B2 | 7/2012 | Errico et al. | |
| 8,260,439 B2 | 9/2012 | Diubaldi et al. | |
| 8,301,215 B2 | 10/2012 | Lee | |
| 8,306,624 B2 | 11/2012 | Gerber et al. | |
| 8,313,443 B2 | 11/2012 | Tom | |
| 8,343,026 B2 | 1/2013 | Gardiner et al. | |
| 8,364,257 B2 | 1/2013 | Van Den Eerenbeemd et al. | |
| 8,374,701 B2 | 2/2013 | Hyde et al. | |
| 8,380,314 B2 | 2/2013 | Panken et al. | |
| 8,382,688 B2 | 2/2013 | Dar et al. | |
| 8,391,970 B2 | 3/2013 | Tracey et al. | |
| 8,396,556 B2 | 3/2013 | Libbus et al. | |

(56) References Cited

U.S. PATENT DOCUMENTS

| | | |
|---|---|---|
| 8,409,116 B2 | 4/2013 | Wang et al. |
| 8,412,338 B2 | 4/2013 | Faltys |
| 8,414,507 B2 | 4/2013 | Asada |
| 8,428,719 B2 | 4/2013 | Napadow |
| 8,435,166 B2 | 5/2013 | Burnett et al. |
| 8,447,411 B2 | 5/2013 | Skelton et al. |
| 8,452,410 B2 | 5/2013 | Emborg et al. |
| 8,463,374 B2 | 6/2013 | Hudson et al. |
| 8,473,064 B2 | 6/2013 | Castel et al. |
| 8,548,594 B2 | 10/2013 | Thimineur et al. |
| 8,581,731 B2 | 11/2013 | Purks et al. |
| 8,583,238 B1 | 11/2013 | Heldman et al. |
| 8,588,884 B2 | 11/2013 | Hegde et al. |
| 8,588,917 B2 | 11/2013 | Whitehurst et al. |
| 8,608,671 B2 | 12/2013 | Kinoshita et al. |
| 8,626,305 B2 | 1/2014 | Nielsen et al. |
| 8,639,342 B2 | 1/2014 | Possover |
| 8,644,904 B2 | 2/2014 | Chang et al. |
| 8,644,938 B2 | 2/2014 | Craggs |
| 8,660,656 B2 | 2/2014 | Moser et al. |
| 8,666,496 B2 | 3/2014 | Simon et al. |
| 8,679,038 B1 | 3/2014 | Giuffrida |
| 8,682,441 B2 | 3/2014 | De Ridder |
| 8,688,220 B2 | 4/2014 | Degiorgio et al. |
| 8,694,104 B2 | 4/2014 | Libbus et al. |
| 8,694,110 B2 | 4/2014 | Nathan et al. |
| 8,702,584 B2 | 4/2014 | Rigaux et al. |
| 8,702,629 B2 | 4/2014 | Giuffrida et al. |
| 8,706,241 B2 | 4/2014 | Firlik et al. |
| 8,718,780 B2 | 5/2014 | Lee |
| 8,740,825 B2 | 6/2014 | Ehrenreich et al. |
| 8,744,587 B2 | 6/2014 | Miesel et al. |
| 8,755,892 B2 | 6/2014 | Amurthur et al. |
| 8,768,452 B2 | 7/2014 | Gerber |
| 8,788,045 B2 | 7/2014 | Gross et al. |
| 8,788,049 B2 | 7/2014 | Lasko et al. |
| 8,792,977 B2 | 7/2014 | Kakei et al. |
| 8,798,698 B2 | 8/2014 | Kim et al. |
| 8,821,416 B2 | 9/2014 | Johansson et al. |
| 8,825,163 B2 | 9/2014 | Grill et al. |
| 8,825,165 B2 | 9/2014 | Possover |
| 8,843,201 B1 | 9/2014 | Heldman et al. |
| 8,845,494 B2 | 9/2014 | Whitall et al. |
| 8,845,557 B1 | 9/2014 | Giuffrida et al. |
| 8,855,775 B2 | 10/2014 | Leyde |
| 8,862,238 B2 | 10/2014 | Rahimi et al. |
| 8,862,247 B2 | 10/2014 | Schoendorf et al. |
| 8,868,177 B2 | 10/2014 | Simon et al. |
| 8,874,227 B2 | 10/2014 | Simon et al. |
| 8,880,175 B2 | 11/2014 | Simon |
| 8,886,321 B2 | 11/2014 | Rohrer et al. |
| 8,892,200 B2 | 11/2014 | Wagner et al. |
| 8,897,870 B2 | 11/2014 | De Ridder |
| 8,903,494 B2 | 12/2014 | Goldwasser et al. |
| 8,920,345 B2 | 12/2014 | Greenberg et al. |
| 8,923,970 B2 | 12/2014 | Bar-Yoseph et al. |
| 8,948,876 B2 | 2/2015 | Gozani et al. |
| 8,961,439 B2 | 2/2015 | Yang et al. |
| 8,972,017 B2 | 3/2015 | Dar et al. |
| 8,989,861 B2 | 3/2015 | Su et al. |
| 9,002,477 B2 | 4/2015 | Burnett |
| 9,005,102 B2 | 4/2015 | Burnett et al. |
| 9,008,781 B2 | 4/2015 | Ahmed |
| 9,011,310 B2 | 4/2015 | Ahmed |
| 9,017,273 B2 | 4/2015 | Burbank et al. |
| 9,026,216 B2 | 5/2015 | Rossi et al. |
| 9,042,988 B2 | 5/2015 | Dilorenzo |
| 9,060,747 B2 | 6/2015 | Salorio |
| 9,089,691 B2 | 7/2015 | Libbus et al. |
| 9,095,351 B2 | 8/2015 | Sachs et al. |
| 9,095,417 B2 | 8/2015 | Dar et al. |
| 9,107,614 B2 | 8/2015 | Halkias et al. |
| 9,119,964 B2 | 9/2015 | Marnfeldt |
| 9,155,885 B2 | 10/2015 | Wei et al. |
| 9,155,890 B2 | 10/2015 | Guntinas-Lichius et al. |
| 9,162,059 B1 | 10/2015 | Lindenthaler |
| 9,168,374 B2 | 10/2015 | Su |
| 9,174,045 B2 | 11/2015 | Simon et al. |
| 9,186,095 B2 | 11/2015 | Machado et al. |
| 9,192,763 B2 | 11/2015 | Gerber et al. |
| 9,220,895 B2 | 12/2015 | Siff et al. |
| 9,227,056 B2 | 1/2016 | Heldman et al. |
| 9,238,142 B2 | 1/2016 | Heldman et al. |
| 9,248,285 B2 | 2/2016 | Haessler |
| 9,248,297 B2 | 2/2016 | Hoyer et al. |
| 9,254,382 B2 | 2/2016 | Ahmad et al. |
| 9,265,927 B2 | 2/2016 | Yonce et al. |
| 9,282,928 B1 | 3/2016 | Giffrida |
| 9,289,607 B2 | 3/2016 | Su et al. |
| 9,301,712 B2 | 4/2016 | McNames et al. |
| 9,302,046 B2 | 4/2016 | Giuffrida et al. |
| 9,314,190 B1 | 4/2016 | Giuffrida et al. |
| 9,314,622 B2 | 4/2016 | Embrey et al. |
| 9,332,918 B1 | 5/2016 | Buckley et al. |
| 9,339,641 B2 | 5/2016 | Rajguru et al. |
| 9,345,872 B2 | 5/2016 | Groteke |
| 9,364,657 B2 | 6/2016 | Kiani et al. |
| 9,364,672 B2 | 6/2016 | Marnfeldt |
| 9,375,570 B2 | 6/2016 | Kiani et al. |
| 9,408,683 B2 | 8/2016 | St. Anne et al. |
| 9,414,776 B2 | 8/2016 | Sillay et al. |
| 9,452,287 B2 | 9/2016 | Rosenbluth et al. |
| 9,474,898 B2 | 10/2016 | Gozani et al. |
| 9,549,872 B2 | 1/2017 | Chen et al. |
| 9,586,038 B1 | 3/2017 | Kosierkiewicz |
| 9,675,800 B2 | 6/2017 | Li et al. |
| 9,802,041 B2 | 10/2017 | Wong et al. |
| 9,861,283 B1 | 1/2018 | Giuffrida |
| 9,877,679 B1 | 1/2018 | Giuffrida |
| 9,877,680 B1 | 1/2018 | Giuffrida et al. |
| 9,924,899 B2 | 3/2018 | Pracar et al. |
| 9,974,478 B1 | 5/2018 | Brokaw et al. |
| 9,980,659 B2 | 5/2018 | Sadeghian-Motahar et al. |
| 10,004,900 B2 | 6/2018 | Kent et al. |
| 10,022,545 B1 | 7/2018 | Giuffrida |
| 10,028,695 B2 | 7/2018 | Machado et al. |
| 10,173,060 B2 | 1/2019 | Wong et al. |
| 10,179,238 B2 | 1/2019 | Wong et al. |
| 2002/0161415 A1 | 10/2002 | Cohen et al. |
| 2002/0165586 A1 | 11/2002 | Hill et al. |
| 2003/0032992 A1 | 2/2003 | Thacker et al. |
| 2003/0088294 A1 | 5/2003 | Gesotti |
| 2003/0149457 A1 | 8/2003 | Tcheng et al. |
| 2003/0187483 A1 | 10/2003 | Grey et al. |
| 2003/0195583 A1 | 10/2003 | Gruzdowich et al. |
| 2004/0093093 A1 | 5/2004 | Andrews |
| 2004/0133249 A1 | 7/2004 | Gesotti |
| 2004/0249416 A1 | 12/2004 | Yun et al. |
| 2004/0267331 A1 | 12/2004 | Koeneman et al. |
| 2005/0021103 A1 | 1/2005 | DiLorenzo |
| 2005/0055063 A1 | 3/2005 | Loeb et al. |
| 2005/0065553 A1 | 3/2005 | Ben Ezra et al. |
| 2005/0075502 A1 | 4/2005 | Shafer |
| 2005/0171577 A1 | 8/2005 | Cohen et al. |
| 2005/0234309 A1 | 10/2005 | Klapper |
| 2006/0047326 A1 | 3/2006 | Wheeler |
| 2006/0052726 A1 | 3/2006 | Weisz et al. |
| 2006/0095088 A1 | 5/2006 | De Ridder |
| 2006/0161218 A1 | 7/2006 | Danilov |
| 2006/0184059 A1 | 8/2006 | Jadidi |
| 2006/0217781 A1 | 9/2006 | John |
| 2006/0224191 A1 | 10/2006 | DiLorenzo |
| 2006/0229678 A1 | 10/2006 | Lee |
| 2006/0276853 A1 | 12/2006 | Tass |
| 2006/0293723 A1 | 12/2006 | Whitehurst et al. |
| 2007/0027486 A1 | 2/2007 | Armstrong |
| 2007/0073361 A1 | 3/2007 | Goren et al. |
| 2007/0123951 A1 | 5/2007 | Boston |
| 2007/0123952 A1 | 5/2007 | Strother et al. |
| 2007/0142862 A1 | 6/2007 | DiLorenzo |
| 2007/0156179 A1 | 7/2007 | Karashurov |
| 2007/0156182 A1 | 7/2007 | Castel et al. |
| 2007/0156183 A1 | 7/2007 | Rhodes |
| 2007/0156200 A1 | 7/2007 | Kornet et al. |

(56) References Cited

U.S. PATENT DOCUMENTS

| | | |
|---|---|---|
| 2007/0173899 A1 | 7/2007 | Levin et al. |
| 2007/0173903 A1 | 7/2007 | Goren et al. |
| 2007/0203533 A1 | 8/2007 | Goren et al. |
| 2007/0207193 A1 | 9/2007 | Zasler et al. |
| 2007/0282228 A1 | 12/2007 | Einav et al. |
| 2008/0004672 A1 | 1/2008 | Dalal et al. |
| 2008/0009772 A1 | 1/2008 | Tyler et al. |
| 2008/0021505 A1 | 1/2008 | Hastings et al. |
| 2008/0027507 A1 | 1/2008 | Bijelic et al. |
| 2008/0033259 A1 | 2/2008 | Manto et al. |
| 2008/0051839 A1 | 2/2008 | Libbus et al. |
| 2008/0058773 A1 | 3/2008 | John |
| 2008/0058893 A1 | 3/2008 | Noujokat |
| 2008/0147146 A1 | 6/2008 | Wahlgren et al. |
| 2008/0177398 A1 | 7/2008 | Gross et al. |
| 2008/0195007 A1 | 8/2008 | Podrazhansky et al. |
| 2008/0208288 A1 | 8/2008 | Gesotti |
| 2008/0216593 A1 | 9/2008 | Jacobsen et al. |
| 2009/0018609 A1 | 1/2009 | DiLorenzo |
| 2009/0105785 A1 | 4/2009 | Wei et al. |
| 2009/0112133 A1 | 4/2009 | Deisseroth et al. |
| 2009/0157138 A1 | 6/2009 | Errico et al. |
| 2009/0187121 A1 | 7/2009 | Evans |
| 2009/0216294 A1 | 8/2009 | Ewing et al. |
| 2009/0247910 A1 | 10/2009 | Klapper |
| 2009/0299435 A1 | 12/2009 | Gliner et al. |
| 2009/0318986 A1 | 12/2009 | Alo et al. |
| 2009/0326595 A1 | 12/2009 | Brockway et al. |
| 2009/0326607 A1 | 12/2009 | Castel et al. |
| 2010/0010381 A1 | 1/2010 | Skelton et al. |
| 2010/0010572 A1 | 1/2010 | Skelton et al. |
| 2010/0057154 A1 | 3/2010 | Dietrich et al. |
| 2010/0099963 A1 | 4/2010 | Kilger |
| 2010/0107657 A1 | 5/2010 | Vistakula |
| 2010/0125220 A1 | 5/2010 | Seong |
| 2010/0152817 A1 | 6/2010 | Gillbe |
| 2010/0174342 A1 | 7/2010 | Boston et al. |
| 2010/0222630 A1 | 9/2010 | Mangrum et al. |
| 2010/0227330 A1 | 9/2010 | Fink et al. |
| 2010/0249637 A1 | 9/2010 | Walter et al. |
| 2010/0292527 A1 | 11/2010 | Schneider et al. |
| 2010/0298905 A1 | 11/2010 | Simon |
| 2010/0324611 A1 | 12/2010 | Deming et al. |
| 2011/0009920 A1 | 1/2011 | Whitehurst et al. |
| 2011/0021899 A1* | 1/2011 | Arps ............... A61K 9/0009 600/372 |
| 2011/0040204 A1 | 2/2011 | Ivorra et al. |
| 2011/0054358 A1 | 3/2011 | Kim et al. |
| 2011/0071590 A1 | 3/2011 | Mounaim et al. |
| 2011/0118805 A1 | 5/2011 | Wei et al. |
| 2011/0137375 A1 | 6/2011 | McBride |
| 2011/0184489 A1 | 7/2011 | Nicolelis et al. |
| 2011/0202107 A1 | 8/2011 | Sunagawa et al. |
| 2011/0213278 A1 | 9/2011 | Horak et al. |
| 2011/0224571 A1 | 9/2011 | Pascual-Leone et al. |
| 2011/0245734 A1 | 10/2011 | Wagner et al. |
| 2011/0250297 A1 | 10/2011 | Oronsky et al. |
| 2011/0282412 A1 | 11/2011 | Glukhovsky et al. |
| 2011/0301663 A1 | 12/2011 | Wang et al. |
| 2012/0010492 A1 | 1/2012 | Thramann et al. |
| 2012/0053491 A1 | 3/2012 | Nathan et al. |
| 2012/0088986 A1 | 4/2012 | David et al. |
| 2012/0092178 A1 | 4/2012 | Callsen et al. |
| 2012/0109013 A1 | 5/2012 | Everett et al. |
| 2012/0136410 A1 | 5/2012 | Rezai et al. |
| 2012/0185020 A1 | 7/2012 | Simon et al. |
| 2012/0220812 A1 | 8/2012 | Mishelevich |
| 2012/0239112 A1 | 9/2012 | Muraoka |
| 2012/0259255 A1 | 10/2012 | Tomlinson et al. |
| 2012/0302821 A1 | 11/2012 | Burnett |
| 2012/0310298 A1 | 12/2012 | Besio et al. |
| 2012/0310303 A1 | 12/2012 | Popovic et al. |
| 2013/0060124 A1 | 3/2013 | Zietsma |
| 2013/0066388 A1 | 3/2013 | Bernhard et al. |
| 2013/0066395 A1 | 3/2013 | Simon et al. |
| 2013/0116606 A1 | 5/2013 | Cordo |
| 2013/0131484 A1 | 5/2013 | Pernu |
| 2013/0158624 A1 | 6/2013 | Bain et al. |
| 2013/0231713 A1 | 9/2013 | De Ridder et al. |
| 2013/0236867 A1 | 9/2013 | Avni et al. |
| 2013/0238049 A1 | 9/2013 | Simon et al. |
| 2013/0245486 A1 | 9/2013 | Simon et al. |
| 2013/0245713 A1 | 9/2013 | Tass |
| 2013/0253299 A1 | 9/2013 | Weber et al. |
| 2013/0267759 A1 | 10/2013 | Jin |
| 2013/0281890 A1 | 10/2013 | Mishelevich |
| 2013/0289647 A1 | 10/2013 | Bhadra et al. |
| 2013/0297022 A1 | 11/2013 | Pathak |
| 2013/0331907 A1 | 12/2013 | Sumners et al. |
| 2013/0333094 A1 | 12/2013 | Rogers et al. |
| 2013/0338726 A1 | 12/2013 | Machado |
| 2014/0031605 A1 | 1/2014 | Schneider |
| 2014/0039573 A1 | 2/2014 | Jindra |
| 2014/0039575 A1 | 2/2014 | Bradley |
| 2014/0046423 A1 | 2/2014 | Rajguru et al. |
| 2014/0058189 A1 | 2/2014 | Stubbeman |
| 2014/0067003 A1 | 3/2014 | Vase et al. |
| 2014/0078694 A1 | 3/2014 | Wissmar |
| 2014/0081345 A1 | 3/2014 | Hershey |
| 2014/0094675 A1 | 4/2014 | Luna et al. |
| 2014/0094873 A1 | 4/2014 | Emborg et al. |
| 2014/0132410 A1 | 5/2014 | Chang |
| 2014/0142654 A1 | 5/2014 | Simon et al. |
| 2014/0148873 A1 | 5/2014 | Kirn |
| 2014/0163444 A1 | 6/2014 | Ingvarsson |
| 2014/0171834 A1 | 6/2014 | DeGoede et al. |
| 2014/0214119 A1 | 7/2014 | Greiner et al. |
| 2014/0228927 A1 | 8/2014 | Ahmad et al. |
| 2014/0249452 A1 | 9/2014 | Marsh et al. |
| 2014/0257047 A1 | 9/2014 | Sillay et al. |
| 2014/0257129 A1 | 9/2014 | Choi et al. |
| 2014/0276194 A1 | 9/2014 | Osorio |
| 2014/0277220 A1 | 9/2014 | Brennan et al. |
| 2014/0296752 A1 | 10/2014 | Edgerton et al. |
| 2014/0296934 A1 | 10/2014 | Gozani et al. |
| 2014/0296935 A1 | 10/2014 | Ferree et al. |
| 2014/0300490 A1 | 10/2014 | Kotz et al. |
| 2014/0309709 A1 | 10/2014 | Gozanl et al. |
| 2014/0316484 A1 | 10/2014 | Edgerton et al. |
| 2014/0324118 A1 | 10/2014 | Simon et al. |
| 2014/0330068 A1 | 11/2014 | Partsch et al. |
| 2014/0330335 A1 | 11/2014 | Errico et al. |
| 2014/0336003 A1 | 11/2014 | Franz et al. |
| 2014/0336722 A1 | 11/2014 | Rocon De Lima et al. |
| 2014/0343462 A1 | 11/2014 | Burnet |
| 2014/0350436 A1 | 11/2014 | Nathan et al. |
| 2014/0358040 A1 | 12/2014 | Kim et al. |
| 2014/0364678 A1 | 12/2014 | Harry et al. |
| 2015/0005852 A1 | 1/2015 | Hershey et al. |
| 2015/0012067 A1 | 1/2015 | Bradley et al. |
| 2015/0038886 A1 | 2/2015 | Snow |
| 2015/0044656 A1* | 2/2015 | Eichhorn ............... A61B 5/686 434/267 |
| 2015/0057506 A1 | 2/2015 | Luna et al. |
| 2015/0073310 A1 | 3/2015 | Pracar et al. |
| 2015/0080979 A1 | 3/2015 | Lasko et al. |
| 2015/0100004 A1 | 4/2015 | Goldman et al. |
| 2015/0100104 A1 | 4/2015 | Kiani et al. |
| 2015/0100105 A1 | 4/2015 | Kiani et al. |
| 2015/0148866 A1 | 5/2015 | Bulsen et al. |
| 2015/0148878 A1 | 5/2015 | Yoo et al. |
| 2015/0157274 A1 | 6/2015 | Ghassemzadeh et al. |
| 2015/0164377 A1 | 6/2015 | Nathan et al. |
| 2015/0164401 A1 | 6/2015 | Toth et al. |
| 2015/0190085 A1 | 7/2015 | Nathan et al. |
| 2015/0190634 A1 | 7/2015 | Rezai et al. |
| 2015/0208955 A1 | 7/2015 | Smith |
| 2015/0216475 A1 | 8/2015 | Luna et al. |
| 2015/0230733 A1 | 8/2015 | Heo et al. |
| 2015/0230756 A1 | 8/2015 | Luna et al. |
| 2015/0277559 A1 | 10/2015 | Vescovi et al. |
| 2015/0321000 A1 | 11/2015 | Rosenbluth et al. |
| 2015/0335882 A1 | 11/2015 | Gross et al. |
| 2016/0001096 A1 | 1/2016 | Mishelevich |

(56) References Cited

U.S. PATENT DOCUMENTS

| | | |
|---|---|---|
| 2016/0008620 A1 | 1/2016 | Stubbeman |
| 2016/0016014 A1 | 1/2016 | Wagner et al. |
| 2016/0022989 A1 | 1/2016 | Pfeifer |
| 2016/0038059 A1 | 2/2016 | Asada et al. |
| 2016/0045140 A1 | 2/2016 | Kitamura et al. |
| 2016/0089045 A1 | 3/2016 | Sadeghian-Motahar et al. |
| 2016/0106344 A1 | 4/2016 | Nazari |
| 2016/0121110 A1 | 5/2016 | Kent et al. |
| 2016/0128621 A1 | 5/2016 | Machado et al. |
| 2016/0129248 A1 | 5/2016 | Creasey et al. |
| 2016/0158542 A1 | 6/2016 | Ahmed |
| 2016/0198998 A1 | 7/2016 | Rahimi et al. |
| 2016/0220836 A1 | 8/2016 | Parks |
| 2016/0262685 A1 | 9/2016 | Wagner et al. |
| 2016/0287879 A1 | 10/2016 | Denison et al. |
| 2017/0014625 A1 | 1/2017 | Rosenbluth et al. |
| 2017/0079597 A1 | 3/2017 | Horne |
| 2017/0080207 A1 | 3/2017 | Perez et al. |
| 2017/0157398 A1 | 6/2017 | Wong et al. |
| 2017/0266443 A1 | 9/2017 | Rajguru et al. |
| 2017/0274208 A1 | 9/2017 | Nagel et al. |
| 2017/0287146 A1 | 10/2017 | Pathak et al. |
| 2018/0049676 A1 | 2/2018 | Griffiths et al. |
| 2018/0064344 A1 | 3/2018 | Nguyen |
| 2018/0064944 A1 | 3/2018 | Grill et al. |
| 2018/0168905 A1 | 6/2018 | Goodall et al. |
| 2018/0169400 A1 | 6/2018 | Wong et al. |
| 2018/0214694 A1 | 8/2018 | Parramon |
| 2018/0221620 A1 | 8/2018 | Metzger |
| 2018/0235500 A1 | 8/2018 | Lee et al. |
| 2018/0236217 A1 | 8/2018 | Hamner et al. |
| 2018/0264263 A1 | 9/2018 | Rosenbluth et al. |
| 2019/0001129 A1 | 1/2019 | Hamner et al. |

FOREIGN PATENT DOCUMENTS

| | | |
|---|---|---|
| EP | 0000759 | 2/1979 |
| EP | 0725665 | 1/1998 |
| EP | 1062988 | 12/2000 |
| EP | 1558333 | 5/2007 |
| EP | 2383014 | 11/2011 |
| EP | 2801389 | 11/2014 |
| ES | 2222819 | 3/2006 |
| ES | 2272137 | 6/2008 |
| GB | 2496449 | 5/2013 |
| JP | 2002/200178 | 7/2002 |
| JP | 2006-503658 | 2/2006 |
| JP | 2008/018235 | 1/2008 |
| JP | 2012/055650 | 3/2012 |
| JP | 2013/017609 | 1/2013 |
| JP | 54-39921 | 3/2014 |
| WO | WO1994/000187 | 1/1994 |
| WO | WO1994/017855 | 8/1994 |
| WO | WO1996/032909 | 10/1996 |
| WO | WO1998/043700 | 10/1998 |
| WO | WO1999/019019 | 4/1999 |
| WO | WO2000/015293 | 3/2000 |
| WO | WO2002/017987 | 3/2002 |
| WO | WO2005/122894 | 12/2005 |
| WO | WO2007/112092 | 10/2007 |
| WO | WO2009/153730 | 12/2009 |
| WO | WO2010/111321 | 9/2010 |
| WO | WO2010/141155 | 12/2010 |
| WO | WO2011/119224 | 9/2011 |
| WO | WO2011/144883 | 11/2011 |
| WO | WO2012/040243 | 3/2012 |
| WO | WO2013/071307 | 5/2013 |
| WO | WO2013/074809 | 5/2013 |
| WO | WO2014/043757 | 3/2014 |
| WO | WO2014/053041 | 4/2014 |
| WO | WO2014/113813 | 7/2014 |
| WO | WO2014/146082 | 9/2014 |
| WO | WO2014/151431 | 9/2014 |
| WO | WO2014/153201 | 9/2014 |
| WO | WO2014/207512 | 12/2014 |
| WO | WO2015/033152 | 3/2015 |
| WO | WO2015/039206 | 3/2015 |
| WO | WO2015/039244 | 3/2015 |
| WO | WO2015/042365 | 3/2015 |
| WO | WO2015/079319 | 6/2015 |
| WO | WO2015/095880 | 6/2015 |
| WO | WO2015/128090 | 9/2015 |
| WO | WO2015/164706 | 10/2015 |
| WO | WO2015/187712 | 12/2015 |
| WO | WO2016/019250 | 2/2016 |
| WO | WO2016/102958 | 6/2016 |
| WO | WO2016/110804 | 7/2016 |
| WO | WO2016/128985 | 8/2016 |
| WO | WO2016/149751 | 9/2016 |
| WO | WO2016/166281 | 10/2016 |
| WO | WO2016/179407 | 11/2016 |
| WO | WO2016/189422 | 12/2016 |
| WO | WO2016/195587 | 12/2016 |
| WO | WO2016/201366 | 12/2016 |
| WO | WO2017/010930 | 1/2017 |
| WO | WO2017/023864 | 2/2017 |
| WO | WO2017/053847 | 3/2017 |
| WO | WO2017/062994 | 4/2017 |
| WO | WO2017/086798 | 5/2017 |
| WO | WO2017/088573 | 6/2017 |
| WO | WO2017/132067 | 8/2017 |
| WO | WO2017/199026 | 11/2017 |
| WO | WO2017/208167 | 12/2017 |
| WO | WO2017/209673 | 12/2017 |
| WO | WO2017/210729 | 12/2017 |
| WO | WO2017/221037 | 12/2017 |
| WO | WO2018/009680 | 1/2018 |
| WO | WO2018/028220 | 2/2018 |
| WO | WO2018/028221 | 2/2018 |
| WO | WO2018/039458 | 3/2018 |
| WO | WO 2018/112164 | 6/2018 |
| WO | WO 2018/187241 | 10/2018 |

OTHER PUBLICATIONS

U.S. Appl. No. 16/071,056, filed Jul. 18, 2018, Wong et al.
U.S. Appl. No. 16/242,983, filed Jan. 8, 2019, Wong et al.
U.S. Appl. No. 16/247,310, filed Jan. 14, 2019, Wong et al.
U.S. Appl. No. 16/327,780, filed Feb. 22, 2019, Hamner et al.
Apartis; Clinical neurophysiology in movement disorders. Handb Clin Neurol; 111; Pediatric Neurology Pt. 1; pp. 87-92;Apr. 2013.
Australian Office Action dated Jan. 10, 2017 in Australian Patent Application No. 2014207265 in 2 pages.
Barbaud et al.; Improvement in essential tremor after pure sensory stroke due to thalamic infarction; European neurology; 46; pp. 57-59; Jul. 2001.
Barrios et al.: BCI algorithms for tremor identification, characterization and tracking; Seventh Framework Programme, EU; Contract No. FP7-ICT-2007-224051 (v3.0); 57 pgs.; Jul. 10, 2011.
Bartley et al.; Neuromodulation for overactive bladder; Nature Reviews Urology; 10; pp. 513-521; Sep. 2013.
Benabid et al.; A putative generalized model of the effects and mechanism of action of high frequency electrical stimulation of the central nervous system; Acta Neural Belg; 105(3); pp. 149-157; Sep. 2005.
Bergquist et al.: Motor unit recruitment when neuromuscular electrical stimulation is applied over a nerve trunk compared with a muscle belly: quadriceps femoris, Journal of Applied Physiology; vol. 113, No. 1, pp. 78-89; Jul. 2012.
Bergquist et al.; Motor unit recruitment when neuromuscular electrical stimulation is applied over a nerve trunk compared with a muscle belly: triceps surae, Journal of Applied Physiology; vol. 110, No. 3, pp. 627-637; Mar. 2011.
Bijelic et al.: E Actitrode®: The New Selective Stimulation Interface for Functional Movements in Hemiplegic Patients; Serbian Journal of Electrical Engineering; 1(3); pp. 21-28; Nov. 2004.
Birdno et al.; Pulse-to-pulse changes in the frequency of deep brain stimulation affect tremor and modeled neuronal activity.; Journal of Neurophysiology; 98; pp. 1675-1684; Jul. 2007.

(56) References Cited

OTHER PUBLICATIONS

Birdno et al.; Response of human thalamic neurons to high-frequency stimulation.; PloS One; 9(5); 10 pgs.; May 2014.
Birgersson et al.; Non-invasive bioimpedance of intact skin: mathematical modeling and experiments; Physiological Measurement; 32(1); pp. 1-18; Jan. 2011.
Bohling et al.; Comparison of the stratum corneum thickness measured in vivo with confocal Raman spectroscopy and confocal reflectance microscopy; Skin research and Technology; 20(1); pp. 50-47; Feb. 2014.
Bonaz, B., V. Sinniger, and S. Pellissier. "Vagus nerve stimulation: a new promising therapeutic tool in inflammatory bowel disease." Journal of internal medicine 282.1 (2017): 46-63.
Bowman et al.; Effects of waveform parameters on comfort during transcutaneous neuromuscular electrical stimulation; Annals of Biomedical Engineering; 13(1); pp. 59-74; Jan. 1985.
Brittain et al.; Tremor suppression by rhythmic transcranial current stimulation; Current Biology; 23; pp. 436-440; Mar. 2013.
Britton et al.; Modulation of postural tremors at the wrist by supramaximal electrical median nerve shocks in ET, PD, and normal subjects mimicking tremor; J Neurology, Neurosurgery, and Psychiatry; 56(10); pp. 1085-1089; Oct. 1993.
Cagnan et al.; Phase dependent modulation of tremor amplitude in essential tremor through thalamic stimulation; Brain; 136(10); pp. 3062-3075; Oct. 2013.
Campero et al.; Peripheral projections of sensory fasicles in the human superificial radial nerve; Brain; 128(Pt 4); pp. 892-895; Apr. 2005.
Chen et al.; A web-based system for home monitoring of patients with Parkinson's disease using wearable sensors; IEEE Trans on Bio-Medical Engineering; 58(3); pp. 831-836; Mar. 2011.
Clair et al.; Postactivation depression and recovery of reflex transmission during repetitive electrical stimulation of the human tibial nerve, Journal of Neurophysiology; vol. 106, No. 1; pp. 184-192; Jul. 2011.
Clar et al.; Skin impedance and moisturization; J. Soc. Cosmet. Chem.; 26; pp. 337-353; 1975; presented at IFSCC Vilith Int'l Congress Cosmetics Quality and Safety in London on Aug. 26-30, 1974.
Constandinou et al.; A Partial-Current-Steering Biphasic Stimulation Driver for Vestibular Prostheses; IEEE Trans on Biomedical Circuits and Systems; 2(2); pp. 106-113; Jun. 2008.
Daneault et al.; Using a smart phone as a standalone platform for detection and monitoring of pathological tremors; Frontiers in Human Neuroscience; vol. 6, article 357; 12 pgs.; Jan. 2012.
Deuschl et at; Consensus statement of the Movement Disorder Society on Tremor. Ad Hoc Scientific Committee., Movement Disorders, vol. 13 Suppl 3, pp. 2-23; (year of pub. sufficiently earlier than effective US filed and any foreign priority date)1998.
Dideriksen et al.; EMG-based characterization of pathological tremor using the iterated Hilbert transform; IEEE transactions on Biomedical Engineering; 58(10); pp. 2911-2921; Oct. 2011.
Dosen et al.: Tremor suppression using electromyography and surface sensory electrical stimulation; Converging Clinical and Engineering Research on Neurorehabilitation; vol. 1 (Siosystems & Biorobotics Series); pp. 539-543; Feb. 2013.
Doucet et al.; Neuromuscular electrical stimulation for skeletal muscle function; The Yale Journal of Biology and Medicine; 85(2); pp. 201-215; Jun. 2012.
Fuentes et al.; Restoration of locomotive function in Parkinson's disease by spinal cord stimulation: mechanistic approach, Eur J Neurosci, vol. 32, pp. 1100-1108; Oct. 2010 (author manuscript; 19 pgs.).
Fuentes et al.; Spinal cord stimulation restores locomotion in animal models of Parkinson's disease; Science; 323; pp. 1578-1582; Mar. 2009.
Gallego et al.; A neuroprothesis for tremor management through the control of muscle co-contraction; Journal of Neuroengineering and Rehabilitation; vol. 10; 36; (13 pgs); Apr. 2013.
Gallego et al; A soft wearable robot for tremor assessment and suppression; 2011 IEEE International Conference on Robotics and Automation; Shanghai International Conference Center; pp. 2249-2254; May 9-13, 2011.
Gallego et al.; Real-time estimation of pathological tremor parameters from gyroscope data.; Sensors; 10(3); pp. 2129-2149; Mar. 2010.
Gao; Analysis of amplitude and frequency variations of essential and Parkinsonian tremors; Medical & Biological Engineering & Computing; 42(3); pp. 345-349; May 2004.
Garcia-Rill, E., et al. "Arousal, motor control, and Parkinson's disease." Translational neuroscience 6.1 pp. 198-207 (2015).
Giuffridda et al.; Clinically deployable Kinesia technology for automated tremor assessment.; Movement Disorders; 24(5); pp. 723-730; Apr. 2009.
Gracanin et al.; Optimal stimulus parameters for minimum pain in the chronic stimulatin of innervated muscle; Archives of Physical Medicine and Rehabilitation; 56(6); pp. 243-249; Jun. 1975.
Haeri et al.; Modeling the Parkinson's tremor and its treatments; Journal of Theorectical Biology; 236(3); pp. 311-322; Oct. 2005.
Halon En et al.; Contribution of cutaneous and muscle afferent fibres to cortical SEPs following median and radial nerve stimulation in man; Electroenceph. Clin. Neurophysiol.; 71(5); pp. 331-335; Sep.-Oct. 1988.
Hao et al.; Effects of electrical stimulation of cutaneous afferents on corticospinal transmission of tremor signals in patients with Parkinson's disease; 6th International Conference on Neural Engineering; San Diego, CA; pp. 355-358; Nov. 2013.
Hauptmann et al.; External trial deep brain stimulation device for the application of desynchronizing stimulation techniques; Journal of Neural Engineering; 6; 12 pgs.; Oct. 2009.
Heller et al.; Automated setup of functional electrical stimulation for drop foot using a novel 64 channel prototype stimulator and electrode array: Results from a gait-lab based study; Medical Engineering & Physic; 35(1); pp. 74-81; Jan. 2013.
Henry Dreyfuss Associates; The Measure of Man and Woman: Human Factors in Design (Revised Edition); John Wiley & Sons, New York; pp. 10-11 and 22-25; Dec. 2001.
Hernan, Miguel, et al. "Alcohol Consumption and the Incidence of Parkinson's Disease." May 15, 2003. Annals of Neurology. vol. 54. pp. 170•175.
Hua et al.; Posture-related oscillations in human cerebellar thalamus in essential tremor are enabled by voluntary motor circuits; J Neurophysiol; 93(1); pp. 117-127; Jan. 2005.
Inoue, Masahiro, Katsuaki Suganuma, and Hiroshi Ishiguro. "Stretchable human interface using a conductive silicone elastomer containing silver fillers." Consumer Electronics, 2009. ISCE'09. IEEE 13th International Symposium on. IEEE, 2009.
Jacks et al.; Instability in human forearm movements studied with feed-back-controlled electrical stimulation of muscles; Journal of Physiology; 402; pp. 443-461; Aug. 1988.
Jobges et al.; Vibratory proprioceptive stimulation affects Parkinsonian tremor; Parkinsonism & Related Disorders; 8(3); pp. 171-176; Jan. 2002.
Joundi et al.; Rapid tremor frequency assessment with the iPhone accelerometer.; Parkinsonism & Related Disorders; 17(4); pp. 288-290; May 2011.
Kim et al.: Adaptive control of movement for neuromuscular stimulation-assisted therapy in a rodent model; IEEE Trans on Biomedical Engineering,; 56(2); pp. 452-461; Feb. 2009.
Krauss et al.; Chronic spinal cord stimulation in medically intractable orthostatic tremor; J Neurol Neurosurg Psychiatry; 77(9); pp. 1013-1016; Sep. 2006.
Kuhn et al.; Array electrode design for transcutaneous electrical stimulation a simulation study; Medical Engineering & Physics; 31 (8); pp. 945-951; Oct. 2009.
Kuhn et al.; The Influence of Electrode Size on Selectivity and Comfort in Transcutaneous Electrical Stimulation of the Forearm; Neural Systems and Rehabilitation Engineering, IEEE Transactions on; 18(3); pp. 255-262; Jun. 2010.
Kunz, Patrik, et al. "5 kHz transcranial alternating current stimulation: lack of cortical excitability changes when grouped in a theta burst pattern." Frontiers in Human Neuroscience 10 (2016): 683.

(56) References Cited

OTHER PUBLICATIONS

Lagerquist et al.: Influence of stimulus pulse width on M-waves, H-reflexes, and torque during tetanic low-intensity neuromuscular stimulation, Muscle & Nerve, 42(6), pp. 886-893; Dec. 2010.
Laroy et al.; The sensory innervation pattern of the fingers; J. Neurol.; 245 (5); pp. 294-298; May 1998.
Lee et al.; Resetting of tremor by mechanical perturbations: A comparison of essential tremor and parkinsonian tremor; Annals of Nuerology; 10(6); pp. 523-531; Dec. 1981.
Legon et al.; Pulsed ultrasound differentially stimulates somatosensory circuits in humans as indicated by EEG and fMRI; PLoS ONE; 7(12); e51177; 14 pgs.; Dec. 2012.
Lourenco et al.; Effects produced in human arm and forearm motoneurones after electrical stimulation of ulnar and median nerves at wrist level; Experimental Brain Research; 178(2); pp. 267-284; Apr. 2007.
Malek et al.; The utility of electromyography and mechanomyography for assessing neuromuscular function: a noninvasive approach; Phys Med Rehabil in N Am; 23(1); pp. 23-32; Feb. 2012.
Mamorita et al.; Development of a system for measurement and analysis of tremor using a three-axis accelerometer; Methods Inf Med; 48(6); pp. 589-594; epub Nov. 2009.
Maneski et al.; Electrical Stimulation for suppression of pathological tremor; Med Biol Eng Comput; 49(10); pp. 1187-1193; Oct. 2011.
Marsden et al.; Coherence between cerebellar thalamus, cortex and muscle in man; Brain; 123; pp. 1459-1470; Jul. 2000.
Marshall, Ryan, et al. "Bioelectrical stimulation for the reduction of inflammation in inflammatory bowel disease." Clinical Medicine Insights: Gastroenterology 8 (2015): CGast-S31779.
McAuley et al.; Physiological and pathological tremors and rhythmic central motor control; Brain; 123(Pt 8); pp. 1545-1567; Aug. 2000.
McIntyre et al.; Finite element analysis of current-density and electric field generated by metal microelectrodes; Annals of Biomedical Engineering; 29(3); pp. 227-235; Mar. 2001.
Meekins et al.; American Association of Neuromuscular & Electrodiagnostic Medicine evidenced-based review: use of surface electromyography in the diagnosis and study of neuromuscular disorders; Muscle Nerve 38(4); pp. 1219-1224; Oct. 2008.
Miller et al.; Multiplexed microneedle-based biosensor array for characterization of metabolic acidosis; Talanta; 88; pp. 739-742; Jan. 2012 (author manuscript; 13 pgs.).
Milne et al.; Habituation to repeated in painful and non-painful cutaneous stimuli: A quantitative psychophysical study; Experimental Brain Research; 87(2); pp. 438-444; Nov. 1991.
Mommaerts et al.; Excitation and nerve conduction; in Comprehensive Human Physiology; Springer Berlin Heidelberg; Chap. 13; pp. 283-294; Mar. 1996.
Mones et al.; The response of the tremor of patients with Parkinsonism to peripheral nerve stimulation; J Neurology, Neurosurgery, and Psychiatry; 32(6); pp. 512-518; Dec. 1969.
Morgante et al.: How many parkinsonian patients are suitable candidates for deep brain stimulation of subthalamic nucleus?; Results of a Questionnaire, Partkinsonism Relat Disord; 13; pp. 528-531; Dec. 2007.
Munhoz et al; Acute effect of transcutaneous electrical nerve stimulation on tremor; Movement Disorders; 18(2); pp. 191-194; Feb. 2003.
Nardone et al.; Influences of transcutaneous electrical stimulation of cutaneous and mixed nerves on subcortical somatosensory evoked potentials; Electroenceph. Clin. Neurophysiol.; 74(1); pp. 24-35; Jan.-Feb. 1989.
PCT Search Report and Written Opinion in PCT Application No. PCT/US2017/040920 dated Oct. 24, 2017 in 21 pages.
Perez et al.; Patterned Sensory Stimulation Induces Plasticity in Reciprocal la Inhibition in Humans; The Journal of Neuroscience; 23(6); pp. 2014-2018; Mar. 2003.
Perlmutter et al.; Deep brain stimulation; Ann Rev Neurosci; 29; pp. 229-257; Jul. 2006.
Popović□Bijelić, Ana, et al. "Multi□field surface electrode for selective electrical stimulation." Artificial organs 29.6 (2005): 448-452.
Prochazka et al.; Attenuation of pathological tremors by functional electrical stimulation I: Method; Annals of Biomedical Engineering; 20(2); pp. 205-224; Mar. 1992.
Pulliam et al.; Continuous in-home monitoring of essential tremor; Parkinsonism Relat Disord; 20(1); pp. 37-40; Jan. 2014.
Quattrini et al.; Understanding the impact of painful diabetic neuropathy; Diabetes/Metabolism Research and Reviews; 19, Suppl. 1; pp. S2-S8; Jan.-Feb. 2003.
Rocon et al.; Design and validation of a rehabilitation robotic exoskeleton for tremor assessment and suppression; IEEE Trans Neural Sys and Rehab Eng.; 15(3); pp. 367-378; Sep. 2007.
Silverstone et al.; Non-Invasive Neurostimulation in the Control of Familial Essential Tremor Using the Synaptic Neuromodulator; Conference Proceedings, International Functional Electrical Stimulation Society (IFES); Ed. Paul Meadows; 3 pgs.; May 1999.
Singer et al.; The effect of EMG triggered electrical stimulation plus task practice on arm function in chronic stroke patients with moderate-severe arm deficits; Restor Neurol Neurosci; 31(6); pp. 681-691; Oct. 2013.
Takanashi et al.; A functional MRI study of somatotopic representation of somatosensory stimulation in the cerebellum; Neuroradiology; 45(3); pp. 149-152; Mar. 2003.
Tass et al.; Coordinated reset has sustained aftereffects in Parkinsonian monkeys; Ann Neurol; 72(5); pp. 816-820; Nov. 2012.
Tass et al.; Counteracting tinnitus by acoustic coordinated reset neuromodulation; Restorative neurology and Neuroscience; 30(2); pp. 137-159; Apr. 2012.
Tass; A Model of desynchronizing deep brain stimulation with a demand-controlled coordinated reset of neural subpopulations; Bioi Cybern; 89(2); pp. 81-88; Aug. 2003.
Toloso et al.; Essential tremor: treatment with propranolol; Neurology; 25(11); pp. 1041; Nov. 1975.
Treager; Interpretation of skin impedance measurements; Nature; 205; pp. 600-601; Feb. 1965.
Valente; Novel methods and circuits for field shaping in deep brain stimulation; Doctoral thesis, UCL (University College London); 222 pgs.; 2011.
Von Lewinski et al.; Efficacy of EMG-triggered electrical arm stimulation in chronic hemiparetic stroke patients; Restor Neurol Neurosci; 27(3); pp. 189-197; Jun. 2009.
Wardman et al.; Subcortical, and cerebellar activation evoked by selective stimulation of muscle and cataneous afferents: an fMRI study; Physiol. Rep.; 2(4); pp. 1-16; Apr. 2014.
Wiestler et al.; Integration of sensory and motor representations of single fingers in the human; J. Neurophysiol.; 105(6); pp. 3042-3053; Jun. 2011.
Woldag et al.; Evidence-based physiotherapeutic concepts for improving arm and hand function in stroke patients R A review; J Neurol; 249(5); pp. 518-528; May 2002.
Woolf et al.; Peripheral nerve injury triggers central sprouting of myelinated afferents; Nature; 355(6355); pp. 75-78; Jan. 1992.
Yeh, Kuei-Lin, Po-Yu Fong, and Ying-Zu Huang. "Intensity sensitive modulation effect of theta burst form of median nerve stimulation on the monosynaptic spinal reflex." Neural plasticity 2015 (2015) in 8 pages.
Yilmaz, Ozlem O., et al. "Efficacy of EMG-biofeedback in knee osteoarthritis." Rheumatology international 30.7 (2010): 887-892.
Zhang et al.; Neural oscillator based control for pathological tremor suppression via functional electrical stimulation; Control Engineering Practice; 19(1); pp. 74-88; Jan. 2011.
Zwarts et al.; Multichannel surface EMG: basic aspects and clinical utility; Muscle Nerve; 28(1); pp. 1-17; Jul. 2003.
Choi, Jong Bo, et al. "Analysis of heart rate variability in female patients with overactive bladder." Urology 65.6 (2005): 1109-1112.
Hubeaux, Katelyne, et al. "Autonomic nervous system activity during bladder filling assessed by heart rate variability analysis in women with idiopathic overactive bladder syndrome or stress urinary incontinence." The Journal of urology 178.6 (2007): 2483-2487.

(56) References Cited

OTHER PUBLICATIONS

Hubeaux, Katelyne, et al. "Evidence for autonomic nervous system dysfunction in females with idiopathic overactive bladder syndrome." Neurourology and urodynamics 30.8 (2011): 1467-1472.

Liao, Wen-Chien, and Fu-Shan Jaw. "A noninvasive evaluation of autonomic nervous system dysfunction in women with an overactive bladder." International Journal of Gynecology & Obstetrics 110.1 (2010): 12-17.

Mehnert, Ulrich, et al. "Heart rate variability: an objective measure of autonomic activity and bladder sensations during urodynamics." Neurourology and urodynamics 28.4 (2009): 313-319.

* cited by examiner pgpw=positive-going pulse width
ngpw=negative-going pulse width
pgsa=positive-going stimulation amplitude
ngsa=negative-going stimulation amplitude pgpw=positive-going pulse width
ngpw=negative-going pulse width
pgsa=positive-going stimulation amplitude
ngsa=negative-going stimulation amplitude cross sections pillow shaped profile top view rounded corners for a square

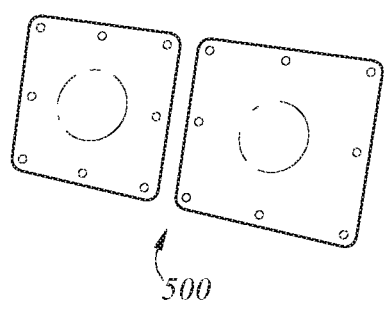
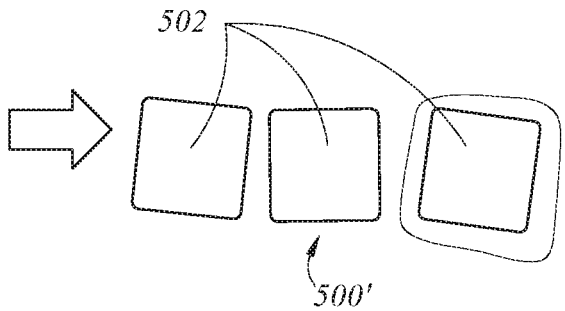
FIG. 13A        FIG. 13B
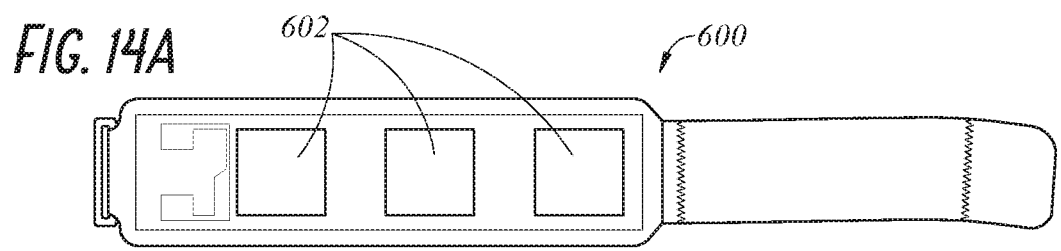
FIG. 14A
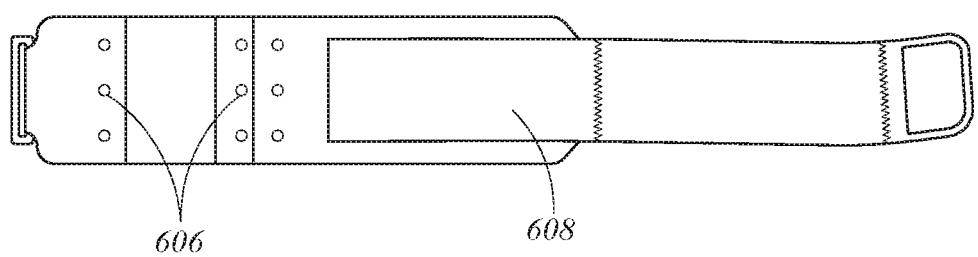
FIG. 14B

DRY ELECTRODES FOR TRANSCUTANEOUS NERVE STIMULATION

INCORPORATION BY REFERENCE

This application claims the benefit as a continuation of PCT App. No. PCT/US2017/040920 filed on Jul. 6, 2017, which in turn claims the benefit as a nonprovisional application under 35 U.S.C. § 119(e) of U.S. Prov. App. No. 62/360,265, filed on Jul. 8, 2016, and U.S. Prov. App. No. 62/432,519, filed on Dec. 9, 2016. Each of the foregoing applications is hereby incorporated by reference in their entireties. This application also incorporates by reference in their entireties International Application Number PCT/US2015/033809, filed Jun. 10, 2016; U.S. Pat. No. 9,452,287 issued on Sep. 27, 2016; International Application No. PCT/US2016/37080, filed Jun. 10, 2016; International Patent Application No. PCT/US2015/033809, filed Jun. 2, 2015; U.S. Application No. 62/173,894, filed Jun. 10, 2015; International Patent Application No. PCT/US2016/045038 filed on Aug. 1, 2016; International Patent Application No. PCT/US2016/053513 filed on Sep. 23, 2016; and International Patent Application No. PCT/US2017/014431 filed on Jan. 20, 2017.

BACKGROUND

Field of the Invention

Embodiments of the invention relate generally to systems, devices, and methods for stimulating nerves, and more specifically relate to system, devices, and methods for electrically stimulating peripheral nerve(s) to treat various disorders.

Description of the Related Art

Electrical stimulation can be delivered transcutaneously via transcutaneous electrical nerve stimulation (TENS) systems to stimulate peripheral nerves, such as the median, radial, or ulnar nerves in the upper extremities, or the tibial, saphenous, or peroneal nerve in the lower extremities, or the vagus nerve in the ear or neck. Electrical stimulation of these nerves has been shown to provide therapeutic benefit across a variety of diseases, including but not limited to movement disorders (including but not limited to essential tremor, Parkinson's tremor, orthostatic tremor, and multiple sclerosis), urological disorders, gastrointestinal disorders, and cardiac diseases. A number of conditions, such as tremors, can be treated through some form of transcutaneous peripheral nerve stimulation.

Other disorders can also be treated through peripheral nerve neurostimulation. For example, stimulation of the sacral and/or tibial nerve has been shown to improve symptoms of overactive bladder and urinary incontinence, and stimulation of the vagus nerve has been shown to improve symptoms of hypertension and cardiac dysrhythmias.

Some previously described transcutaneous stimulators describe using multiple electrodes, such as at least three electrodes, in order to stimulate multiple peripheral nerves, such as various combinations of the median, radial, and ulnar nerves in the arm. For example, each nerve can be stimulated with a dedicated electrode pair, which would require twice the number of electrodes compared to the number of nerves to be stimulated. For example, to stimulate both radial and median nerves would require 4 electrodes. Circumferential electrodes with a dedicated return electrode and individual electrodes placed over each nerve could also be used. For example, three circumferentially spaced electrodes can also be used to stimulate those two nerves, thereby reducing the number of electrodes by one, to three electrodes.

It would be desirable to further reduce the number of electrodes required to stimulate multiple nerves in order to reduce the size and cost of the stimulation surface or disposable.

Most commercially available devices that deliver electrical stimulation transcutaneously utilize a hydrogel electrode to provide a reliably comfortable stimulation to the wearer (or are a dry electrode with a conductive gel applied). Hydrogel electrodes have two beneficial properties that provide uniform current distribution across the surface of the electrode, which improves comfort of stimulation: (1) a water or gel based electrode surface allows for preferable conduction properties electrode, and (2) adhesion to the skin provides high skin conformance. This conformance and integrity of the contact can be important in some cases for comfortable electrical stimulation of sensory nerves below the skin surface. However, the sticky hydrogel electrode can potentially provide challenges in usability for the wearer, as the hydrogel material does not allow movement (e.g., adjustment of a body-worn device), can be challenging to remove and apply (e.g., can lose its adhesive properties), can easily and quickly become dirty or degrade, especially in real-world environments, and can cause skin irritation. Thus, hydrogel electrodes may not be desirable for repeated, all day wear. For these reasons, it can be advantageous in some embodiments to develop a dry skin interface between the electrode and skin known as a "dry electrode" to deliver electrical stimulation, particularly for body-worn stimulation devices intended for long-term, repeated wear. It can also be challenging to develop a dry electrode material, because loading agents that allow for conduction also tend to increase material stiffness, which reduces conformance and leads to discomfort at the skin interface. Furthermore, it can in at least some cases be very difficult to manufacture dry electrodes which provide uniform field at the skin electrode interface.

SUMMARY

The present invention relates generally to systems, devices, and methods for stimulating nerves, and more specifically relate to system, devices, and methods for electrically stimulating peripheral nerve(s) to treat various disorders.

In some embodiments, a system for noninvasively stimulating at least two peripheral nerves of a patient is provided. The system can include a first electrode and a second electrode. The first electrode can be placed against the patient's skin proximate a first peripheral nerve and the second electrode can be placed against the patient's skin proximate a second peripheral nerve. The system further includes a stimulator configured to generate an electrical stimulation, the stimulator in electrical communication with the first electrode and the second electrode. The system further includes a controller configured to control the generation of the electrical stimulation by the stimulator. The electrical stimulation can include a first stimulation waveform that is charge balanced and can have an excitatory phase and a charge balance phase where the first electrode serves as an excitatory electrode (e.g., as an anode) and the second electrode serves as a charge balance electrode (e.g., as a cathode). The system can include exactly the same number of electrodes as the number of nerves configured to be stimulated.

In some embodiments, the excitatory phase of the first stimulation waveform has the same amplitude and duration as the charge balance phase of the first stimulation waveform. The first stimulation waveform is configured to stimulate the first peripheral nerve and the second peripheral nerve simultaneously.

In some embodiments, the excitatory phase of the first stimulation waveform has a greater amplitude and a shorter duration than the charge balance phase of the first stimulation waveform. The first stimulation waveform is configured to stimulate the first peripheral nerve and not stimulate the second peripheral nerve. The excitatory phase can have either a positive or negative-going charge with the charge balance phase have a corresponding opposite polarity.

In some embodiments, the system includes no more than two electrodes.

In some embodiments, the electrical stimulation generated by the controller further includes a second stimulation waveform that is charge balanced and includes an excitatory phase and a charge balance phase. The polarity of the first electrode and the second electrode can be switched between the first stimulation waveform and the second stimulation waveform such that in the second stimulation waveform the first electrode serves as the charge balance electrode and the second electrode serves as excitatory electrode. The excitatory phase of the second stimulation waveform has a greater amplitude and a shorter duration than the charge balance phase of the second stimulation waveform. The second stimulation waveform is configured to stimulate the second peripheral nerve and not stimulate the first peripheral nerve.

In some embodiments, the first electrode and second electrode are disposed on a wearable band.

In some embodiments, the first electrode and the second electrode are spaced farther apart than the spacing of the first nerve and the second nerve such that when placed on skin, the first electrode and the second electrode flank the first nerve and the second nerve.

In some embodiments, the first electrode and the second electrode are spaced apart less than the spacing of the first nerve and the second nerve such that when placed on skin, the first nerve and the second nerve flank the first electrode and the second electrode.

In some embodiments, the amplitude of the excitatory phase of the first stimulation waveform is about or at least about 2, 3, 4, 5, 6, 7, 8, 9, 10, 15, 20, or more times greater than the amplitude of the charge balance phase of the first stimulation waveform, or within a range incorporating any two of the aforementioned values.

In some embodiments, the amplitude of the excitatory phase of the first stimulation waveform is less than about 20, 15, 10, 9, 8, 7, 6, 5, 4, 3, 2 times or less greater than the amplitude of the charge balance phase of the first stimulation waveform.

In some embodiments, the first electrode is spaced apart from the second electrode based on the spacing between the first nerve and the second nerve.

In some embodiments, the first electrode is spaced apart from the second electrode based additionally on the depths of the first nerve and second nerve.

In some embodiments, the number of electrodes equals the number of nerves to be stimulated.

In some embodiments, the system further includes one or more additional electrodes. Each additional electrode is placed over a peripheral nerve, and the controller is configured to select one of the electrodes as the excitatory electrode and one of the other electrodes as the charge balance electrode. The selection of the excitatory electrode is based on the peripheral nerve to be stimulated.

In some embodiments, the selection of the charge balance electrode is based in part on the spacing between the excitatory electrode and the charge balance electrode.

In some embodiments, the first electrode and the second electrodes are dry electrodes including a conductive backing layer and a skin contact layer disposed on the conductive backing layer. The skin contact layer includes a polymer, plastic, or rubber material, and a conductive filler material dispersed substantially evenly throughout the polymer, plastic, or rubber material. The skin contact layer has a skin facing surface that is not coated with a hydrogel or liquid.

In some embodiments, the conductive backing layer of the dry electrodes may include a metal foil. The metal foil may be disposed on a flexible polymer substrate. The conductive filler material may include a powder or fine particulate material. The conductive filler material may include metal, carbon, or a mixture thereof. The conductive layer can include a porous material treated with a conductive coating. The skin contact layer may have a Shore hardness between about 10 A to about 100 A. The skin contact layer may have a volume resistivity between about 1 ohm*cm and about 2000 ohm*cm. The measured resistance or conductance at a plurality of points across the skin facing surface of the skin contact layer may have a standard deviation of within about 50% of the average measured resistance or conductance. The skin contacting layer may comprise silicone. The conductive filler material may include silver coated glass bubbles or single wall carbon nanotubes, wherein the homogeneity of the conductive filler material is such that there is less than about a 5% difference in resistivity across the skin contact layer. The conductive filler material may include silver coated glass bubbles. The conductive filler material may include single wall carbon nanotubes. The loading of silver coated glass bubbles may be between about 3% and about 30% of the skin contact layer. The loading of single wall carbon nanotubes may be between about 1% and about 5%. The skin contact layer may have a Shore hardness between about 25 A to about 55 A. The skin contact layer may have a volume resistivity between about 50 ohm*cm and about 1000 ohm*cm.

In some embodiments, a system for noninvasively stimulating at least two peripheral nerves of a patient is provided. The system includes a first electrode and a second electrode, wherein the first electrode is configured to be placed against the patient's skin proximate a first peripheral nerve and the second electrode is configured to be placed against the patient's skin proximate a second peripheral nerve. The system further includes a stimulator configured to generate an electrical stimulation. The stimulator is in electrical communication with the first electrode and the second electrode. The system further includes a controller configured to control the generation of the electrical stimulation by the stimulator. The electrical stimulation includes a first stimulation waveform that is charge balanced and comprises an excitatory phase and a charge balance phase where the first electrode serves as an excitatory electrode and the second electrode serves as a charge balance electrode. The excitatory phase of the first stimulation waveform has a greater amplitude and a shorter duration than the charge balance phase of the first stimulation waveform. The first stimulation waveform is configured to stimulate the first peripheral nerve and not stimulate the second peripheral nerve.

In some embodiments, the system may include no more than two electrodes. The electrical stimulation generated by the controller may further include a second stimulation waveform that is charge balanced and comprises a excitatory phase and a charge balance phase. The polarity of the first electrode and the second electrode may be switched between the first stimulation waveform and the second stimulation waveform such that in the second stimulation waveform the first electrode serves as the charge balance electrode and the second electrode serves as excitatory electrode. The excitatory phase of the second stimulation waveform may have a greater amplitude and a shorter duration than the charge balance phase of the second stimulation waveform. The second stimulation waveform may be configured to stimulate the second peripheral nerve and not stimulate the first peripheral nerve.

In some embodiments, the first electrode and second electrode may be disposed on a wearable band. The first electrode and the second electrode may be spaced farther apart than the spacing of the first nerve and the second nerve such that when placed on skin, the first electrode and the second electrode flank the first nerve and the second nerve. The first electrode and the second electrode may be spaced apart less than the spacing of the first nerve and the second nerve such that when placed on skin, the first nerve and the second nerve flank the first electrode and the second electrode. The amplitude of the excitatory phase of the first stimulation waveform may be at least about 4 times greater than the amplitude of the charge balance phase of the first stimulation waveform. The amplitude of the excitatory phase of the first stimulation waveform may be less than about 10 times greater than the amplitude of the charge balance phase of the first stimulation waveform. The first electrode may be spaced apart from the second electrode based on the spacing between the first nerve and the second nerve. The first electrode may be spaced apart from the second electrode based additionally on the depths of the first nerve and second nerve. The number of electrodes can equal the number of nerves to be stimulated. The system may further include one or more additional electrodes, wherein each additional electrode is placed over a peripheral nerve. The controller can be configured to select one of the electrodes as the excitatory electrode and one of the other electrodes as the charge balance electrode, wherein the selection of the excitatory electrode may be based on the peripheral nerve to be stimulated. The selection of the charge balance electrode may be based in part on the spacing between the excitatory electrode and the charge balance electrode.

In some embodiments, a method for noninvasively stimulating a plurality of peripheral nerves of a patient with exactly one electrode per each peripheral nerve stimulated is disclosed. The method includes positioning a first electrode against the patient's skin proximate a first peripheral nerve; positioning a second electrode against the patient's skin proximate a second peripheral nerve; and delivering a first electrical stimulation through the first electrode to stimulate the first peripheral nerve. The first electrical stimulation includes a first stimulation waveform that is charge balanced and comprises an excitatory phase and a charge balance phase. During the first electrical stimulation, the first electrode serves as an excitatory electrode and the second electrode serves as a charge balance electrode. The excitatory phase of the first stimulation waveform has a greater amplitude and a shorter duration than the charge balance phase of the first stimulation waveform. The first stimulation waveform is configured to stimulate the first peripheral nerve and not stimulate the second peripheral nerve.

In some embodiments, the method further includes delivering a second electrical stimulation through the second electrode to stimulate the second peripheral nerve. The second electrical stimulation includes a second stimulation waveform that is charge balanced and includes an excitatory phase and a charge balance phase. During the second electrical stimulation, the second electrode serves as an excitatory electrode and the first electrode serves as a charge balance electrode. The excitatory phase of the second stimulation waveform has a greater amplitude and a shorter duration than the charge balance phase of the second stimulation waveform. The second stimulation waveform is configured to stimulate the second peripheral nerve and not stimulate the first peripheral nerve.

In some embodiments, the first electrode and second electrode may be disposed on a wearable band. The first electrode and the second electrode may be spaced farther apart than the spacing of the first nerve and the second nerve such that when placed on skin, the first electrode and the second electrode flank the first nerve and the second nerve. The first electrode and the second electrode may be spaced apart less than the spacing of the first nerve and the second nerve such that when placed on skin, the first nerve and the second nerve flank the first electrode and the second electrode. The amplitude of the excitatory phase of the first stimulation waveform may be at least about 4 times greater than the amplitude of the charge balance phase of the first stimulation waveform. The amplitude of the excitatory phase of the first stimulation waveform may be less than about 10 times greater than the amplitude of the charge balance phase of the first stimulation waveform. The first electrode may be spaced apart from the second electrode based on the spacing between the first nerve and the second nerve. The first electrode may be spaced apart from the second electrode based additionally on the depths of the first nerve and second nerve. The first nerve may be selected from the group consisting of the ulnar nerve, the radial nerve, and the median nerve. The second nerve may be selected from the group consisting of the ulnar nerve, the radial nerve, and the median nerve, wherein the second nerve is a different nerve from the first nerve. The first nerve may be selected from the group consisting of the pudendal nerve, pelvic nerve, tibial nerve, medial plantar nerve, lateral plantar nerve, calcaneal nerve, and saphenous nerve. The second nerve may be selected from the group consisting of the pudendal nerve, pelvic nerve, tibial nerve, medial plantar nerve, lateral plantar nerve, calcaneal nerve, and saphenous nerve, wherein the second nerve is a different nerve from the first nerve.

In some embodiments, a method for noninvasively stimulating a plurality of peripheral nerves of a patient with exactly one electrode per each peripheral nerve stimulated is provided. The method includes positioning a first electrode against the patient's skin proximate a first peripheral nerve; positioning a second electrode against the patient's skin proximate a second peripheral nerve; and delivering a first electrical stimulation through the first electrode to stimulate the first peripheral nerve. The first electrical stimulation includes a first stimulation waveform that is charge balanced and comprises an excitatory phase and a charge balance phase. During the first electrical stimulation the first electrode serves as an excitatory electrode and the second electrode serves as a charge balance electrode. The first stimulation waveform is configured to stimulate the first peripheral nerve and the second peripheral nerve simultaneously.

In some embodiments, the excitatory phase of the first stimulation waveform may have the same amplitude and duration as the charge balance phase of the first stimulation waveform. The first electrode and second electrode may be disposed on a wearable band. The first electrode and the second electrode may be spaced farther apart than the spacing of the first nerve and the second nerve such that when placed on skin, the first electrode and the second electrode flank the first nerve and the second nerve. The first electrode and the second electrode may be spaced apart less than the spacing of the first nerve and the second nerve such that when placed on skin, the first nerve and the second nerve flank the first electrode and the second electrode. The first electrode may be spaced apart from the second electrode based on the spacing between the first nerve and the second nerve. The first electrode may be spaced apart from the second electrode based additionally on the depths of the first nerve and second nerve. The first nerve may be selected from the group consisting of the ulnar nerve, the radial nerve, and the median nerve. The second nerve may be selected from the group consisting of the ulnar nerve, the radial nerve, and the median nerve, wherein the second nerve is a different nerve from the first nerve. The first nerve may be selected from the group consisting of the pudendal nerve, pelvic nerve, tibial nerve, medial plantar nerve, lateral plantar nerve, calcaneal nerve, and saphenous nerve. The second nerve may be selected from the group consisting of the pudendal nerve, pelvic nerve, tibial nerve, medial plantar nerve, lateral plantar nerve, calcaneal nerve, and saphenous nerve, wherein the second nerve is a different nerve from the first nerve.

In some embodiments, a system for noninvasively stimulating at least two peripheral nerves of a patient is provided. The system includes a first electrode and a second electrode, wherein the first electrode is configured to be placed against the patient's skin proximate a first peripheral nerve and the second electrode is configured to be placed against the patient's skin proximate a second peripheral nerve. The system further includes a stimulator configured to generate an electrical stimulation. The stimulator is in electrical communication with the first electrode and the second electrode. The system further includes a controller configured to control the generation of the electrical stimulation by the stimulator. The electrical stimulation includes a first stimulation waveform that is charge balanced and comprises an excitatory phase and a charge balance phase. The first electrode serves as an excitatory electrode and the second electrode serves as a charge balance electrode. The system comprises exactly the same number of electrodes as the number of nerves configured to be stimulated.

In some embodiments, the excitatory phase of the first stimulation waveform may have the same amplitude and duration as the charge balance phase of the first stimulation waveform. The first stimulation waveform may be configured to stimulate the first peripheral nerve and the second peripheral nerve simultaneously. The excitatory phase of the first stimulation waveform may have a greater amplitude and a shorter duration than the charge balance phase of the first stimulation waveform. The first stimulation waveform may be configured to stimulate the first peripheral nerve and not stimulate the second peripheral nerve.

In some embodiments, the electrical stimulation generated by the controller may further include a second stimulation waveform that is charge balanced and includes an excitatory phase and a charge balance phase. The polarity of the first electrode and the second electrode can be switched between the first stimulation waveform and the second stimulation waveform such that in the second stimulation waveform the first electrode serves as the charge balance electrode and the second electrode serves as excitatory electrode. The excitatory phase of the second stimulation waveform may have a greater amplitude and a shorter duration than the charge balance phase of the second stimulation waveform. The second stimulation waveform may be configured to stimulate the second peripheral nerve and not stimulate the first peripheral nerve.

In some embodiments, the first electrode and second electrode may be disposed on a wearable band. The first electrode and the second electrode may be spaced farther apart than the spacing of the first nerve and the second nerve such that when placed on skin, the first electrode and the second electrode flank the first nerve and the second nerve. The first electrode and the second electrode may be spaced apart less than the spacing of the first nerve and the second nerve such that when placed on skin, the first nerve and the second nerve flank the first electrode and the second electrode. The amplitude of the excitatory phase of the first stimulation waveform may be at least about 4 times greater than the amplitude of the charge balance phase of the first stimulation waveform. The amplitude of the excitatory phase of the first stimulation waveform may be less than about 10 times greater than the amplitude of the charge balance phase of the first stimulation waveform. The first electrode may be spaced apart from the second electrode based on the spacing between the first nerve and the second nerve. The first electrode may be spaced apart from the second electrode based additionally on the depths of the first nerve and second nerve.

In some embodiments, the first electrode and the second electrodes can be dry electrodes including a conductive backing layer and a skin contact layer disposed on the conductive backing layer. The skin contact layer may include a polymer, plastic, or rubber material, and a conductive filler material dispersed substantially evenly throughout the polymer, plastic, or rubber material. The skin contact layer may have a skin facing surface that is not coated with a hydrogel or liquid. The conductive backing layer of the dry electrodes may include a metal foil. The metal foil may be disposed on a flexible polymer substrate. The conductive filler material may include a powder or fine particulate material. The conductive filler material may include metal, carbon, or a mixture thereof. The conductive layer may include a porous material treated with a conductive coating.

In some embodiments, the skin contact layer may have a Shore hardness between about 10 A to about 100 A. The skin contact layer may have a volume resistivity between about 1 ohm*cm and about 2000 ohm*cm. The measured resistance or conductance at a plurality of points across the skin facing surface of the skin contact layer may have a standard deviation of within about 50% of the average measured resistance or conductance. The skin contacting layer may include silicone. The conductive filler material may include silver coated glass bubbles or single wall carbon nanotubes. The homogeneity of the conductive filler material may be such that there is less than about a 5% difference in resistivity across the skin contact layer. The loading of silver coated glass bubbles may be between about 3% and about 30% of the skin contact layer. The loading of single wall carbon nanotubes may be between about 1% and about 5%. In some embodiments, the skin contact layer may have a Shore hardness between about 25 A to about 55 A. The skin contact layer may have a volume resistivity between about 50 ohm*cm and about 1000 ohm*cm.

In some embodiments, a dry electrode for transcutaneous electrical stimulation is provided. The dry electrode includes a conductive backing layer and a skin contact layer disposed on the conductive backing layer. The skin contact layer includes a polymer, plastic, or rubber material, and a conductive filler material dispersed substantially evenly throughout the polymer, plastic, or rubber material. The skin contact layer has a skin facing surface that is not coated with a hydrogel or liquid.

In some embodiments, the conductive backing layer may include a metal foil. The metal foil may be disposed on a flexible polymer substrate. The conductive filler material may include a powder or fine particulate material. The conductive filler material may include metal, carbon, or a mixture thereof. The conductive layer may include a porous material treated with a conductive coating. The skin contact layer may have a Shore hardness between about 10 A to about 100 A. The skin contact layer may have a volume resistivity between about 1 ohm*cm and about 2000 ohm*cm. The measured resistance or conductance at a plurality of points across the skin facing surface of the skin contact layer may have a standard deviation of within about 50% of the average measured resistance or conductance. The skin contacting layer may include silicone.

In some embodiments, a wearable band for an electrical device that can be worn by a person is provided. The band includes a strap configured to be worn around a body part, at least two dry electrodes disposed on the strap, a flexible circuit disposed within the strap, and an electrical connect feature. The dry electrodes include a polymer, plastic, or rubber material, and a conductive filler material dispersed substantially evenly throughout the polymer, plastic, or rubber material. The flexible circuit is in electrical communication with the at least two dry electrodes. The electrical connect feature is in electrical communication with the flex circuit and configured to electrically connect the flex circuit with the electrical device.

In some embodiments, the strap includes an elastic portion configured to apply tension or pressure to the at least two dry electrodes against the skin when the strap is tightened around the body part. The strap may include a hook and loop fastener. The electrical connect feature may be a tab that is an extension of the flex circuit. The electrical device may be an electrical nerve stimulation device. The electrical nerve stimulation device can be programmed to deliver electrical stimulation through the dry electrodes to treat tremor. The polymer, plastic, or rubber material may include silicone.

In some embodiments, a dry electrode for transcutaneous electrical stimulation is provided. The dry electrode includes a conductive backing layer and a skin contact layer disposed on the conductive backing layer. The skin contact layer includes a polymer, plastic, or rubber material, and a conductive filler material dispersed substantially evenly throughout the polymer, plastic, or rubber material. The conductive filler material includes silver coated glass bubbles or single wall carbon nanotubes. The skin contact layer has a skin facing surface that is not coated with a hydrogel or liquid. The dry electrode has a bulk resistivity of between about 50 ohm-cm and about 1,000 ohm-cm. The skin contact layer has a Shore A durometer of between about 30 A and about 50 A. The homogeneity of the conductive filler material is such that there is less than about a 5% difference in resistivity across the skin contact layer.

In some embodiments, the skin contact layer may include silicone. The conductive filler material may include silver coated glass bubbles. The conductive filler material may include single wall carbon nanotubes. The loading of silver coated glass bubbles may be between about 3% and about 30% of the skin contact layer. The loading of single wall carbon nanotubes may be between about 1% and about 5%.

In some embodiments, a method of delivering transcutaneous electrical stimulation to a person is provided. The method includes providing a wearable device comprising at least 2 dry electrodes. The dry electrodes include a conductive backing layer and a skin contact layer. The skin contact layer includes a polymer, plastic, or rubber material and a conductive filler material dispersed substantially evenly throughout the polymer, plastic, or rubber material. The skin contact layer further includes a conductive filler material dispersed substantially evenly throughout the polymer, plastic, or rubber material. The method further includes positioning the skin contact layer of the dry electrodes on desired locations on the skin, wherein the polymer, plastic, or rubber material is in direct contact with the skin, and activating the device. Activation of the device delivers electrical current through the dry electrodes to the desired locations on the skin. The desired locations may be adjacent one or more target nerves.

BRIEF DESCRIPTION OF THE DRAWINGS

A better understanding of the features and advantages of some embodiments of the present invention will be obtained by reference to the following detailed description that sets forth illustrative embodiments, in which the principles of the invention are utilized, and the accompanying drawings of which:

FIGS. 1A-1D show multi-perspective views of the device. FIG. 1E shows a schematic of a housing of the device that contains various electronic components.

FIG. 3A illustrates that if the electrodes are placed along the circumference with a charge-balance electrode, the band width decreases. FIG. 3B illustrates that in line placement increases the size of the wrist banded needed.

FIG. 6A is a diagram showing an embodiment of an excitation scheme to dephase the brain regions receiving sensory input from sites, such as two nerves. FIG. 6B is a diagram showing an embodiment of an excitation scheme to dephase the brain regions receiving sensory input from four sites.

FIG. 12A illustrates a testing device for assessing dry electrodes for consistency and uniformity. FIG. 12B illustrates a device for testing the impedance of a dry electrode configuration.

FIGS. 13A-13B illustrate various non-limiting ways dry electrodes can be attached to a wearable band.

FIGS. 14A-14F illustrate multi-perspective views of an embodiment of a band with dry electrodes that can be attached to or retrofitted to an electrical device, such as a TENS device.

FIG. 17A illustrates a graph showing a reduction in tremor for a patient with a customized stimulation from an embodiment using an array of electrodes. FIG. 17B demonstrates the improvement in a spiral drawn by a patient before stimulation (at left) and after stimulation (at right).

FIG. 18A illustrates examples of an embodiment of a wearable band with two dry electrodes and an adjustable strap. FIGS. 18B-18F are graphs that illustrate that stimulation using the wearable band of FIG. 18A is comfortable to most wearers.

DETAILED DESCRIPTION

Peripheral Nerve Stimulation Devices and Methods

One aspect of the invention, according to some embodiments, is a device and system that provides peripheral nerve stimulation, targeting individual nerves. FIGS. 1A-1E illustrate an embodiment of a device and system 10 that allows customization and optimization of transcutaneous electrical treatment provided to an individual. In particular, the device 10 described is for electrical stimulation of two or more nerves. For example, a two electrode embodiment can be used to stimulate any two of the median, radial, or ulnar nerves in the wrist or fingers for treating tremors. Peripheral nerves in other limbs such as the legs and ankles can also be targeted, as well as peripheral nerves in the torso and back. Targeting those specific nerves while utilizing appropriately customized stimulation can result in more effective therapy (e.g., reduction or prevention of tremor, incontinence or overactive bladder symptoms, arrhythmias, normalization of blood pressure, etc.).

Figure 1A:
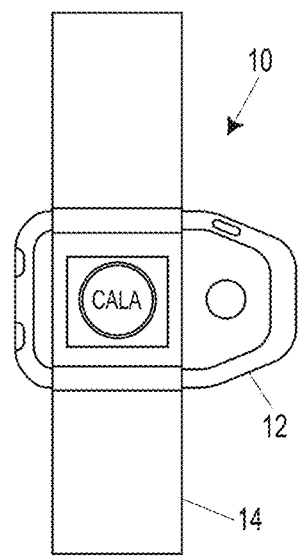
FIGS. 1A-1E illustrate various views of an embodiment of a device and system that provides peripheral nerve stimulation, targeting individual nerves, to reduce tremor.
Figure 1B:
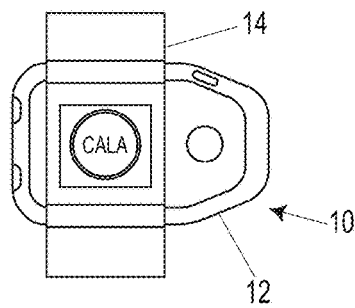
Figure 1D:
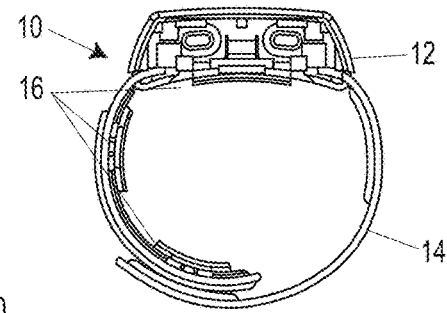
Figure 1C:
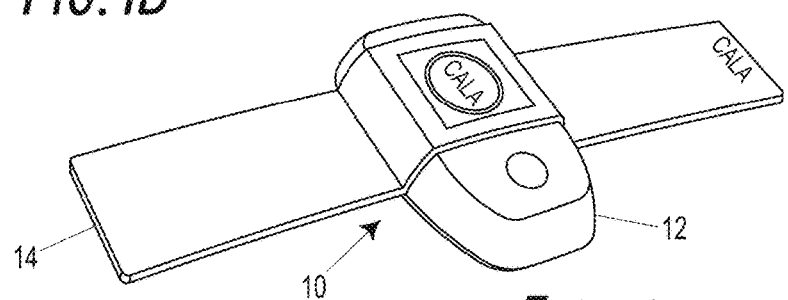
Figure 1E:
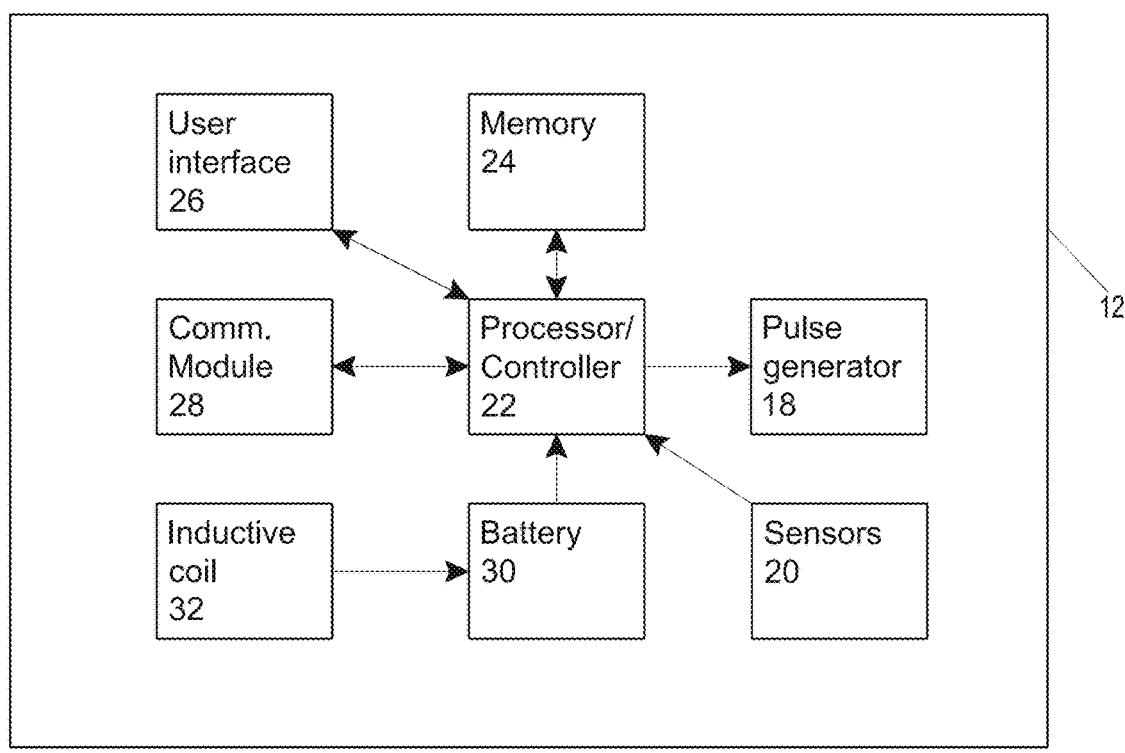

FIGS. 1A-1E illustrate an embodiment of a device and system 10 that provides peripheral nerve stimulation, targeting individual nerves, to reduce tremor. In some embodiments, the device 10 is designed to be worn on the wrist, arm, finger, leg, or ankle and is formed from a housing 12 and a band 14. FIG. 1A illustrates a top view of the device 10 with the band 14 in an unstrapped configuration. FIG. 1B illustrates a top view of the device 10 with the band 14 in a strapped configuration, as if being worn around the wrist of a user. FIG. 1C illustrates a perspective view of the device 10 with the band 14 in an unstrapped configuration. FIG. 1D illustrates a side cross-section of the device 10 with the band 14 in a strapped configuration. FIG. 1E schematically depicts the operative connections of various electronic components that may be housed in the device 10. In some embodiments, electronics are located in a housing 12. The electronics may have sensors to measure motion, heart rate, and/or skin conduction, and/or generate an electrical stimulation waveform. The electronics can include a pulse generator 18 for generating nerve stimulation pulses, a controller 22 for executing instructions, one or more sensors 20 such as an accelerometer and/or gyroscope for monitoring motion, a communication module 28 for transmitting data between the device 10 and an external computer or processor (e.g., wirelessly), a user interface 26 which can include a display and/or buttons for allowing user operation of the device 10 and for presenting information, memory 24 for storing data (e.g., instructions, stimulation protocols, and/or tremor measurements), a battery 30 which may be rechargeable for powering the device 10, and/or an optional inductive coil 30 for wirelessly charging the battery 30. Electrical contacts and/or traces in the band 14 and/or housing 12 can transmit the stimulation waveform from the pulse generator 18 to the electrodes 16, which can be disposable. The locations of the contacts in the band 12 can be arranged such that specific nerves may be targeted, such as the median and radial nerves in the wrist. The housing 12 also can have a digital display screen to provide feedback about the stimulation, measured data, and history to the wearer of the device 10.

In some embodiments, the treatment device 10 is a wearable device including 1) an electronics box or housing 12 containing the stimulator or pulse generator 18, sensors 20, and other associated electronics, 2) a band 14 to hold all the components together and securely fasten the device around the wrist or other body part of an individual, and 3) a plurality of electrodes 16 (e.g., two electrodes, three electrodes, etc.) positioned on the inner surface of the band 14.

Circumferentially Spaced Electrodes

Figure 2A:
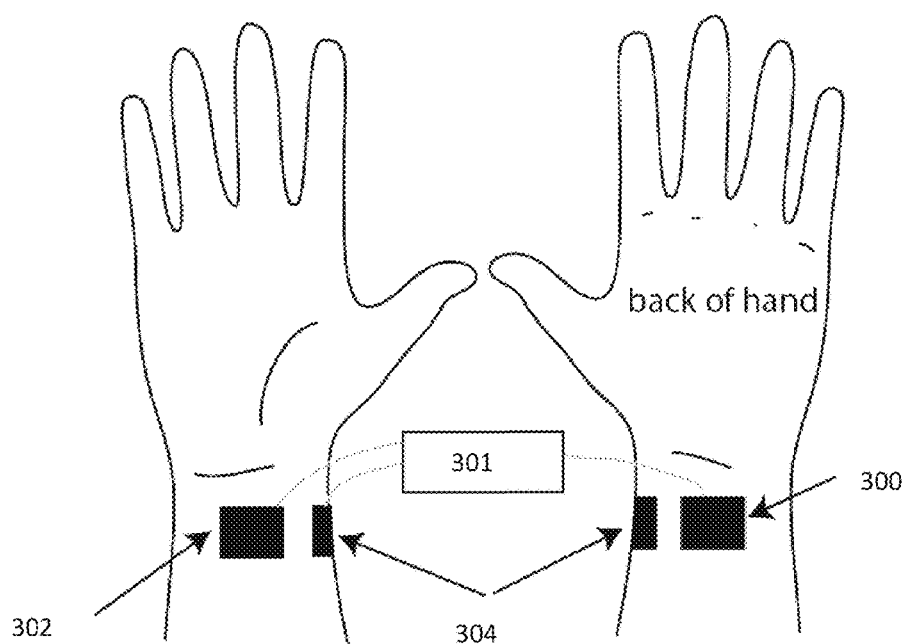
FIGS. 2A-2C illustrate various embodiments of electrodes on a wrist, including a charge-balance electrode on the back of the wrist to reduce the number of electrodes needed to stimulate multiple nerves and electrodes positioned on the circumference of the wrist to selectively stimulate the nerves targeted for excitation.
Figure 2B:
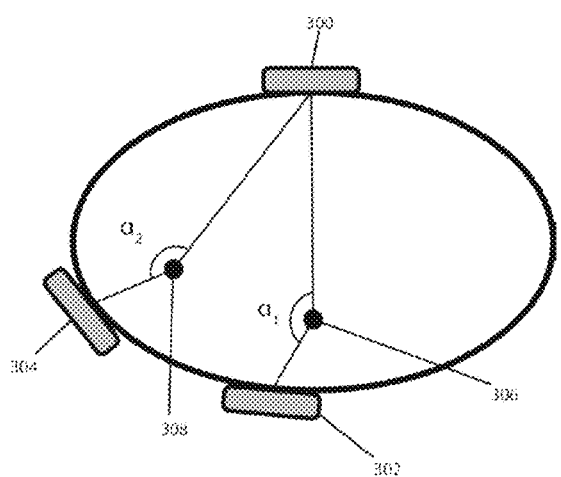
Figure 2C:
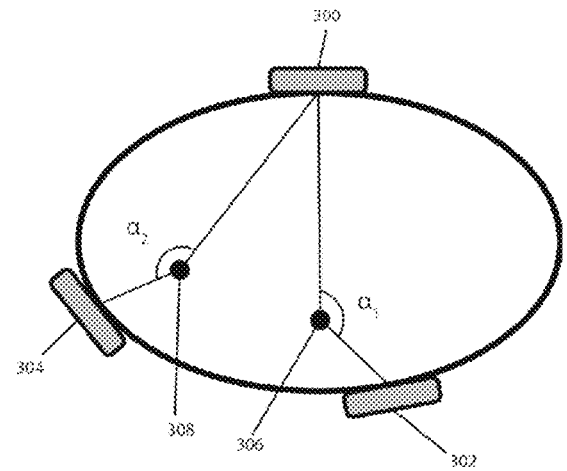

One aspect of the device, as schematically illustrated in FIGS. 2A-2C, is the use of only three electrodes to electrically stimulate two nerves (e.g., median and radial), with an electrode 302, 304 placed on the skin over or proximate to each one of the two nerves 306, 308 and a third charge balance electrode 300 placed on an opposite side of the body part (e.g., wrist) as the two nerves 306, 308. FIG. 2A shows the dorsal side (left) and ventral side (right) of a user's wrist and illustrates an example of the placement of the three electrodes 300, 302, 304 on the user's wrist for targeting two nerves. The three electrodes 300, 302, 304 may all be operatively connected to a single controller 301, as schematically illustrated in FIG. 2A, for regulating the targeted stimulation of the nerves. In some embodiments, the third electrode 300 (e.g., a charge balance electrode) can be placed approximately on the longitudinal midline of the dorsal side of the arm or wrist. In some embodiments, the first electrode 302 can be placed approximately on the longitudinal midline of the ventral side of the arm or wrist to target the median nerve. In some embodiments, the second electrode 304 can be placed in between the charge balance electrode 300 and the ventrally placed electrode 302 to target the radial nerve. In some embodiments, yet another electrode (not shown) can be placed to target the ulnar nerve or an electrode targeting the ulnar nerve can replace either the first electrode 302 targeting the median nerve 306 or the second electrode 304 targeting the radial nerve 308.

FIGS. 2B and 2C illustrate the positions of the charge balance electrode 300, the ventrally placed electrode 302, and the radial electrode 304 in relation to the median nerve 206 and the radial nerve 208 in a distal-looking transverse cross-sectional plane of the patient's wrist or arm. The electrodes 200, 202, 204 are positioned such that in a projection into the transverse cross-sectional plane of the arm or wrist there is a 90 degree to 180 degree angle, $\alpha 1$, between a line connecting the median nerve 306 and the center of the charge balance electrode 300 and a line connecting the median nerve 306 and the center of the ventrally placed electrode 303, and there is a 90 degree to 180 degree angle, $\alpha 2$, between a line connecting the radial nerve 308 and the charge balance electrode 300 and a line connecting the radial nerve 308 and the radial electrode 304. The angles $\alpha 1$ and $\alpha 2$ may each be measured in either a counter-clockwise direction (as $\alpha 1$ is shown in FIG. 2B) or in a clockwise direction (as $\alpha 1$ is shown in FIG. 2C). More generally, the electrodes 300, 302, 304 can be spaced apart by a predetermined distance such that when the electrodes 300, 302, 304 are positioned circumferentially around a patient's wrist, one of the angles formed between each electrode pair and its target nerve is between about 90 degrees and 180 degrees. Such an orientation results in each electrode of the electrode pair being placed generally on opposite sides of the target nerve. In other words, the target nerve is positioned approximately between the electrode pair.

Figure 3A:
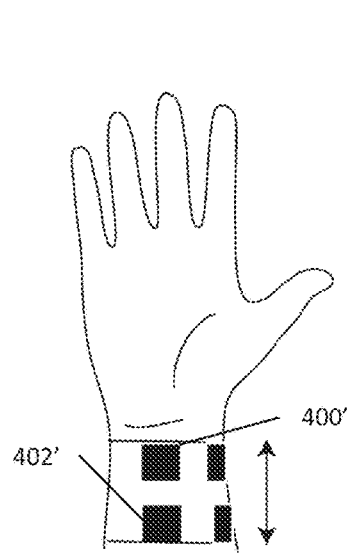
FIGS. 3A and 3B illustrate how in some embodiments the band width can vary depending on how the electrodes are arranged.
Figure 3B:
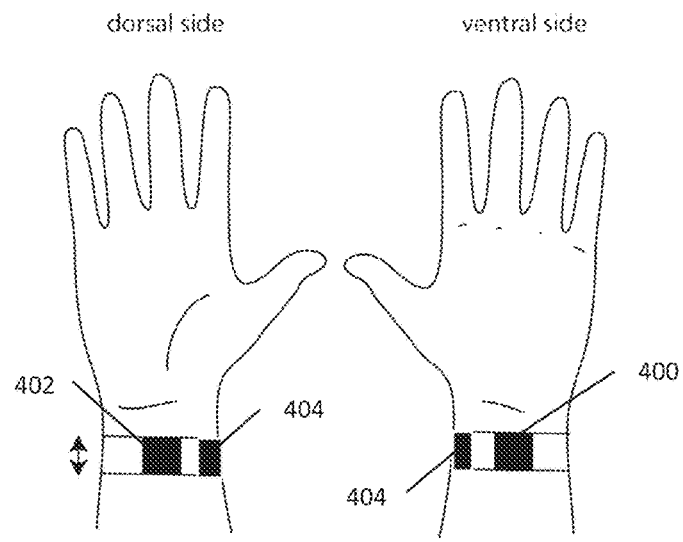

FIG. 3A schematically illustrates the placement of three electrodes 400, 402, 404 for targeted stimulation of two nerves, as described above. FIG. 3B schematically illustrates the traditional placement of two electrodes 400', 402' for targeting each of the same two nerves for a total of four electrodes. As shown in comparison of FIGS. 3A and 3B, three electrodes 400, 402, 404 placed circumferentially around the wrist allow: (1) a reduced band width compared to a typical arrangement where the two electrodes 400', 402' are longitudinally placed along the same nerve, and (2) targeting deeper into the tissue by having the pair of electrodes positioned across from each other to target each nerve compared to a typical arrangement where the two electrodes 400', 402' are positioned on the same side of the arm relative to the targeted nerve. Although the embodiments have been described with reference to three electrodes for the stimulation of two nerves, it is understood that alternative embodiments can utilize two electrodes to stimulate a single nerve, where the two electrodes can have a fixed spacing to allow the electrodes to stimulate the nerve from opposing sides of the nerve. Similarly, other embodiments can utilize more than three electrodes. For instance, an additional electrode can be added to target the ulnar nerve. In some embodiments, five or more electrodes may be used to target four or more nerves. In addition, different combination of electrodes can be used to target one or more nerves from the group of the median, radial, and ulnar nerves.

Mapping the nerves of a number of individuals with different wrist sizes was performed by selectively stimulating circumferential locations on the wrist and verifying where the user feels paresthesia in order to identify the median, radial, and ulnar nerve. The mapping showed variability in nerve location relative to wrist size, as well as high individual variability in physiology. Individual nerves can be targeted with electrodes positioned at the correct location, such as the positions shown in FIG. 2A, or by using an array of multiple electrodes allowing selection of electrodes which target those individual nerves, as discussed elsewhere herein.

N Electrode Stimulator to Stimulate N Nerves

In some embodiments, a stimulator with N electrodes (e.g., where N is an integer greater than 1, e.g., 2 or at least 2 electrodes) can be used to stimulate exactly N nerves (e.g., where N is an integer greater than 1, e.g., 2 or at least 2 electrodes) either simultaneously or in an alternating pattern to treat various disorders such as, for example, tremor, overactive bladder, hypertension, arrythmias, and other conditions. For example, in some embodiments, two nerves, such as the median and radial nerves, can be stimulated using exactly two electrodes, rather than the three or more electrodes as described above and as described in International Application Number PCT/US2015/033809 (International Publication Number WO2015/187712) and U.S. patent application Ser. No. 14/805,385 (U.S. Application Publication No. 2015/0321000), which are each incorporated by reference in their entireties. In other embodiments, exactly 3 nerves can be stimulated by exactly 3 electrodes, exactly 4 nerves can be stimulated by exactly 4 electrodes, etc. Reducing the number of electrodes to be the exactly the same as the number of nerves to be stimulated (e.g., two electrodes to stimulate two nerves) can reduce both manufacturing costs and electrode installation time while increasing the durability and/or robustness of the device, which in some embodiments may need to be utilized on a regular basis, such as daily. There can also be an improvement in comfort because there are only, e.g., two contact points instead of three for stimulating two distinct nerves. The reduced number of electrodes also could allow integration with other wearable devices (e.g., a smart watch display) by not requiring a third electrode under the watch face on the dorsal side of the wrist. Furthermore, in some embodiments, configurations with a lower number of electrodes required (e.g., exactly two electrodes corresponding to exactly two nerves) can employ unique stimulation patterns/waveforms that stimulate a first nerve but not a second nerve.

Figure 4A:
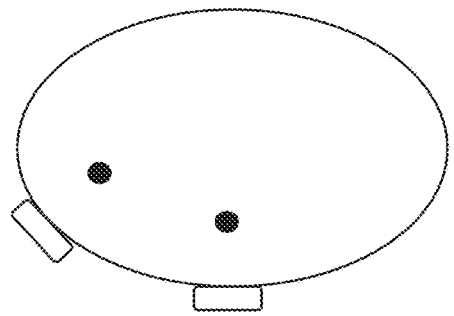
FIGS. 4A-4D illustrate various two electrode placements that can be used to independently stimulate two nerves.
Figure 4B:
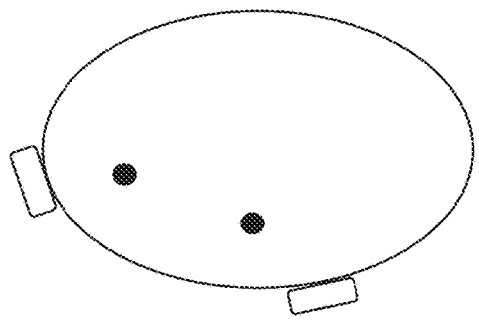
Figure 4C:
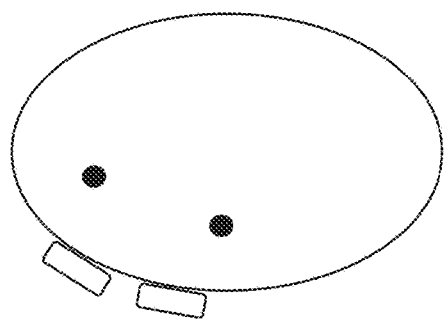
Figure 4D:
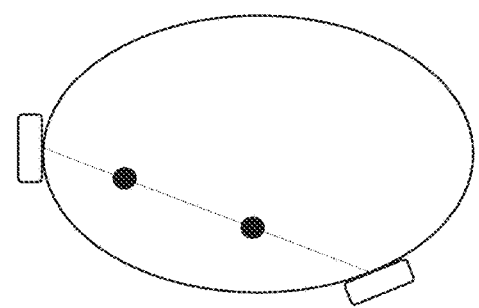

In some embodiments, the two electrodes, e.g., exactly and no more than two electrodes may be placed on a band that can be worn around a body part such as a wrist, ankle, arm, or leg, for example, in order to excite, for example, the median, radial, and/or ulnar nerves or the tibial, trigeminal, saphenous and/or fibular nerves, and/or other peripheral nerves. As shown in FIGS. 4A-4D, the two electrodes, a first electrode 400 and a second electrode 402 (but no additional electrodes in some embodiments), can be spaced apart and located on the band such that when worn, each electrode is positioned on the skin over or proximate to a target nerve 404, 406. In some embodiments, as shown in FIG. 4A, the electrodes 400, 402 can be placed on the skin such that the electrodes are as close as possible to the target nerves 404, 406. In some embodiments, as shown in FIG. 4B, the electrodes 400, 402 can be spaced wider apart to flank the two nerves 404, 406 such that the two nerves 404, 406 are positioned between the two electrodes 400, 402. In some embodiments, as shown in FIG. 4C, the electrodes 400, 402 can be spaced more narrowly than the two nerves 404, 406 such that the electrodes 400, 402 are positioned between the two nerves 404, 406. In some embodiments, as shown in FIG. 4D, the electrodes 400, 402 can be positioned such that the two nerves 404, 406 fall approximately on a straight line drawn between the two electrodes 400, 402. In other embodiments, combinations of the electrode spacing described above relative to each nerve may be employed (e.g., the electrodes 400, 402 and nerves 404, 406 may be staggered).

In some embodiments, the spacing of the electrodes depends in part on the spacing between the nerves to be stimulated and/or the depth of the nerves beneath the skin because the spacing between the electrodes affects the depth the generated electrical field can reach. Generally, the further apart the electrodes (of opposite polarity) are placed, the deeper the electrical field will penetrate. The spacing may also be based on the circumference of the limb or body part and the positioning or location of the target nerves within the limb or body part. In some embodiments, the electrodes can be positioned on the same limb or body part of the subject to be treated, and in some cases spaced apart by a distance of within about 50 cm, 45 cm, 40 cm, 35 cm, 30 cm, 25 cm, 20 cm, 15 cm, 10 cm, 5 cm, 4 cm, 3 cm, 2 cm, or less.

There can be a balance between the width and spacing of the electrodes on the one hand and the circumference of the limb and spacing of the nerves being treated on the other hand. This has an effect on the sizing of the electrodes and band, and also on the number of band sizes to ensure coverage of the majority of the patient wrist sizes. If the electrodes are spaced too close together, the penetrations of the electrical fields are not as deep into the skin and may not reach the target nerves and/or may cause discomfort. If the electrodes are spaced too far apart, then a singular spacing of electrodes may not work for enough wrist sizes (will not appropriately position the electrodes on wrists of various sizes), which can yield too many different band sizes and electrode spacings for the product line. If the electrodes are too narrow, targeting the nerve will be quite difficult, but if the electrodes are too wide, then the electrodes cannot be spaced adequately for enough wrist circumferences, which will yield a lot of different sized products for the product line. For the wrist, electrode widths between about 10 mm-30 mm and electrode spacing between about 5 mm-20 mm can enable encompassing the vast majority of all individuals using approximately three band sizes, for example.

Figure 5A:
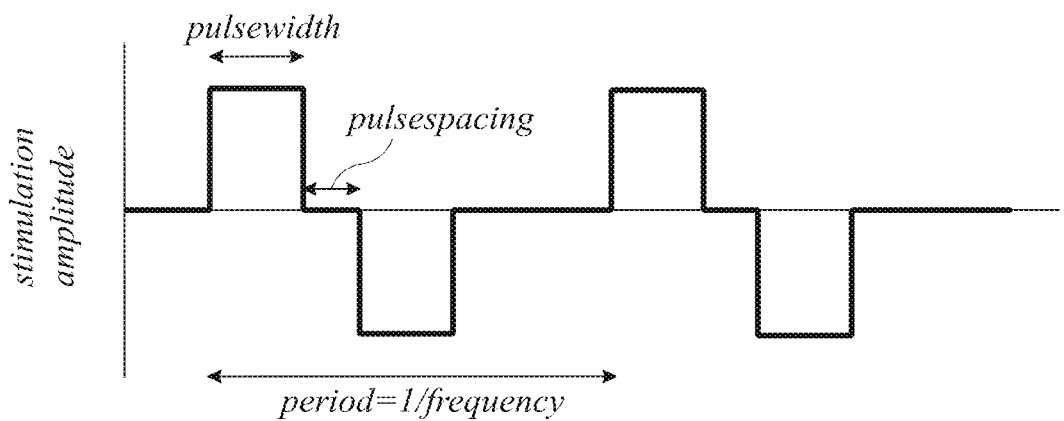
FIGS. 5A-5G illustrate various charge balanced waveforms and schematics of electrode configurations that can be used to stimulate a nerve.
Figure 5B:
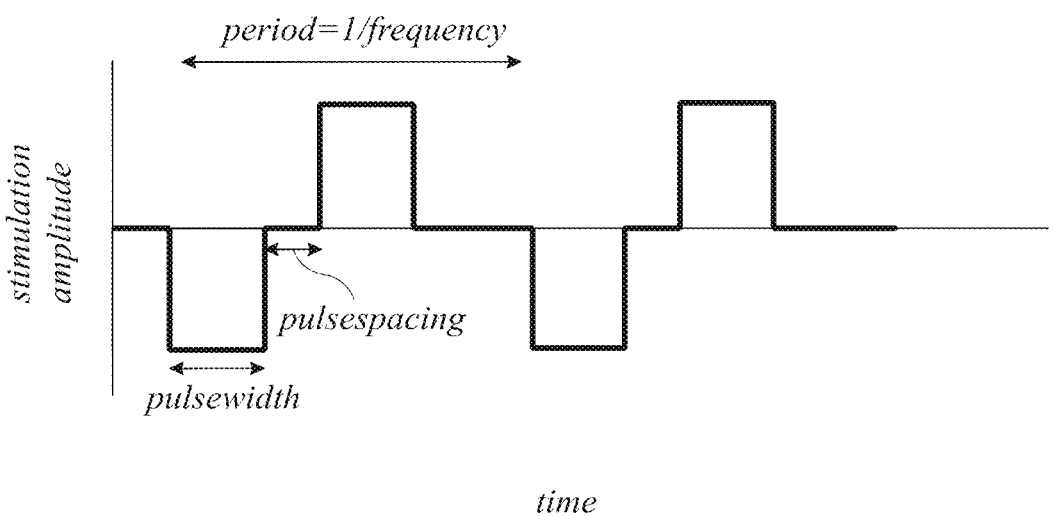

In some embodiments, the stimulation waveform is biphasic and charge balanced as shown in FIGS. 5A-5G. A biphasic waveform has a phase of a first polarity (e.g., positive current) and a phase of the opposite polarity (e.g., negative current). A charged balanced waveform has a net zero charge when the waveform is integrated over time (in other words, the cumulative area beneath the curve is zero). The stimulation waveform can have an excitatory phase/pulse and a charge balance phase/pulse with the opposite polarity. The excitatory phase may arise from an electrode serving as the excitatory electrode and the charge balance phase may arise from an electrode serving as the charge balance electrode. The excitatory electrode may be positioned over or proximate to one nerve (e.g., a first nerve) and the charge balance electrode may be positioned over or proximate to another nerve (e.g., a second nerve), as described elsewhere herein. In some embodiments, the stimulation waveform excitatory phase can excite the nerve located near the cathode without exciting the nerve under the anode. In other embodiments, the excitatory phase may be an anodic phase while the charge balance phase may be the cathodic phase. In some embodiments, the excitatory and charge balance phases can have the same amplitude and duration, as shown in FIGS. 5A and 5B, with the stimulation amplitude as the Y axis and time as the X axis. The pulse width, pulse spacing, and period variables are also illustrated. This type of symmetrical stimulation waveform can tend to stimulate both nerves, such as simultaneously. FIG. 5A illustrates an embodiment of a biphasic stimulation waveform with a positive-going leading edge, while FIG. 5B illustrates an embodiment of a biphasic stimulation waveforms with a negative-going leading edge. In some embodiments as illustrated in FIGS. 5A-5B, the waveforms can have square or rectangular shapes with stimulation at maximum amplitude. Other embodiments can include curved waveforms where there can be a ramp-up and/or ramp-down period to or from maximum amplitude. Other embodiments can include a sinusoidal waveform.

Figure 5C:
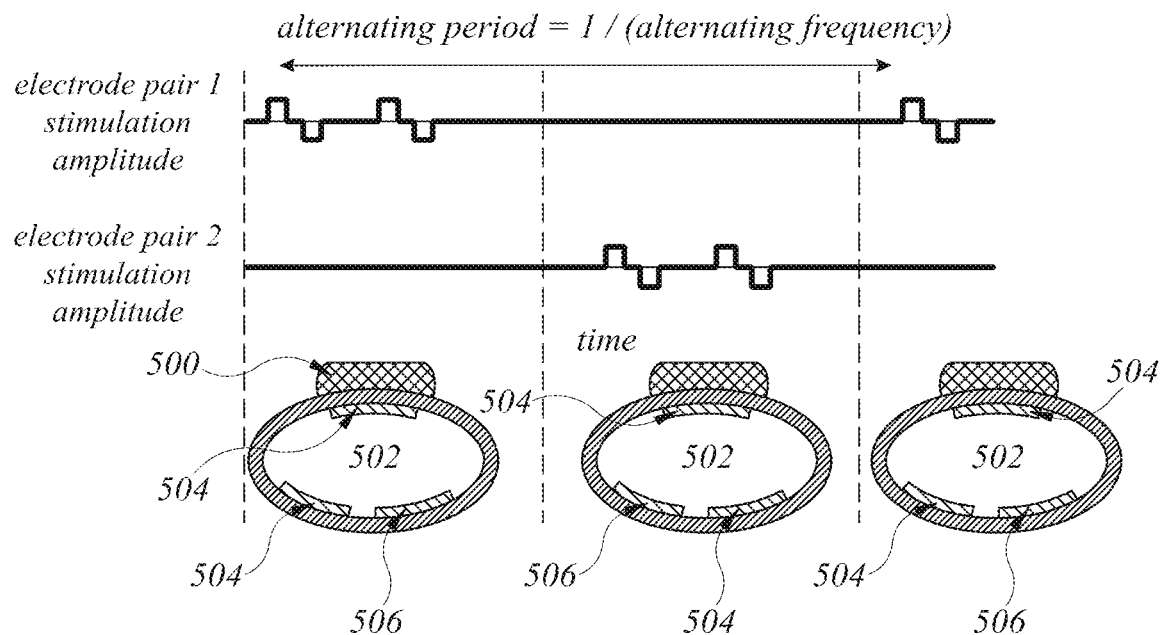

FIG. 5C illustrates a schematic illustrating a waveform and a stimulation device 500 positioned on the skin of a subject's limb 502, shown in cross-section. The device 500 can include in some embodiments 3 electrodes to stimulate 2 nerves (nerves not shown) with the electrodes grouped as alternating pairs (pair 1 and pair 2). The electrodes serving as activated electrodes 504 and inactivated electrodes 506 during particular phases of stimulation are shown. In another embodiment, utilizing exactly two electrodes to stimulate exactly two nerves such as illustrated schematically in FIGS. 4A-4D can utilize, for example, symmetrical stimulation waveforms such as shown, for example, in FIGS. 5A-5B to simultaneously stimulate exactly two nerves with exactly two electrodes.

Figure 5D:
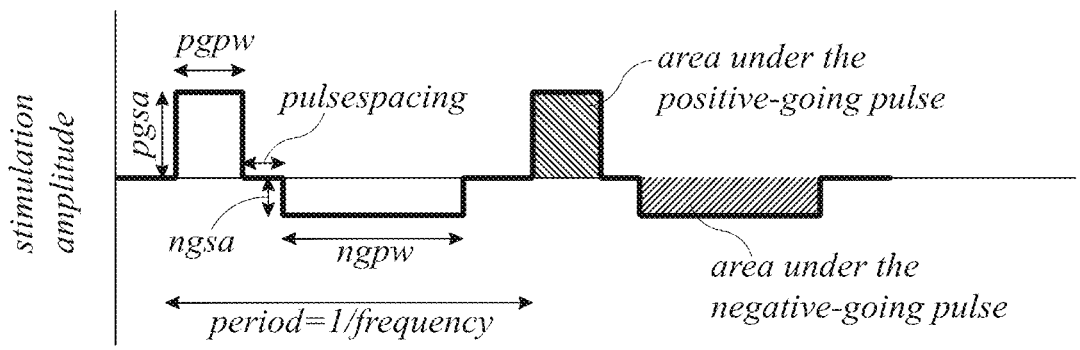
Figure 5E:
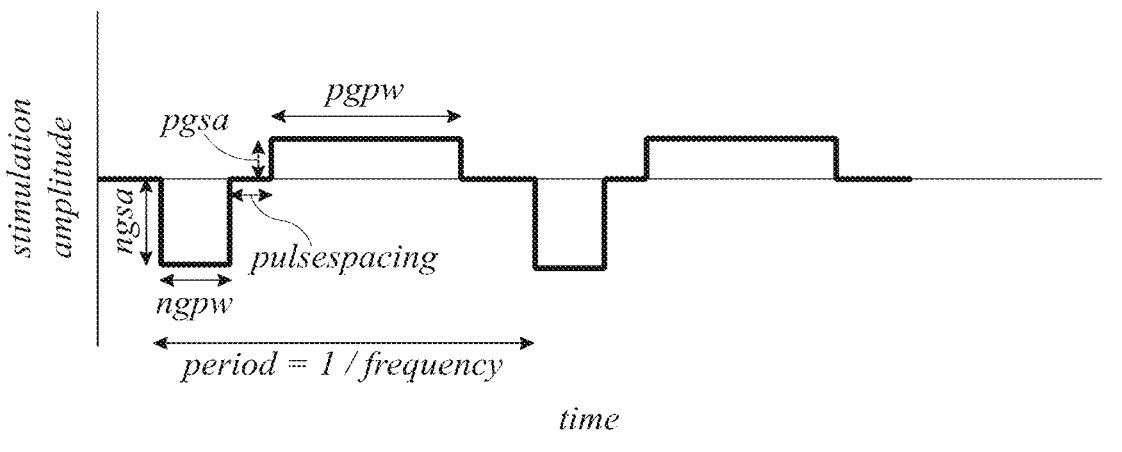

In other embodiments, the excitatory and charge balance phases of the stimulation waveform can have different amplitudes and durations, yet still remain charge balanced or substantially charge balanced. For example, as shown in FIGS. 5D and 5E, a first stimulation waveform can have an excitatory phase with a greater amplitude but a shorter duration than the charge balance phase to stimulate the nerve close to the electrode serving as the excitatory electrode such that the excitatory phase and the charge balance phase are not symmetric (e.g., not mirror inverses of each other), with the stimulation amplitude as the Y axis and time as the X axis. The pulse width, pulse spacing, and period variables are also illustrated. This type of asymmetrical stimulation waveform can allow for alternating stimulation of nerves (e.g., only one nerve at a time in some cases). FIG. 5D illustrates an embodiment of a biphasic asymmetric stimulation waveform with a positive-going leading edge, while FIG. 5E illustrates an embodiment of a biphasic asymmetric stimulation waveforms with a negative-going leading edge. As shown, the asymmetric waveform can be configured to be charge balanced such that the area under the positive-going pulse 552 can be equal to the area under the negative-going pulse. In some embodiments as illustrated in FIGS. 5D-5E, the waveforms can have square or rectangular shapes with stimulation at maximum amplitude. Other embodiments can include curved waveforms where there can be a ramp-up and/or ramp-down period to or from maximum amplitude. Other embodiments can include sinusoidal waveforms.

Figure 5F:
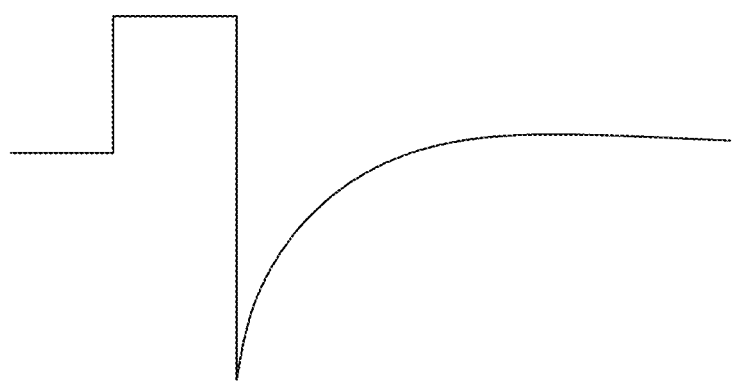

In FIG. 5F, the charge balance phase may initially have an amplitude that is equal to or greater than the excitatory phase, but its duration is relatively brief and the amplitude rapidly drops such that the waveform is not excitatory (the nerve is not stimulated), similar to a capacitive discharge. What is important in some cases is that the charge balance waveform is non-excitatory. The amplitudes and duration can be configured such that only one nerve, but not both nerves, is stimulated with the stimulation waveform, while the other (e.g., second) nerve is not stimulated by the stimulation waveform. A second stimulation waveform can also have an excitatory phase with a greater amplitude but a shorter duration than the charge balance phase, but the electrodes serving as the excitatory electrode and charge balance electrode can be switched, by reversing the polarities of the two electrodes, so that the second nerve is stimulated and the first nerve is not stimulated.

In some embodiments, the amplitude (e.g., the mean, median, or maximum amplitude) of the excitatory phase of the first stimulation waveform is about or at least about 2, 3, 4, 5, 6, 7, 8, 9, 10, 15, 20, or more times greater than the amplitude (e.g., the mean, median or maximum amplitude) of the charge balance phase of the first stimulation waveform, or within a range incorporating any two of the aforementioned values. In some embodiments, the pulse width can be between, for example, about 50 μs to about 1,000 μs. The stimulation amplitude can be, in some cases, between about 1-15 mA, or between about 1-10 mA, or between about 1-25 mA.

In some embodiments, the duration of the charge balance phase (either in total, or the duration of which the charge balance phase is at maximum amplitude or substantially at maximum amplitude) of the first stimulation waveform is about or at least about 1.25, 1.5, 2, 2.5, 3, 4, 5, 6, 7, 8, 9, 10, or more times greater than the duration of the charge balance phase of the first stimulation waveform, or within a range incorporating any two of the aforementioned values.

Figure 5G:
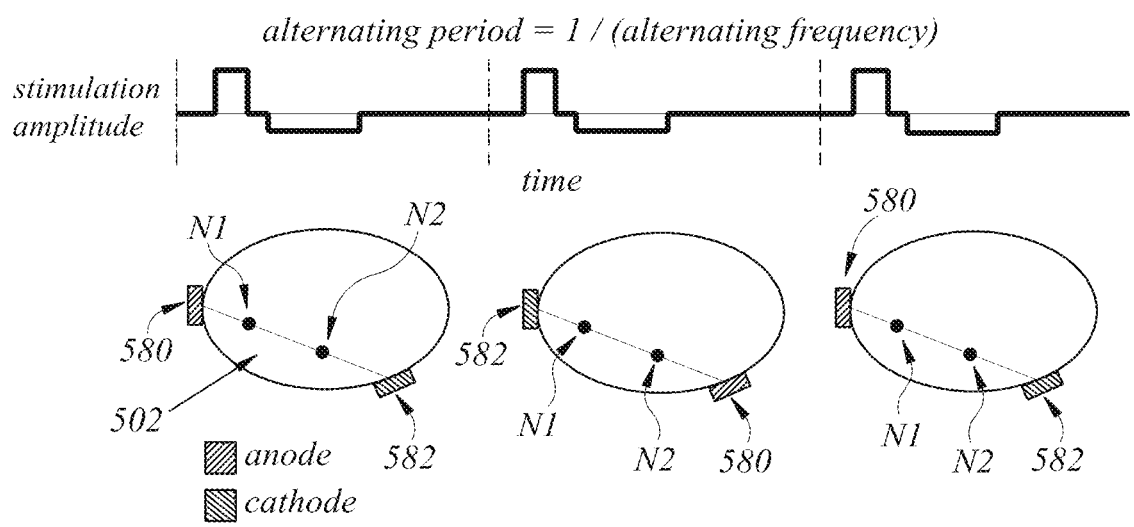

In some embodiments, as described above, the same two electrodes can switch functions as the excitatory electrode and charge balance electrode between stimulation waveforms/pulses so that each nerve can be stimulated serially (but not necessarily at the same time). In some implementations, this may be accomplished by switching the polarities of the two electrodes and applying the same or similar stimulation waveform from the second electrode as the first electrode, as illustrated schematically in FIG. 5G, showing exactly two electrodes for stimulating exactly two nerves (N1 and N2) on a patient's limb 502, and the electrodes serving as the anode 580 and the cathode 582 can change depending on the desired stimulation pattern. In other implementations, this may be accomplished by retaining the same polarities but by altering the amplitudes and durations of the cathodic and anodic phases, such that a cathodic electrode is used to stimulate the first nerve and an anodic electrode is used to stimulate the second nerve or vice-versa. In some embodiments, three, four, or more electrodes as part of an array, or multiple pairs of electrodes can alternate as either excitatory electrodes or charge balance electrodes as noted above.

Stimulation Timing

Figure 6A:
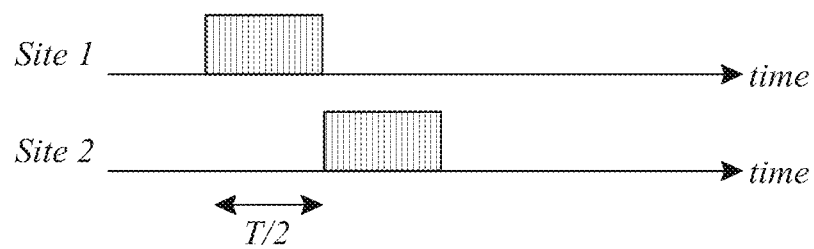
FIGS. 6A-6B illustrate various schemes for nerve stimulation at multiple sites.
Figure 6B:
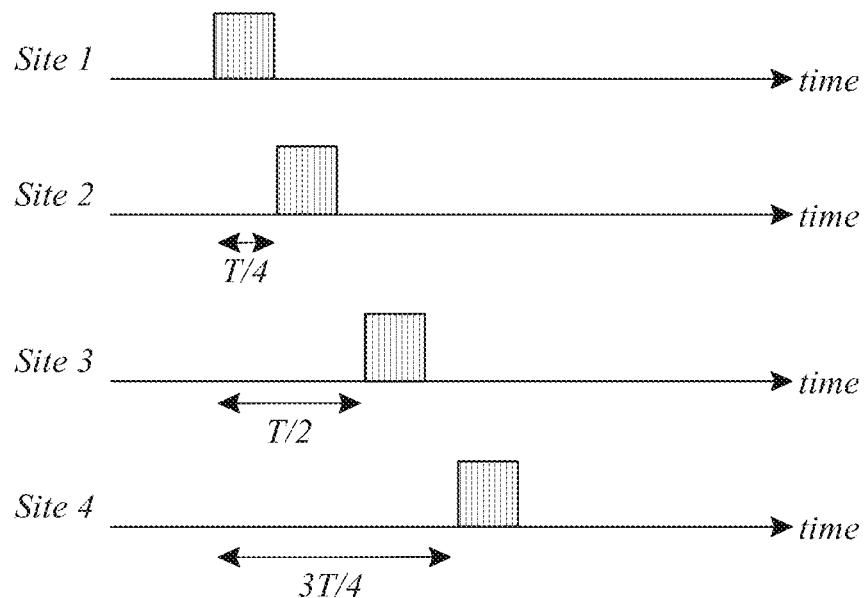

Since the nerves can be independently stimulated, it allows for each nerve to be stimulated, in some embodiments at different times, as shown schematically in FIG. 5C above. For example, after the first nerve has been stimulated or has started being stimulated, the second nerve can begin stimulation after a delay that can be based on the period of the tremor, T, as shown in FIGS. 6A and 6B. For example, the delay can be the period of the tremor divided by the number of nerves to be stimulated, which can be exactly two when just the median and radial nerves are to be stimulated.

Some stimulation schemes can be designed to dephase, override or obscure an abnormal neural network. For example, in some embodiments for stimulation to reduce hand tremor, as illustrated in FIG. 6A, a conceptual diagram showing a sample excitation scheme to dephase brain regions receiving sensory input from two sites. For example, the two sites could be two locations on the wrist over the median and radial nerves. The stimulation at site 2 is delayed after site 1 by time T/2, where T is the period of the native tremor. For example, if the tremor is at 8 Hz the period is 125 ms and the stimulation of site 2 would be delayed by 62.5 ms. The stimulation is designed to reset the phase of the neuron, which may be implemented using high frequency stimulation (e.g., above 100 Hz) as shown in FIGS. 6A and 6B or a DC pulse. FIG. 6B is a conceptual diagram showing a sample excitation scheme to dephase brain regions receiving sensory input from four sites, with subsequent sites delayed by T/4. In some implementations, the stimulation scheme is periodic, repeating the stimulation pulses at regular intervals over a duration of time.

Wearable Band

Figure 7:
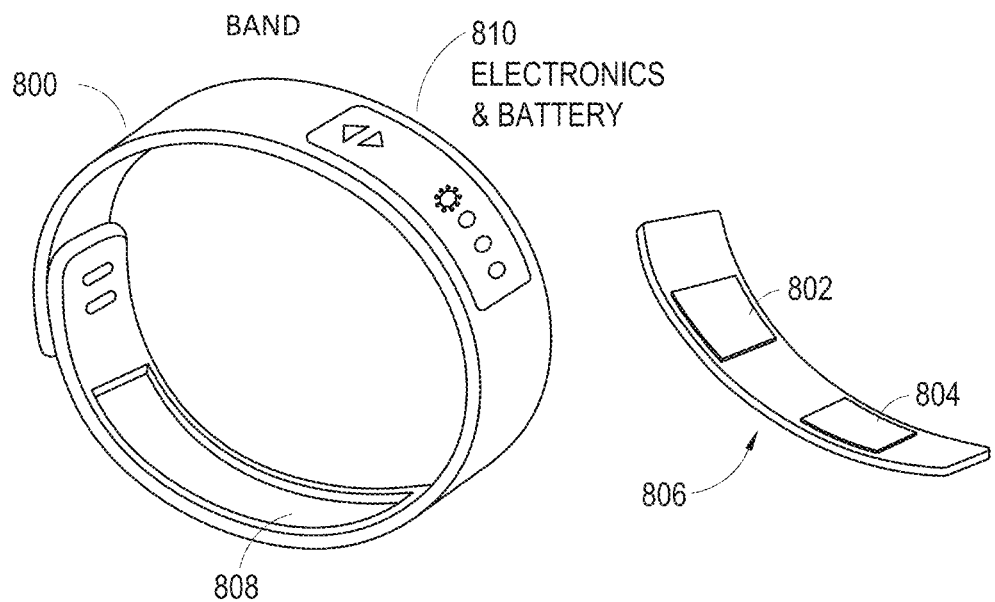
FIGS. 7 and 8 illustrate various embodiments of a wearable band with two electrodes.
Figure 8:
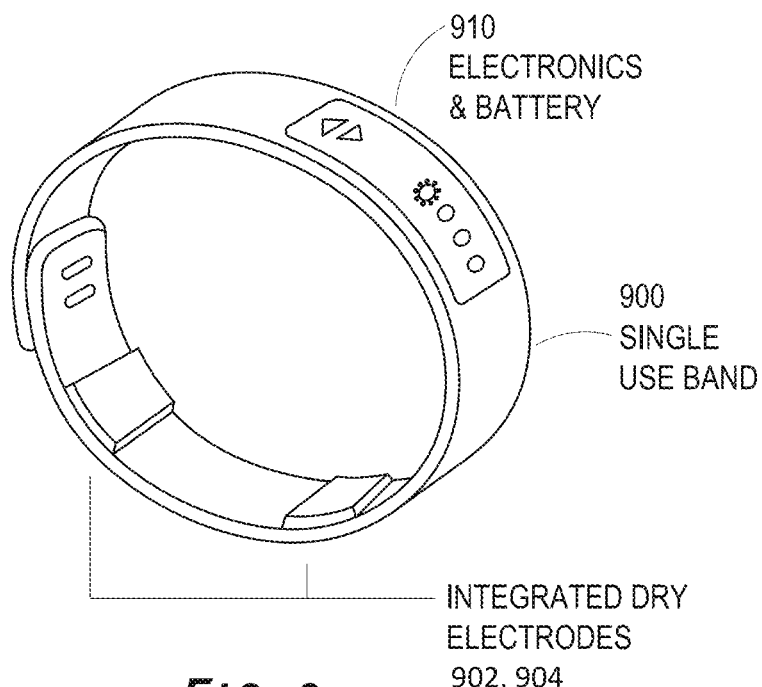

In some embodiments as shown in FIGS. 7 and 8, the electrodes can be disposed on a wearable band that can be worn around the wrist, arm, ankle, leg, or other limb or body part. The wearable band may include a removable/detachable controller as further described in International Application No. PCT/US2016/37080, titled SYSTEMS AND METHOD FOR PERIPHERAL NERVE STIMULATION TO TREAT TREMOR WITH DETACHABLE THERAPY AND MONITORING UNITS, which is hereby incorporated by reference in its entirety for all purposes. As shown in FIGS. 7 and 8, the wearable bands have two electrodes which can be used to stimulate up to two nerves. However, other embodiments can have N electrodes to stimulate up to N nerves, wherein N represents a variable integer number as described elsewhere herein.

FIG. 7 illustrates a wearable band 800 with disposable electrodes 802, 804. In some embodiments, the disposable electrodes 802, 804 can be coated or covered with an electrically conductive material, such as a solid hydrogel or a conductive liquid. The disposable electrodes 802, 804 may be disposed on a strip 806 that can be removably attached to the wearable band 800, which may have a receptacle 808 for receiving the strip 806. Other embodiments may comprise other means of attaching the strip 806 to the band 800. The strip 806 and the band 800 can have electrical contacts and a flexible circuit so that the electrodes are electrically connected to the controller 810. To accommodate various body part sizes, the disposable strip 806 can be provided with a variety of electrode spacings. This allows one band size, which can be adjustable (e.g., via an adjustable clasp or hook and loop fastener), to accommodate users with different body part sizes. In some embodiments, hydrogel coated electrodes may be more suitable for use with removable electrodes, as shown in FIG. 7, that can be disposed and replaced on a regular basis, such as every 1, 2, 3, 4, 5, 6, or 7 days, for example.

FIG. 8 shows a wearable band 900 with integrated electrodes 902, 904. In some embodiments, the integrated electrodes 902, 904 can be dry electrodes, described elsewhere herein, in electrical communication with a controller 910, comprising electronics for operating the device and a battery, which may be rechargeable. In some embodiments, the controller 910 may be detachable from the band 900. The electrodes 902, 904 may be in electrical communication with the controller 910 through a flexible circuit embedded in the band 900. Dry electrodes may be more suitable for longer term use electrodes that can be used for months, such as at least 3 months, before the band needs to be replaced.

In some embodiments, the band may be a single use band that can be used for a relatively long period of time before replacement.

Dry Electrodes

A dry electrode for transcutaneous electrical stimulation and/or for electrical sensing can be used for many applications, including but not limited to peripheral nerve stimulation for treating tremor, osteoarthritis, overactive bladder, high blood pressure, dysrhythmias, pain, diabetes, and inflammatory diseases. Dry electrodes advantageously do not require any adhesive or layer of conductive moisture (such as a gel or spray) to achieve the skin contact sufficient for comfortable delivery of electrical stimulation. In contrast, wet electrodes utilize either integrated adhesives or conductive gels and moisture to achieve that contact and electrical connection. Some such examples are hydrogels, which can be adhesive or non-adhesive. The gels and moisture tend to dry out over time and the adhesives tend to only be effective for one use due to contamination from adhesion of dead skin cells, dirt, etc. As such, wet electrodes tend to be not reusable or only reusable for a short period of time, for example less than one day, even when stored optimally. Dry electrodes allow the electrode to be effectively used for relatively long periods of times, such as for about or at least about 1, 2, 3, 4, 5, 6, 7, 8, 9, 10, 11, or 12 months, 1, 2, 3, 4, 5 years, or more before the electrode needs to be replaced.

There are several challenges in developing a dry electrode in a body-worn device that provides comfortable transcutaneous stimulation. First, the electrode can in some cases have a bulk resistivity (e.g., the inverse of conductance) that is near the resistivity of skin, or resistivity high enough to allow for a uniform distribution of current through the electrode, as concentration of current, especially around electrode edges or imperfections in the electrode surface, can cause uncomfortable stimulation. Most dry electrode materials utilize a polymeric base material, such as silicone, loaded with a conductive filler material, such as carbon. Bulk resistivity depends on the amount of filler material loaded into the base polymer, and also the resistivity of the base polymer. In some implementations, optimal bulk resistivity for providing good conduction in a body-worn device may be between about 25 and about 2000 ohm·cm, between about 50 and about 1000 ohm·cm, or between about 100 and about 500 ohm·cm.

Second, the electrode can be configured to be compliant enough to provide conformance to the skin, especially around bony structures such as the radius and ulnar bones in the wrist. If the material is too stiff and cannot conform to the skin, areas of the electrode surface can lift from the skin, causing concentrations in current and uncomfortable stimulation. Compliance of the electrode depends on the base polymer material properties, the amount of conductive filler material loaded into the base polymer, and the thickness of the electrode. For example, more filler material tends to lead to a less compliant (or stiffer) electrode. Additionally, a thicker electrode will tend to be stiffer than a thinner electrode. In some implementations, a preferred durometer for providing good conformance to a dry electrode may have a Shore hardness between about 25 A and about 55 A, between about 30 A and about 50 A, or between about 35 A and about 45 A.

Third, the electrode can in some cases have uniform material properties across the surface of the electrode, which must be controlled during manufacturing. Drastic inhomogeneities in properties of the electrode surface, such as resistivity or surface finish, can also cause concentrations in current and lead to uncomfortable stimulation. In some implementations, an optimal measure of homogeneity for providing uniform current distribution may be less than about 10%, 9%, 8%, 7%, 6%, 5%, 4%, 3%, 2%, or less difference in resistivity across the electrode surface. Uniform material properties of a dry electrode depend upon a uniform distribution of the conductive filler material in the base polymer and a uniform surface finish across the electrode, the latter of which is typically controlled by the surface finish of a mold. These three properties of the electrode affect each other, so designing a cost-efficient, manufacturable, and durable dry electrode material that provides comfortable transcutaneous stimulation requires optimizing these multiple parameters.

In some embodiments, as shown in FIGS. 9A-9D, the dry electrode 100 includes a conductive base layer 102 and a conductive skin contact layer 104 made of a conductive plastic, rubber, silicone material, or other suitable dry material. In some embodiments, the base layer 102 can include a thin layer of conductive material (e.g., copper, gold, silver-coated copper, stainless steel, silver, silver chloride, titanium, other metals or metal alloys, combinations thereof, polydimethylsiloxane, etc). In some embodiments, the base layer 102 can include metal coated polymer or plastic. In another configuration, the base layer 102 can include conductive polymer or plastic. In some embodiments, any two, three, or more materials such as those disclosed herein can be combined to make a base layer 102. The base layer 102 may be, for example, a continuous metal or a patterned metal. The size of metal patterns can be relatively large, such as, for example, between about 50% and about 70% of the surface area of the base layer 102, or about or at least about 50%, 55%, 60%, 65%, 70%, 75%, or 80% (or ranges incorporating any two of the aforementioned values) of the surface area of the base layer 102 and still maintain a uniformity of current density of the electrode depending on the conductivity of the dry electrode 100 as well as the frequency of the waveform being delivered. Keeping the base layer 102 thin may allow increased flexibility, desirable for body-worn applications, especially where a stiff material is used. Using a patterned metal may also enhance the flexibility of the base layer 102.

In some embodiments, the dry electrodes 100 need to maintain good skin contact across the surface of the skin contact layer 104 in order to deliver comfortable transcutaneous electrical stimulation at the appropriate current. As such, the materials that make up the dry electrodes 100 typically are more conformal materials that are loaded with conductive materials. Challenges also lie in the ability for the base layer 102 to maintain flexibility without deforming or fracturing. The strong, secure electrical connection between the base layer 102 and the conductive layer 104, which in some embodiments are two or more different materials, can also be important in some cases to prevent delamination, which can cause the conductance to greatly decrease.

In some embodiments, the skin contact layer 104 is disposed, layered or coated over the base layer 102 and may include any moldable polymer, rubber, or plastic, including but not limited to silicone, rubber, or thermoplastic urethane. The material could be loaded with one or more conductive fillers, including but not limited to metal, carbon (e.g., carbon nanotubes or carbon black), graphite, and metal coated particles (e.g., metal-coated, such as silver-coated glass microspheres or bubbles). In some embodiments, the conductive filler material may be a mixture of different filler materials with different conductivities. For example, in some embodiments, a first highly conductive material (e.g., a metallic material) may be mixed with a second material with lower conductivity with respect to the first conductive material, such as carbon black, in order to increase the conductivity of the second filler material. The second material may have better physical properties (e.g., reduced stiffness) than the first material. Mixing filler material may allow less filler material to be used, resulting in a more flexible skin contact layer 104.

Figure 9A:
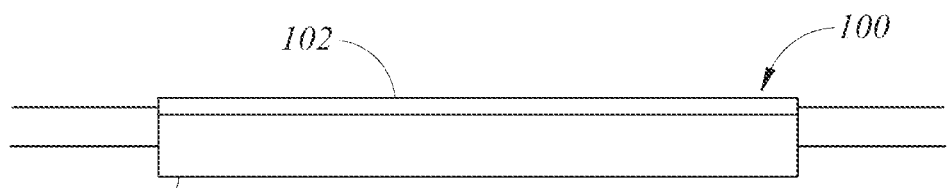
FIGS. 9A-9H illustrate various embodiments of dry electrodes.
Figure 9B:
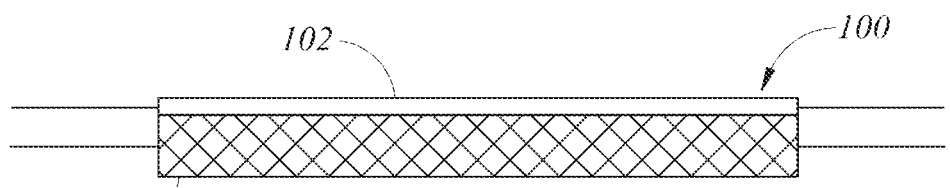
Figure 9C:
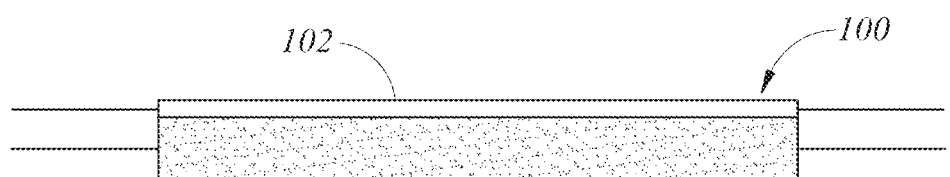

In some embodiments, as shown in FIG. 9B, the conductive filler material can be in a fiber form. In some embodiments as shown in FIG. 9C, the conductive filler material can be in a powdered or particulate form when added to the silicone, rubber, or plastic material. In some embodiments, a powdered form may be preferable over a fiber form in order to create a more uniform conductance across the surface of the loaded material. Long fiber length materials may extend through the entire thickness of the skin contact layer 104 and/or may be more difficult to evenly disperse, thereby creating areas of high conductance in some locations and areas of low conductance where the fibers are absent. The areas of high conductance may transmit too much current to the skin and cause pain or discomfort. In contrast, powder materials may be more easily and more uniformly dispersed throughout the skin contact layer to yield a material with uniform conductance across its surface. However, in some embodiments, materials that include fibers can be utilized.

Figure 9D:
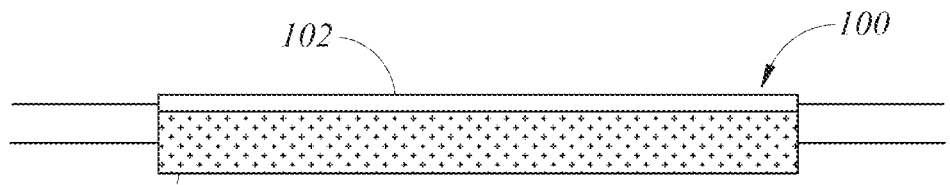

In some embodiments as shown in FIG. 9D, the skin contact layer 104 can include open cell foam treated with a conductive surface coating that causes the foam to be conductive. The open cell foam can provide a high surface area-to-volume ratio which allows increased incorporation of the conductive coating. In some embodiments, the foam pattern is random and in some embodiments, it is not random. In some embodiments, the skin contact layer 104 can include a non-conductive substrate made from a porous material, including but not limited to foam, neoprene, sponge, etc. filled with a conformal conductive coating that allows current to pass from the base layer backing 102 to the skin contact layer 104.

In some embodiments, a fibrous filler material may tend to increase the stiffness or durometer of the loaded material more than a powdered filler material. Also, more generally, as more filler is added and the concentration of filler increases, the loaded material tends to increase in stiffness. However, a low durometer, flexible material can be desirable in some embodiments to result in good conformance to the skin, which improves the physical comfortability of wearing the electrode 100. In addition, poor conformance to the skin can lead in some cases to the concentration of current through the electrode 100 to a smaller area still in contact with the skin, leading to the perception of pain if the resulting current density is too high. Therefore, in some embodiments where increased flexibility is desirable, a powdered filler material may be preferred and the amount of filler material can be limited or reduced in order to keep the durometer of the material within a desired limit. In some embodiments, the powder or particulate filler material can possess a diameter, length, width, and/or thickness that is less than about ⅓, ¼, ⅕, 1/10, 1/100, or less than the thickness of the skin contact layer 104. The amount or loading of filler material can affect both conduction and stiffness. The optimal loading amount will generally depend on the materials used for both the skin contact layer 104 and the conductive filler. In embodiments having a skin contact layer 104 comprising a silicone base polymer material, silver-coated glass bubbles having diameters of, for example, between about 10 μm and about 100 μm, between about 18 μm and about 50 μm, or approximately 18 μm, 25 μm, 35 μm, or 50 μm. can have a loading for example, of between about 1% and about 40%, between about 3% and about 25%, between about 5% and about 20%, or about 5%, about 10%, or about 20% (measured by weight or volume). In embodiments having a skin contact layer 104 comprising a silicone base polymer material, a preferred loading of conductive single walled carbon nanotubes (SWCNT) may be, in some embodiments, about or less than about 10%, 9%, 8%, 7%, 6%, 5%, 4%, 3%, 2%, 1%, or less, or between about 1% and about 5% (measured by weight or volume). In some embodiments, incorporation of such materials can be unexpectedly advantageous when used as dry electrode materials. For example, glass bubbles can reduce weight of material, as the density is lower than most polymers (because bubbles are filled with air). Conductivity of the filler material can be controlled with the type of silver or silver alloy applied to the glass bubble. The spherical shape of the bubbles can advantageously allow for uniform or substantially uniform dispersion the in base polymer. SWCNTs have high conductivity (e.g., $10^6$ to $10^7$ S/m) and robust mechanical properties (combination of stiffness, strength, and tenacity) as a filler material within a polymer. Loading of SWCNTs can be more efficient (by weight or volume) than carbon black or carbon fibers as the structure of SWCNTs allow better transfer of their mechanical load to the polymer matrix. Conductivity of SWCNTs can be controlled during manufacturing by the chiral vector, C=(n, m), the parameter that indicates how the graphene sheet is rolled to form a carbon nanotube. Both materials can advantageously require less loading by volume to achieve required conductivity and changes in conductivity are less sensitive to deformation of the electrode material, for example due to applied pressure or forces during wear.

In some embodiments, any number of the following materials could be incorporated into a dry electrode: metals and metal alloys (e.g., stainless steel, titanium (e.g., 6AI-4V (Ti64) or cobalt chrome); graphite coated with pyrolytic carbon (e.g., pyrolytic carbon AXF-5Q POCO); a conductive ink/coating (e.g., silver or silver chloride printed ink); a self-wound transfer adhesive that can include an electrically conductive pressure-sensitive adhesive, e.g., ARcare 90366 from Adhesives Research, Glen Rock, Pa.); a double-sided, isotropically conductive pressure sensitive tape which conducts electricity through the thickness (the Z-axis) and the plane of the adhesive (X, Y planes)(e.g., XYZ-Axis Electrically Conductive Adhesive Transfer Tape 9719 from 3M, Maplewood, Minn.); a conductive fabric having multiple layers (e.g., screen printed breathable fabric electrode arrays); a textile electrode that includes silver-coated nylon (e.g., a conductive fabric that includes silvered polyamide and/or Spandex); silver-plated, aluminum-filled fluorosilicone; a thermoplastic elastomer with conductive particle filler (e.g., X TP-1494502 Natural from STAT-TECH, PolyOne Corp., Avon Lake, Ohio); silicone filled with nanoparticles (e.g., silver nanoparticles, such as LTE-75 from Leader Tech (Tampa, Fla.); thermoplastic polyolefin elastomer (TEO), and/or thermoplastic vulcanizate (TPV) styrene ethylene butylene styrene (SEBS) alloy with carbon black (e.g., ESD C2800 B-45 A Black from RTP Co., Winona, Minn.); electrically conductive silicone (e.g., silver plated aluminum such as SSP-2368 from Specialty Silicone Products, Inc., Ballston Spa, N.Y.); silicone elastomers with silver fillers;

conductive elastomers such as silicone with carbon black (e.g., NuSil EPM-2461P from NuSil Technology, Carpinteria, Calif.); and/or a hydrogel (e.g., Axelgaard AG735 from Axelgaard Manufacturing Co. Ltd., Fallbrook, Calif.).

The resistance of the skin contact layer 904 can increase proportionally with thickness; therefore minimizing thickness of the skin contact layer 904 can improve conductivity of the electrode 900. Higher resistance in the electrode 900 due to a thicker skin contact layer 904 could increase power required in the system to maintain the desired current. However, if the skin contact layer 904 is too thin, variations in the processing could cause significant inhomogeneity in the material properties and/or conductance at the skin contact layer 904. The skin contact layer 904 thickness can be, in some embodiments, between about 0.25 mm and about 5 mm, between about 0.5 mm and about 2 mm, between about 0.5 mm and about 1 mm, between about 1 mm and about 2 mm, between about 0.15 mm and about 10 mm, or ranges including any two of the aforementioned values or ranges there between.

Figure 9E:
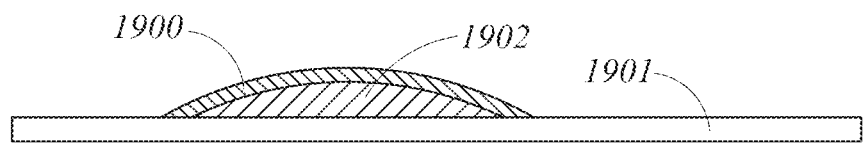
Figure 9F:
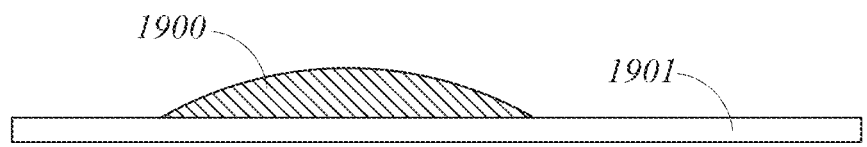
Figure 9G:
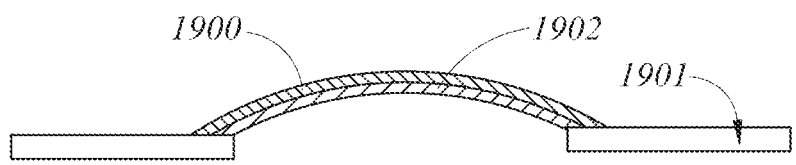
Figure 9H:
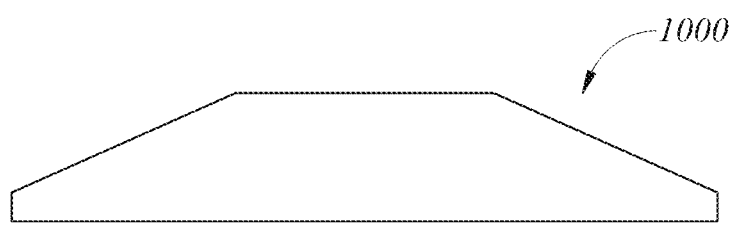

Overall, the thickness of the electrode 900 can affect its flexibility and stiffness, with the stiffness increasing with increasing thickness. In some embodiments, the thickness of the skin contact layer 904 depends of the material properties (e.g., natural durometer) of the selected material, such as silicone, the choice of filler (e.g., for providing conductivity), and the desired durometer and desired resistivity or conductance of the conductive filler loaded skin contact layer 904. In some embodiments, the skin contact layer 904 of the electrode 900 can have a durometer between a shore hardness of about 10 A to 50 A, between about 10 A and about 30 A, between about 50 OO and about 50 A, between about 40 OO and about 70 A, or ranges including any two of the aforementioned values or ranges there between. In some implementations, these durometers can provide good conformance to the skin. As discussed above, the durometer can be controlled by various factors, including material selection, thickness of the layers, and the type and/or amount of the conductive filler added to the skin contact layer 904. Additionally, the surface tackiness of the electrode 900 could be modified to enhance or decrease gripping against the skin (i.e., friction or resistance to shear force). Enhanced gripping (as in the case of a fully smooth electrode) could aid in skin conformance and reduction of sliding, which would reduce the unpleasant changes in stimulation intensity experienced by a wearer. In some embodiments, the skin-contacting surface 904 of the dry electrode 900 is smooth and flat, and lacks any spikes, projections, bumps, microneedles, or similar features. However, other embodiments could have a curved, domed, or tapered shaped electrode surface that could help improve contact with the skin at the center of the electrode, where current is delivered, by applying more contact force and reducing likelihood of sliding. In some embodiments, the curved or domed electrode 1900 can have a backing material 1902 that is as or more compliant as the electrode material 1900, as illustrated in FIG. 9E, to apply appropriate pressure for good skin conformance. Also illustrated is a band 1901 which can be circumferential in some embodiments and configured to attach to a plurality of spaced apart electrodes as disclosed elsewhere herein. In some embodiments, the curved dry electrode 1900 does not require a separate backing material, as illustrated in FIG. 9F. In some embodiments, as illustrated in FIG. 9G the backing material 1902 is also curved or domed to match the shape of the dry electrode 1900, which could provide beneficial adhesion of the two layers during manufacturing or control stiffness of the dry electrode assembly. FIG. 9H schematically shows a side view of a tapered electrode 1000 to improve the conformability and control of delivery of current at the edges of the electrode. As shown, the electrode 1000 can be thicker in the center of the electrode than at the peripheral edges of the electrode. In some embodiments, the thickness at the center of the electrode 1000 can be about or at least about 1.5×, 2×, 2.5×, 3×, 4×, 5×, 6×, 7×, 8×, 9×, 10×, or more times the thickness at the peripheral edges of the electrode.

Additionally, concentrated delivery of current to the skin due to edges of the electrode can in some cases cause pain or discomfort; a curved shape would also increase the radius of edges to reduce likelihood of current concentrations. However, other embodiments can include one or more of the aforementioned features. However, if too tacky, this could make the band of a wearable device difficult to slide over the appendage. In this case, more subtly texturing the surface and/or treating the skin contact layer 904 with a coating could provide a more moderate level of tackiness.

The thickness and patterning of the base layer 902 can also in some cases affect the ability of the electrode to mechanically bend and conform to different body parts, like the arm, wrist, hand, knee, ankle, or leg, for example. Continuous metal foils or films on thin polyimide substrates can be good candidates for producing flexible bands. Continuous metals can, in some embodiments, preferably be ductile enough to produce the bends needed for the particular appendage—for instance in a typical gold coated flex application, copper is coated with nickel and then passivated with gold. In some embodiments, because nickel tends to be brittle and crack, only a thin layer of nickel is desired. This flexibility could also be increased by patterning the backing material in a serpentine fashion along the direction of the bending. Additionally, other more ductile metals such as silver could be used for the conductive base layer backing 902.

Figure 10A:
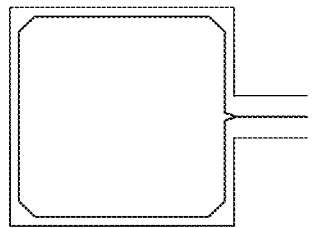
FIGS. 10A-10C illustrate views of mechanical elements, such as holes, that can allow the skin contact layer to surround the base layer and maintain good contact.
Figure 10B:
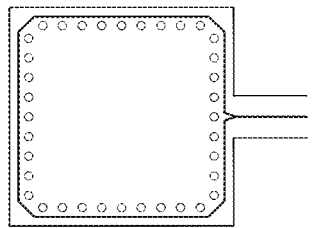
Figure 10C:
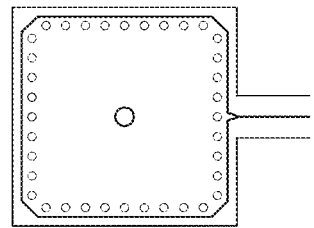

The adhesion of the skin contact layer to the base layer can be important as delamination can cause the electrical current to be unable to pass to the wearer. Adhesion can be improved using mechanical elements, as shown in FIGS. 10A-10C. FIG. 10A illustrates a base layer 1002 with no mechanical attachment or adhesion means for adhering to the skin contact layer. FIG. 10B illustrates a base layer 1002 with a plurality of holes 1003 positioned uniformly around the perimeter of the base layer 1002. FIG. 10C illustrates a base layer 1002 with a plurality of holes 1003 positioned uniformly around the perimeter and a larger hole 1003' positioned approximately in the center of the base layer 1002. These holes 1003, 1003' allow the skin contact layer material (e.g., silicone) to surround (e.g., penetrate) the base layer 1002 upon application (e.g., overmolding) and maintain good contact. Any combination of these holes 1003, 1003' may be used across the base layer 1002. In addition, surface treatments such as primers, corona or plasma treatments can be used to prep the surface of the base layer 1002 material for promoting adhesion of the skin contact layer.

In some embodiments, instead of overmolding directly onto the base layer, the skin contact layer can be adhered to the base layer using loaded glues (e.g., silver epoxies) or other conductive adhesives such as Z-axis tapes that allow conduction only in the z-direction across the thickness of the tape and not along the length or width of the tape (i.e., the direction perpendicular to the surface of adhesion). Provided the interface is thin enough, nonconductive adhesives can also be utilized in some embodiments.

To provide stimulation that is comfortable to the wearer, several features of the electrode can be desirable in some embodiments as discussed elsewhere herein. One electrode feature in some embodiments is to provide the electrode surface with a substantially uniform homogeneity of conductance, meaning that the current is transmitted evenly across the skin contact surface of the electrode. To validate whether the electrode surface has a substantial uniform homogeneity of conductance, the end-to-end resistance or conductance of the skin contact layer, or the entire electrode with the base layer added to the skin contact layer, can be measured at a plurality of points across the entire skin contact surface of the electrode. In some embodiments, the standard deviation of the measured resistivity or conductance at the plurality of points is less than about 10, 15, 20, 25, 30, 35, 40, 45, or 50 (on an absolute, like ohm-cm, or percentage basis) more or less than the average value or mean value of the measured resistivity or conductance. In some embodiments, verifying whether the current passing through the skin contact surface is uniform can be measured at a plurality of points across the entire skin contact surface of the electrode. In some embodiments, the standard deviation of the measured current at the plurality of points is less than about 10, 15, 20, 25, 30, 35, 40, 45, or 50 (on an absolute, like milliamps, or percentage basis) more or less than the average value or mean value of the measured current.

In some embodiments, the dry electrodes can be disposed in a band that applies pressure, such as radially inward pressure in some cases, in order to maintain good contact and a good electrical connection with the skin. Various embodiments of the band, such as a D-ring, or inflatable cuff, are all bands that when combined with thin dry electrodes can provide the skin conformance needed to provide good electrical contact. In some cases, the pressure required to provide effective electrical contact is around 10-40 mmHg, around 5-50 mmHg, around 15-300 mmHg, or ranges including any two of the aforementioned values or ranges there between.

In some embodiments, the conductive material forming the skin contact layer has a high volume resistivity that can be between about 1 ohm·cm and about 2000 ohm·cm, between about 20 ohm·cm and about 200 ohm·cm, between about 100 ohm·cm and about 1000 ohm·cm, between about 5 ohm·cm and about 100 ohm·cm, between about 1 ohm·cm and about 10,000 ohm·cm, or ranges including any two of the aforementioned values or ranges there between. These resistivity ranges can be comparable with current hydrogel electrodes. A lower volume resistivity can result in discomfort during stimulation, while a higher volume resistivity can result in power loss. Therefore, in some embodiments, a moderate volume resistivity may be optimal.

Figure 10D:
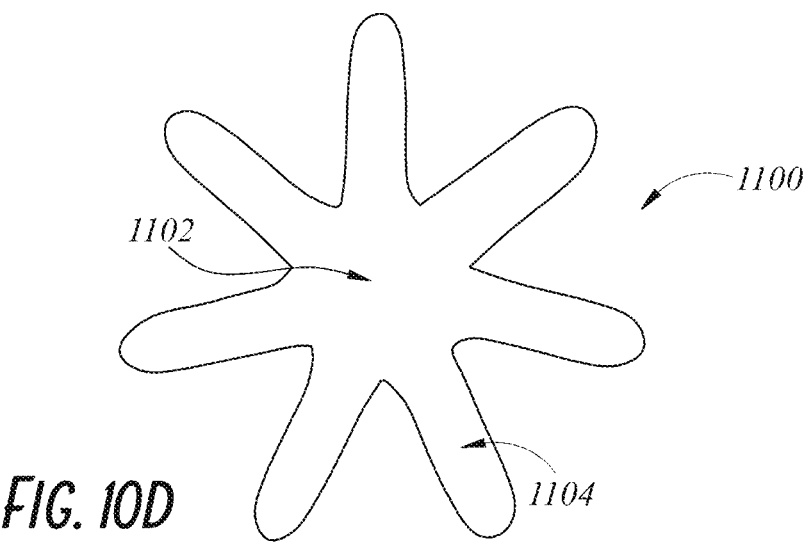
FIG. 10D illustrates a star-shaped dry electrode, according to some embodiments of the invention.
Figure 10E:
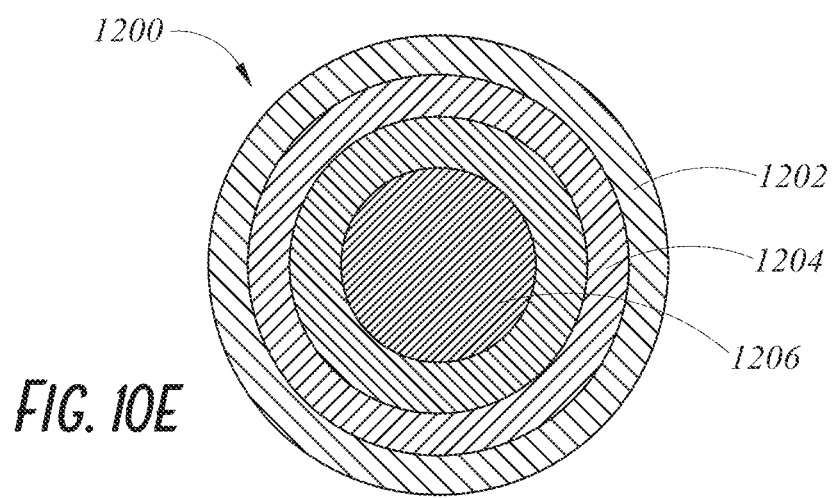
FIG. 10E illustrates schematically a cross-section of a dry electrode with a variable filler concentration.

In some embodiments, the electrode can have a lower resistivity towards the center of the electrode and a higher resistivity toward the edges of the electrode to reduce the likelihood of concentration of current being delivered through the edges of the electrode (i.e., spreading the current across the surface of the electrode). Concentrated delivery of current to the skin due to edges of the electrode can cause pain or discomfort. Resistivity of the electrode can be controlled by varying the concentration of conductive filler material throughout the electrode 1200, as illustrated in FIG. 10E, schematically illustrating a cross-section of a dry electrode that can include a first outer zone 1202 with less filler material at the edge of the electrode with relatively low conductivity, a second middle zone 1204 with more filler material than the outer zone 1202 with relatively intermediate conductivity, and a third inner zone 1206 with more filler material than the first outer zone 1202 and the second middle zone 1204 and relatively high conductivity. Some embodiments could have a different number of zones, such as two, four, five, or more zones, or a gradual conductivity gradient within each zone. In some embodiments, the resistivity of the electrode can be controlled by varying the profile shape of the electrode, such as a star pattern 1100 as illustrated in FIG. 10D, or by varying the thickness of the electrode, such as having an electrode that is thicker toward the center and thinner toward the edges, as illustrated in FIG. 9E, which illustrated the side view of an electrode with a tapered profile. FIG. 9E schematically shows a side view of a tapered electrode 1000 to improve the conformability and control of delivery of current at the edges of the electrode. As shown, the electrode 1000 can be thicker in the center of the electrode than at the peripheral edges of the electrode. In some embodiments, the thickness at the center of the electrode 1000 can be about or at least about 1.5×, 2×, 2.5×, 3×, 4×, 5×, 6×, 7×, 8×, 9×, 10×, or more times the thickness at the peripheral edges of the electrode. As illustrated in FIG. 10D, the top view of the star pattern electrode 1100 can include a central hub 1102 with a plurality, such as about or at least about 3, 4, 5, 6, 7, 8, 9, 10, or more radially outwardly extending projections 1104. The electrode can be integrally formed in some embodiments. In some embodiments, the patterned electrode can include a non-conductive material, such as silicone, wherein the star or other pattern is conductive and the outer, surrounding material is non-conductive, such as via a two-part molding process. In some embodiments, controlling the spatial resistivity of the electrode, for example by the amount of filler material, can also control the location of current delivery to stimulate skin and nerves in one or more preferred locations.

Figure 11A:
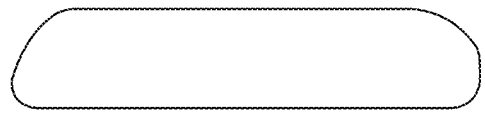
FIGS. 11A-11B illustrate views of electrode geometries with non-sharp edges and corners.
Figure 11B:
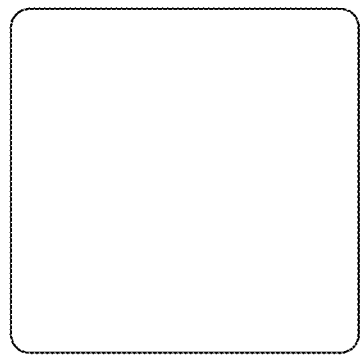

The shape of the electrode can also contribute to the ability to conform to the skin. If an electrode has edges and/or corners, such as in a square or rectangle shape, for instance, the edges and corners can deform and bend downward into the wearer's skin. This deformation can lead to uneven pressure at the skin contact layer, which can lead to localized concentration of current flow and discomfort. FIGS. 11A and 11B illustrate electrode shapes that may optimize conformity with the skin and homogenous current distribution. FIG. 11A illustrates a side cross sectional view of an electrode 1100. FIG. 11B illustrates a top view of an electrode 1100', which may be the same or a different electrode as electrode 1100 shown in FIG. 11A. Shapes, such as the pillowed-shape profile electrodes with tapered (e.g., rounded, non-sharp) edges as illustrated in FIG. 11A and/or electrodes with rounded corners as illustrated in FIG. 11B, prevent discomfort by reducing deformation of the electrode around the corners and edges when coming into contact with a person's skin. In some embodiments, the electrodes can have a generally square or rectangular geometry. In some embodiments, the electrodes can have an arcuate, e.g., circular or oval geometry (e.g., from a top view). Additionally, electrodes can in some cases protrude beyond the band surface to ensure that the electrode is the primary material touching the person's skin. Additionally, the shape of the electrode can also help with conformance—for instance, squares with rounded corners can reduce the chances of a single point contacting the skin.

Testing Apparatus

Figure 12A:
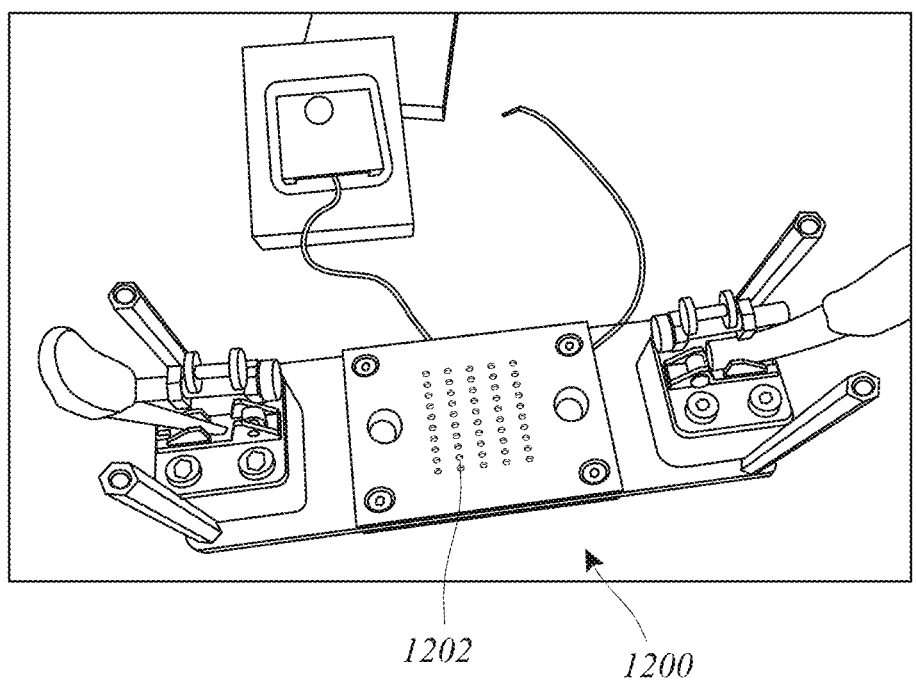
FIGS. 12A-12B illustrate electrode testing devices.
Figure 12B:
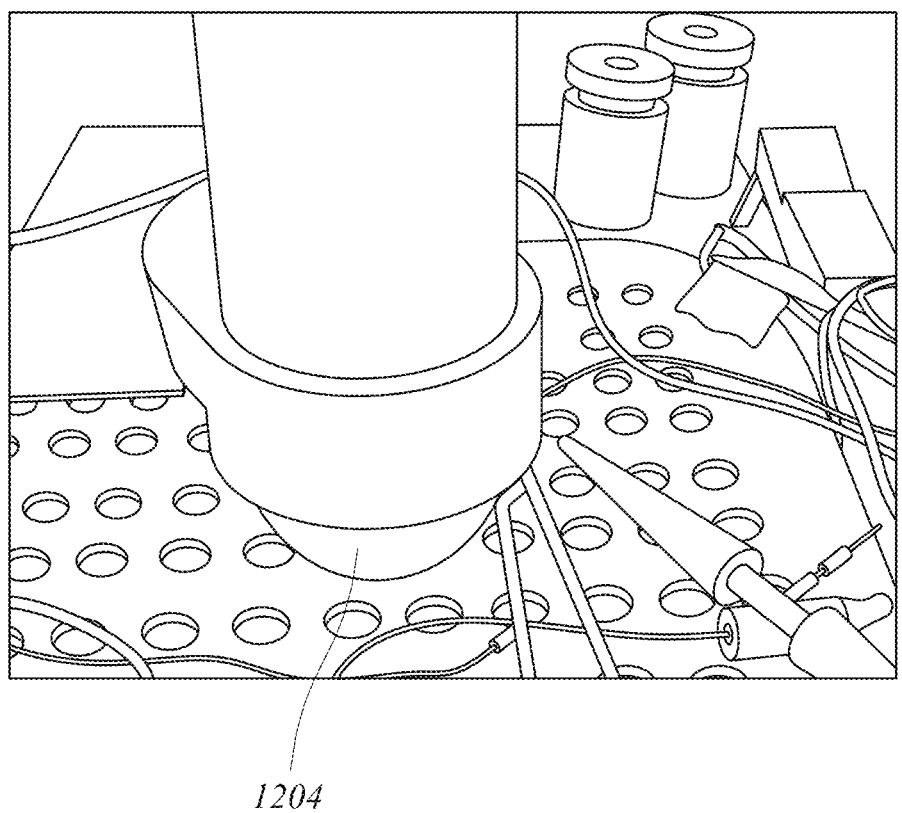

FIGS. 12A and 12B illustrate example of testing apparatuses for testing conductance of dry electrodes. FIG. 12A illustrates an embodiment of a pinpoint tester 1200 that can be used to assess the dry electrode consistency and uniformity of the resistance or conductance across the surface of the dry electrode. The pinpoint tester 1200 can have a first plate with a first array of electrodes 1202 that spans the entire area of the dry electrode to be tested, and a second plate (not visible) with a second array of electrodes that corresponds with the first array. For testing, the dry electrode or just the skin contact layer can be inserted between the two plates and compressed to a typical wearing pressure to ensure contact between the electrode arrays and the dry electrode. The pinpoint tester 1200 can then simultaneously measure the resistance or conductance of the dry electrode at a plurality of discrete points across the entire surface of the dry electrode. The resistance or conductance of the individual points can be statistically compared to determine the consistency or uniformity of material properties across the electrode surface. FIG. 12B shows an embodiment of a cylindrical tester 1204 used to measure the impedance of a configuration of electrodes affixed to a band attached around the cylindrical tester 1204 under a certain pressure/band pull force. The cylindrical tester 1204 can be used to approximate a relationship between the amount of pressure/force applied to the band and the conductance of the electrodes. Increased pressure/force should promote better contact/conformity between the dry electrodes and the cylindrical tester 1204, allowing better conduction between the electrodes and cylindrical tester 1204.

Wearable Band Configured for Dry Electrodes

FIG. 13A illustrates examples of an electrode 500 that is attached to the band through a snap fitting. The electrode 500 may comprise a number of apertures, such as around the perimeter of the electrode 500 that allows mechanical snaps to secure the electrode 500 to a band. FIG. 13B illustrates examples of an electrode 500' that is attached to the band through a welded wire 502 or electrical trace. The wire 502 may be welded to the electrode 500' and threaded into or otherwise secured to a band. The snap fitting requires more structural support than a direct wire connection, and therefore, the snap fitting tends to increase the rigidity of the electrodes on the band. By using a direct wire 502 or electrical trace connection, the flexibility of the electrodes 500' on the band can be improved, which improves skin conformance.

Figure 14C:
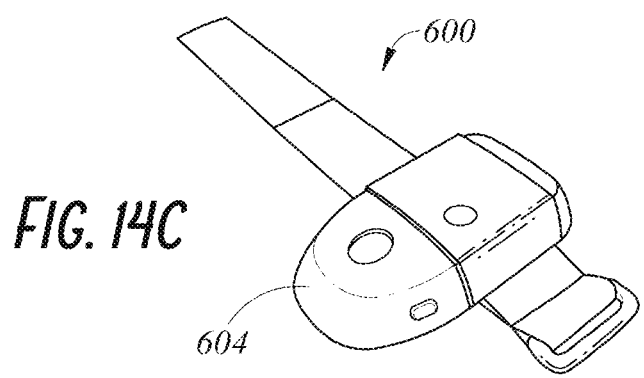
Figure 14D:
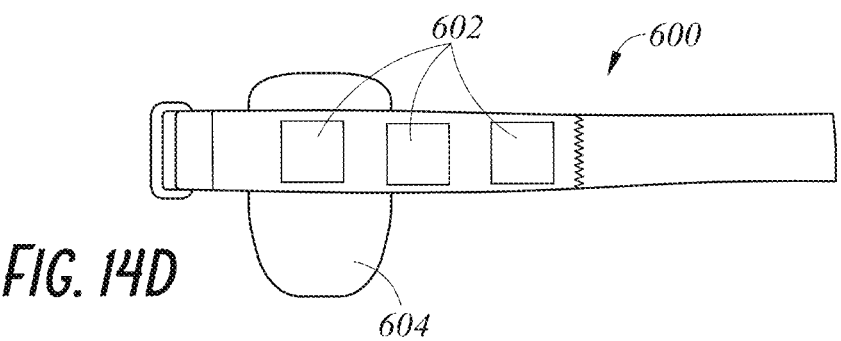
Figure 14E:
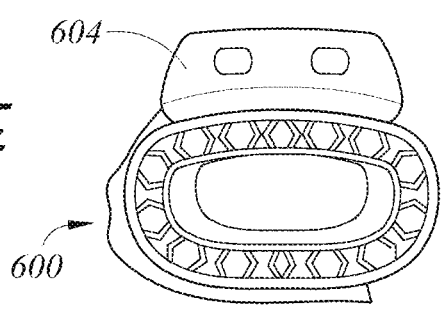
Figure 14F:
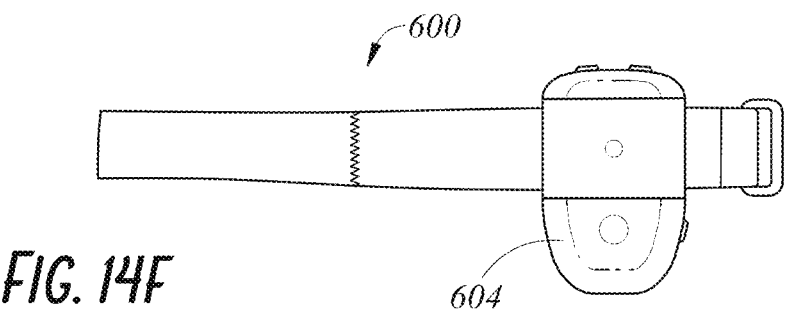

FIGS. 14A-14F illustrate an embodiment of a band 600 comprising 3 dry electrodes 602. FIG. 14A illustrates an underside or skin-facing side of the band 600. FIG. 14B illustrates an outer side or non-skin-facing side of the band 600, configured for attaching to a nerve stimulation device. FIG. 14C illustrates a top perspective view of the band 600 including a nerve stimulation device 600. FIG. 14D illustrates a bottom view of the skin-facing side of the band 600 including the nerve stimulation device 604. FIG. 14E illustrates a side view of the band 600 in a strapped configuration as if worn around a limb. FIG. 14F illustrates a top view of the band 600 including the nerve stimulation device 604. In some embodiments, the dry electrodes 602 may be aligned along the longitudinal axis of the band 600. The dry electrodes 602 can be spaced apart as illustrated in FIGS. 14A-14F. The dry electrodes 602 may be electrically attached to an electrical device, such as an electrical nerve stimulation device 604. The band 600 can have an elastic strap 606 (FIG. 14A) that allows the band 600 to be tensioned around the body part, such as the wrist, arm, ankle, or leg, for example. The band 600 can also use a hook and loop fastener 608 (FIG. 14B) to provide continuous adjustment capabilities which allows an adjustable amount of tension and pressure to be applied by the electrodes 602 to the wearer's skin. Flexible circuits can be incorporated into one or more layers in the band 600, as further described elsewhere herein, which electrically connect the electrodes 602 to at least one electrical connection tab 610 (FIG. 14B) on the side of the side of the band 600 which attaches to the electrical nerve stimulation device 604. The electrical connection tab 610 can be electrically coupled and physically secured to the electrical nerve stimulation device 604. In some embodiments, there may be two tabs on the band 600, both of which can be used to physically secure the electrical nerve stimulation device to the band 600, but only one tab may provide the electrical connection. In some embodiments, both tabs provide an electrical connection. In some embodiments, the electrical connection tabs 610 are separate from attachment tabs or features that are used to physically secure the electrical nerve stimulation 604 device to the band 600.

Figure 15D:
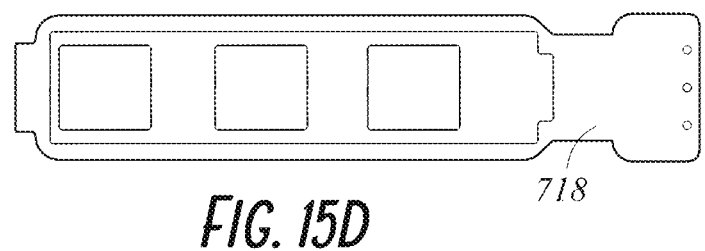
FIGS. 15A-15D illustrate an exploded view of the various layers and components of an embodiment of a band with dry electrodes.
Figure 15C:
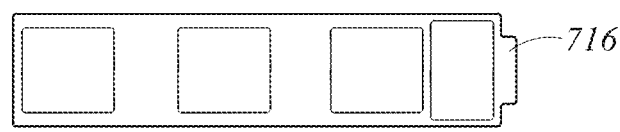
Figure 15B:
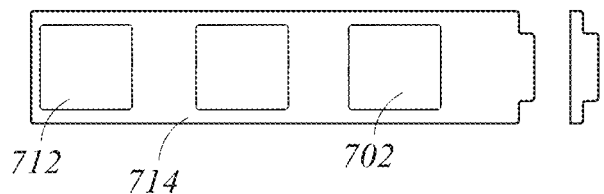
Figure 15A:
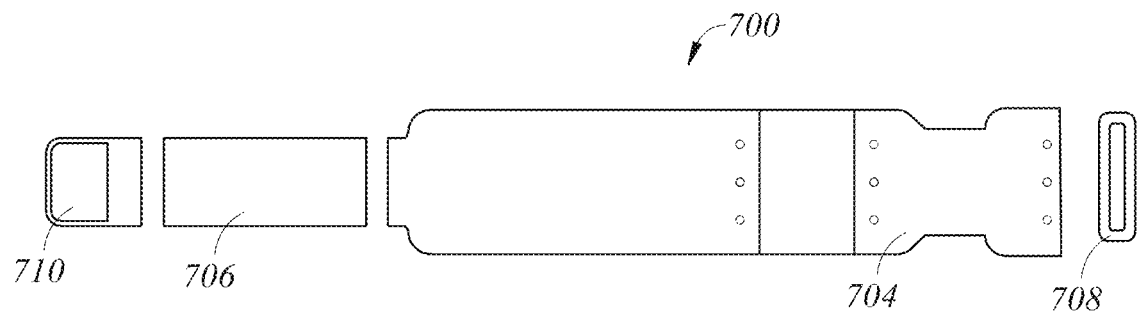

FIGS. 15A-15D illustrate examples of the various layers and components that can comprise an embodiment of the band 700 with dry electrodes 702. As shown in FIG. 15A, the top layer 704 of the band 700 can have an elastic portion 706, a D-ring 708 attached to one of the band 700 for receiving the other end of the band 700 and allowing it to loop back on itself, and a hook and loop fastener 710 (e.g., Velcro™) on the non-skin facing side of the band 700 for securing the band 700 around a body part. FIG. 15B illustrates the flex circuit 712 layer with overmolded conductive silicone electrodes 702 and an electrical connection tab 714. The base layer of the dry electrodes 702 may be directly integrated into the flex circuit 712. The electrical connection tab 714 can be an extension of the flex circuit that can be connected to an electrical nerve stimulation device. FIG. 15C illustrates an adhesive layer 716 with backing (e.g., 3M adhesive) that is used to attach the flex circuit 712 layer to the bottom layer 718 shown in FIG. 15D. The adhesive layer 716 may accordingly be adhesive on both sides. The adhesive layer 716 can have cutouts for receiving the electrodes 702. The bottom layer 718 has cutouts for receiving the electrodes 702 and an adhesive (e.g., a heat activated adhesive) disposed around the outer areas of the bottom layer 718 for attaching the bottom layer 718 to the top layer 704. As shown in FIG. 15D, a first area 719 (the darker/black area) of the bottom layer 718 corresponds and is attached to the adhesive layer 716. The first area 719 may be polycarbonate or another material specifically configured to adhere to the adhesive layer 716. A second area 720 (the lighter color area) may comprise the adhesive used to attach the top layer 704 and bottom layer 718 together. The skin-facing side of the bottom layer 718 can be a fabric or other comfortable material.

Figure 16A:
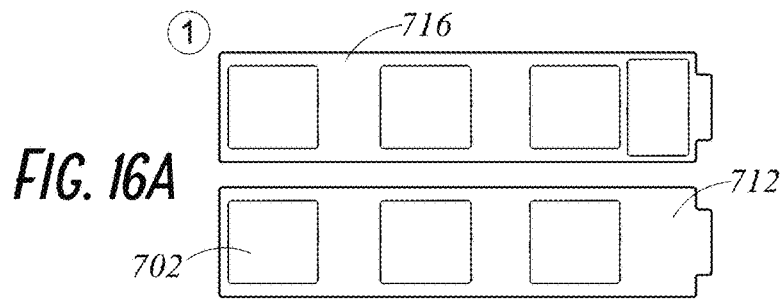
FIGS. 16A-16F illustrate the steps for an embodiment of a method of assembling the band shown in FIGS. 15A-15D.
Figure 16B:
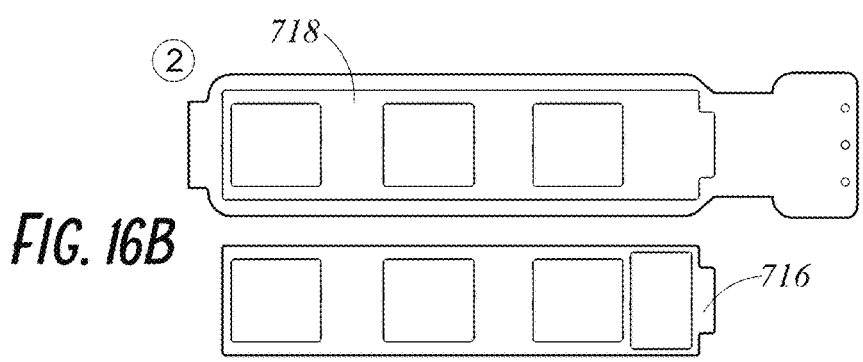
Figure 16C:
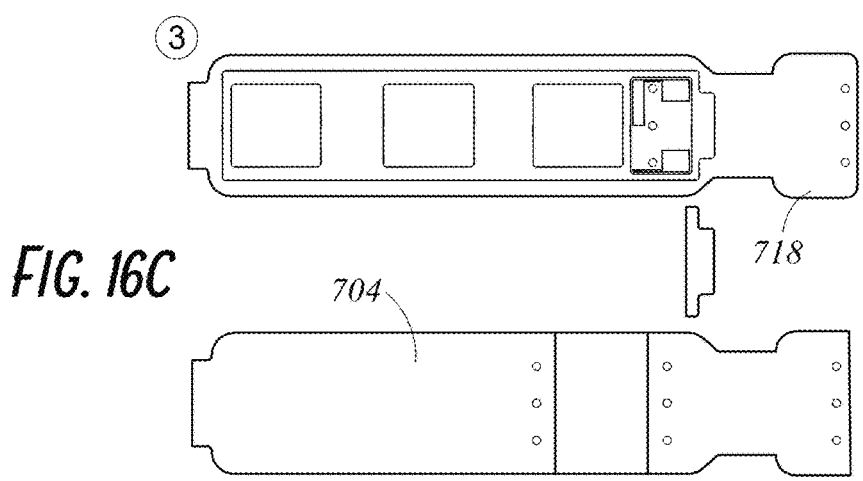
Figure 16D:
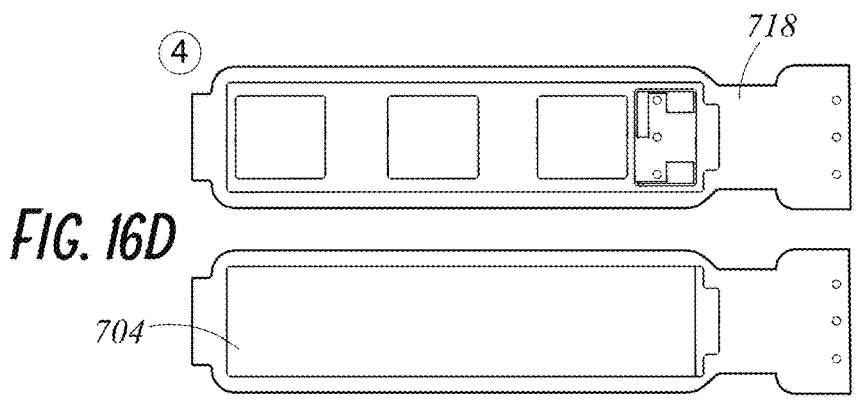
Figure 16E:
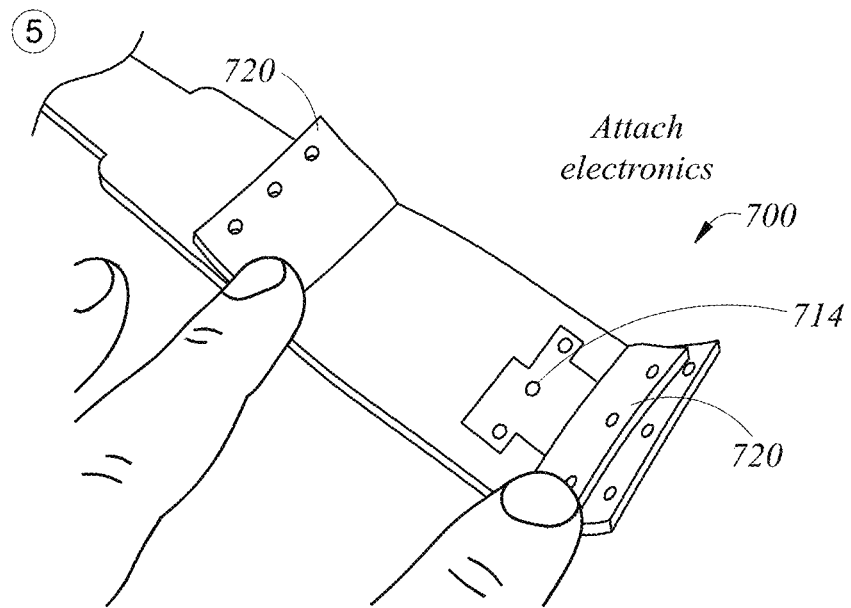
Figure 16F:
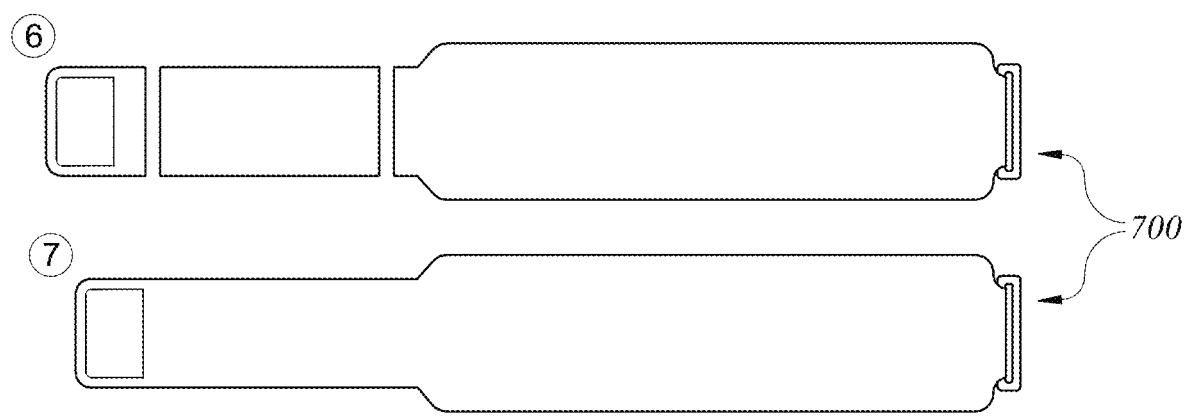

FIGS. 16A-16F illustrate the assembly (in numbered steps 1-7) of the band 700 and electrodes 702 shown in FIGS. 15A-15D. FIG. 16A illustrates the attachment of one side of the adhesive layer 716 to the flex circuit 712 layer. Then, as shown in FIG. 16B, the bottom layer 718 can be attached to the other side of the adhesive layer 716, thereby securing the flex circuit 712 layer to the bottom layer 718. Next, as shown in FIG. 16C, the adhesive used to attach the top and bottom layers 704, 718 can be activated (e.g., heat activated or UV activated). In other embodiments, a non-activated adhesive may be applied prior to this step. In some embodiments, the adhesive can change color when activated, which lets the person assembling the band know when the bottom layer 718 is ready to be attached to the top layer 704. Then, as shown in FIG. 16D, the top layer 704 can be attached to the bottom layer 718, thereby sandwiching the flex circuit layer 712 between the top layer 704 and bottom layer 718. The electrical connection tab 714 can be inserted through a slit or opening in the top layer 704. FIG. 16E illustrates the electrical connection tab 714 and separate physical securement tabs 720 that can be used to fasten a device to the band 700. FIG. 16F illustrates both sides of a fully assembled band 700, with step 6 showing the fully assembled skin-facing side of the band 700 and step 7 showing the fully assembled non-skin-facing side of the band 700. An electric nerve stimulator device, as described elsewhere herein, may subsequently be secured to the non-skin-facing side of the band 700.

In some embodiments, the band may have two or more tension settings that are adjustable by interacting with the band, such as through a control, e.g., a button or dial that adjusts band length to pre-selected settings or through a working range. The first tension setting could be at tension that applied enough pressure between the electrode and the wearer's skin for good conformance and comfortable stimulation during a specified stimulation session period. The second tension setting could be at a tension less than the first setting that secures the device to the wearer's limb, but not with enough pressure for good skin conformance, to allow for comfortable all day wear. The device could prevent stimulation at the second lower tension setting. Tension and pressure could be adjusted, for example, by changing the length of the band attached to the wearer's wrist or by inflating the band.

EXAMPLES

Example 1

Figure 17A:
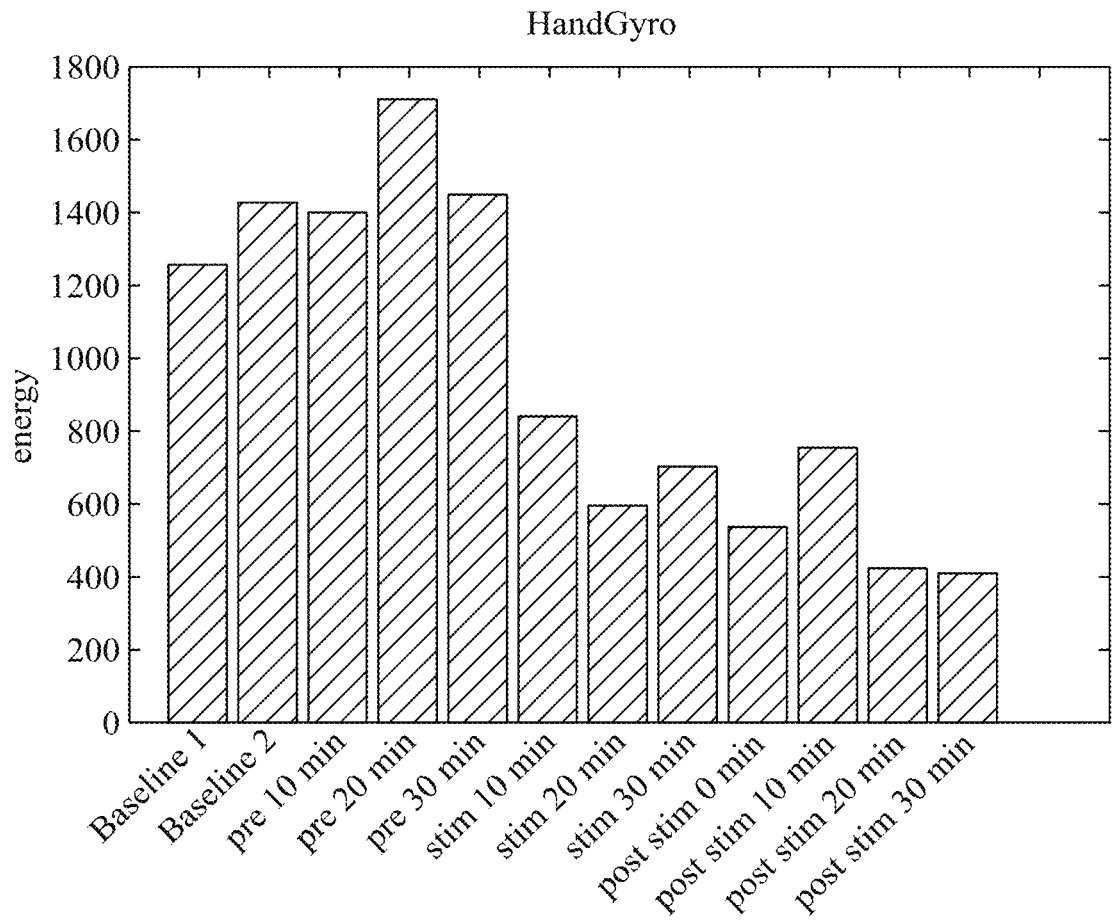
FIGS. 17A-17B depict results of treating tremor with nerve stimulation using a wearable device.
Figure 17B:
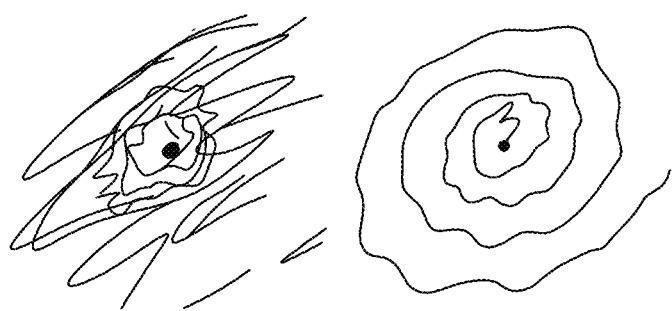

FIGS. 17A and 17B demonstrate dramatic tremor reduction after providing electrical stimulation to nerves in the patient's wrist in accordance with the embodiments described herein. FIG. 17A is an example of the tremor reduction detected using a gyroscope to measure the tremor energy during a postural hold. The severity of the tremor is measured by the energy output according to the hand gyroscope. Two baseline measurements were recorded with no stimulation. The energy was measured for different durations of the postural hold (0, 10, 20, or 30 min) either before, during, or after application of a therapeutic stimulation protocol by a nerve stimulation device as described according to the embodiments herein. The results demonstrate discernable reduction in hand tremor both during and after the stimulation. FIG. 17B is an example of the tremor reduction as detected by having the patient draw a spiral before nerve stimulation (left) and after nerve stimulation (right). The spiral pattern is noticeably less distorted after nerve stimulation treatment. Stimulation was delivered for about 40 minutes. In some embodiments, stimulation can be delivered from between about 40 minutes to about 120 minutes, or up to about 8 hours in some cases.

Example 2

Figure 18A:
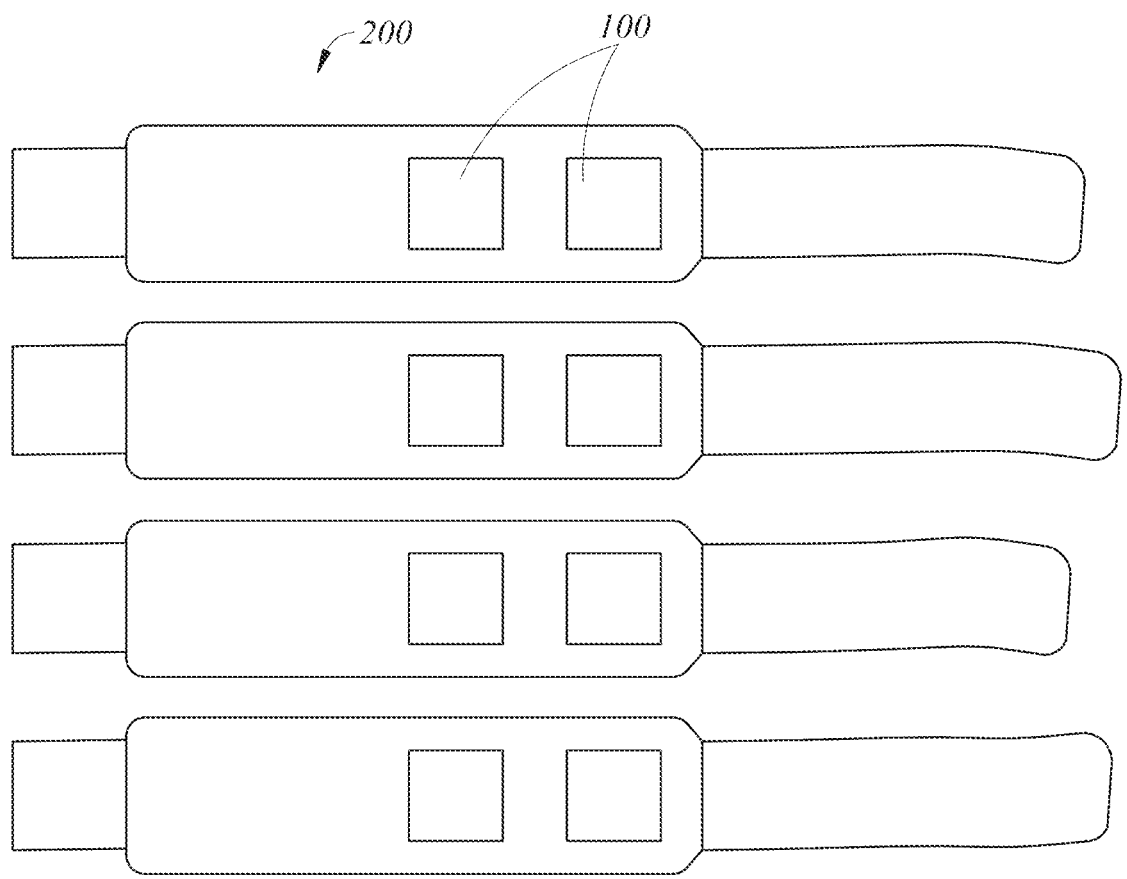
FIGS. 18A-18F depict a wearable band and user feedback regarding the comfort of using the band for nerve stimulation.

FIG. 18A illustrates examples of an embodiment of a wearable band 1800 comprising two dry electrodes 1802 that was tested on 15 subjects in order to determine if the electrodes were comfortable for all day use. Subjects were stimulated for 120 minutes, which was equivalent to about 3 typical stimulation sessions for treating hand tremors due to essential tremor. In addition, subjects wore the band 1800 for an additional 8 hours without stimulation, for a total wear time of 10 hours per day. The target acceptance criteria was that at least 80% of the subjects would find the device comfortable for all day use.

Figure 18B:
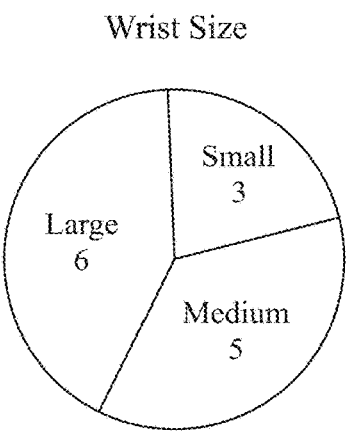
Figure 18C:
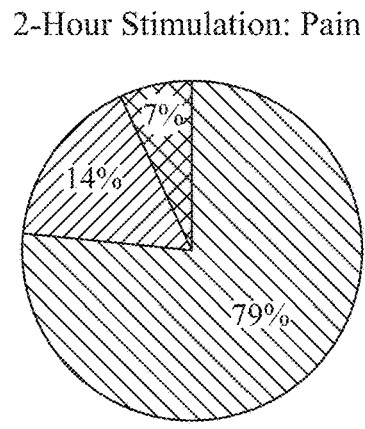
Figure 18D:
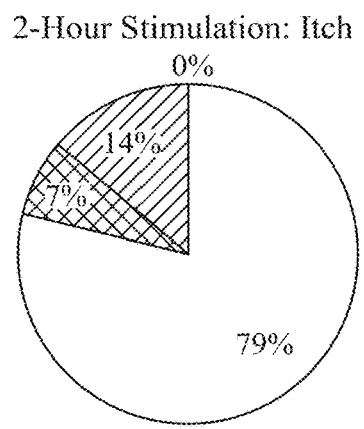
Figure 18E:
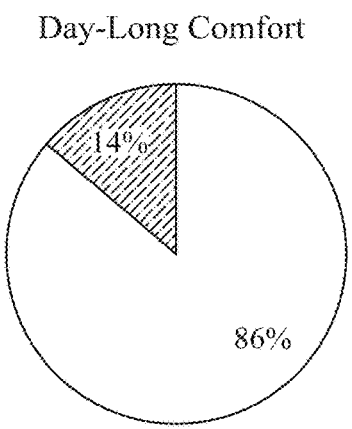
Figure 18F:
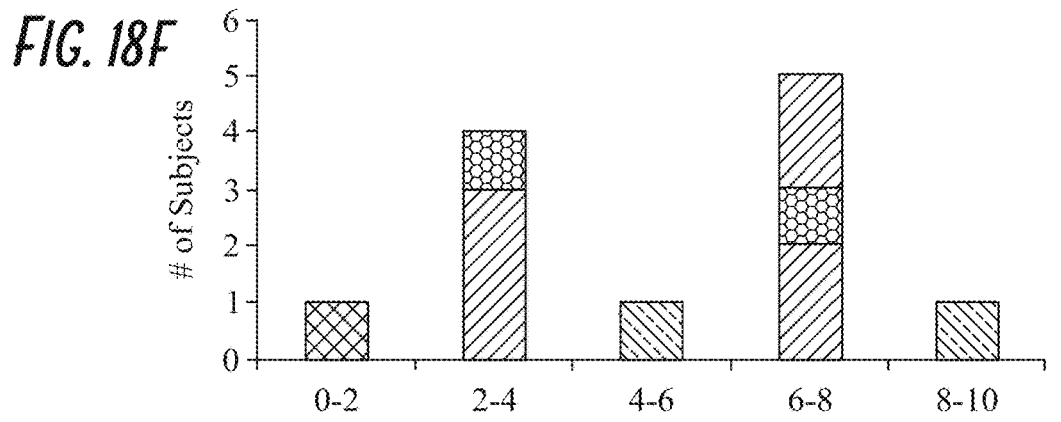

FIGS. 18B-18F illustrates preliminary data from the study that show that the vast majority of subjects felt that wearing and using the dry electrodes was comfortable. FIG. 18B shows the distribution of wrist size (small, medium, or large) for 14 of the subjects. Small wrists sized at or under 13.5-15.5 cm, medium wrists sized between 15.5-17.5 cm, and large wrists sized at or above 17.5-19.5 cm. As shown in FIG. 18C, 79% of the subjects did not experience pain from a 2 hour stimulation using the dry electrode, 14% of the subjects experienced only transient pain, and only 7% of the subjects experienced persistent pain. As shown in FIG. 18D, at least 86% of the subjects felt that wearing the electrodes throughout the day was comfortable (experienced no discomfort). As shown in FIG. 18E, at least 79% of the subjects felt no itchiness from the 2 hour stimulation, and only 14% of the subjects felt transient itchiness, while no subjects had yet reported persistent itchiness. FIG. 18F shows preliminary distributions of the number of subjects experiencing relative pain/comfort levels (comfortable, transient itch, transient pain, persistent pain) at various levels (currents) of nerve stimulation.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. The methods disclosed herein include certain actions taken by a practitioner; however, they can also include any third-party instruction of those actions, either expressly or by implication. For example, actions such as "percutaneously stimulating an afferent peripheral nerve" includes "instructing the stimulation of an afferent peripheral nerve."

What is claimed is:

1. A dry electrode for transcutaneous electrical stimulation, the dry electrode comprising:
   a conductive backing layer; and
   a skin contact layer disposed on the conductive backing layer, the skin contact layer configured to deliver electrical current from the conductive backing layer to the skin for transcutaneous electrical stimulation, the skin contact layer comprising a polymer, plastic, or rubber material, and a conductive filler material dispersed substantially evenly throughout the polymer, plastic, or rubber material, the skin contact layer comprising a thickness of between 1 mm and 10 mm, wherein the conductive filler material comprises single wall carbon nanotubes,
   wherein the skin contact layer comprises a skin facing surface that is not coated with a hydrogel or liquid,
   wherein a loading of single wall carbon nanotubes is between about 1% and about 5%, and
   wherein a homogeneity of the conductive filler material is such that there is less than about a 5% difference in resistivity across the skin contact layer.

2. The dry electrode of claim 1, wherein the dry electrode has a bulk resistivity of between about 50 ohm-cm and about 1,000 ohm-cm,
   wherein the skin contact layer comprises silicone,
   wherein the dry electrode is configured to be disposed on a wearable band, and wherein the skin contact layer has a Shore A durometer of between about 30 A and about 50 A.

3. The dry electrode of claim 1, wherein the skin contact layer comprises silicone.

4. The dry electrode of claim 1, wherein the conductive filler material further comprises silver coated glass bubbles.

5. The dry electrode of claim 4, wherein the loading of silver coated glass bubbles is between about 3% and about 30% of the skin contact layer.

6. The dry electrode of claim 1, wherein the dry electrode has a bulk resistivity of between about 50 ohm-cm and about 1,000 ohm-cm.

7. The dry electrode of claim 1, wherein the skin contact layer has a Shore A durometer of between about 30 A and about 50 A.

8. A dry electrode for transcutaneous electrical stimulation, the dry electrode comprising:
a conductive backing layer; and
a skin contact layer disposed on the conductive backing layer, the skin contact layer configured to deliver electrical current from the conductive backing layer to the skin for transcutaneous electrical stimulation, the skin contact layer comprising a polymer, plastic, or rubber material, and a conductive filler material dispersed throughout the polymer, plastic, or rubber material, the skin contact layer comprising a thickness of between 1 mm and 10 mm, wherein the conductive filler material comprises single wall carbon nanotubes,
wherein the skin contact layer comprises a skin facing surface that is not coated with a hydrogel or liquid,
wherein a loading of single wall carbon nanotubes is between about 1% and about 5%.

9. The dry electrode of claim 8, wherein the dry electrode has a bulk resistivity of between about 50 ohm-cm and about 1,000 ohm-cm,
wherein the skin contact layer has a Shore A durometer of between about 30 A and about 50 A,
wherein a homogeneity of the conductive filler material is such that there is less than about a 5% difference in resistivity across the skin contact layer,
wherein the loading of single wall carbon nanotubes is between about 1% and about 5%, and
wherein the skin contact layer comprises silicone.

10. The dry electrode of claim 8, wherein the skin contact layer comprises silicone.

11. A dry electrode for transcutaneous electrical stimulation, the dry electrode comprising:
a conductive backing layer; and
a skin contact layer disposed on the conductive backing layer, the skin contact layer configured to deliver electrical current from the conductive backing layer to the skin for transcutaneous electrical stimulation, the skin contact layer further comprising a conductive filler material dispersed substantially evenly throughout a polymer, plastic, or rubber material, the skin contact layer comprising a thickness of between 0.5 mm and 10 mm, wherein the conductive filler material comprises single wall carbon nanotubes,
wherein the skin contact layer has a skin facing surface that is not coated with a hydrogel or liquid,
wherein a loading of single wall carbon nanotubes is less than about 5%.

12. The dry electrode of claim 11,
wherein the skin contact layer has a Shore hardness between about 10 A to about 100 A,
wherein the skin contact layer has a volume resistivity between about 1 ohm*cm and about 2000 ohm*cm,
wherein a measured resistance or conductance at a plurality of points across the skin facing surface of the skin contact layer has a standard deviation of within about 50% of the average measured resistance or conductance, and
wherein the skin contact layer comprises silicone.

13. The dry electrode of claim 11, wherein the conductive backing layer comprises a metal foil.

14. The dry electrode of claim 13, wherein the metal foil is disposed on a flexible polymer substrate.

15. The dry electrode of claim 11, wherein the conductive filler material comprises a powder or fine particulate material.

16. The dry electrode of claim 11, wherein the conductive backing layer comprises porous material treated with a conductive coating.

17. The dry electrode of claim 11, wherein the skin contact layer has a Shore hardness between about 10 A to about 100 A.

18. The dry electrode of claim 11, wherein the skin contact layer has a Shore hardness between about 25 A to about 55 A.

19. The dry electrode of claim 11, wherein a measured resistance or conductance at a plurality of points across the skin facing surface of the skin contact layer has a standard deviation of within about 25% of the average measured resistance or conductance.

20. The dry electrode of claim 11, wherein the loading of single wall carbon nanotubes is between about 1% and about 5%.

* * * * *